(12) United States Patent
Bonner et al.

(10) Patent No.: US 11,951,313 B2
(45) Date of Patent: Apr. 9, 2024

(54) VFA DELIVERY SYSTEMS AND METHODS

(71) Applicant: Medtronic, Inc., Minneapolis, MN (US)

(72) Inventors: Matthew D. Bonner, Plymouth, MN (US); Andrea J. Asleson, Maple Grove, MN (US); Jean M. Carver, Blaine, MN (US); Kathryn Hilpisch, Cottage Grove, MN (US)

(73) Assignee: Medtronic, Inc., Minneapolis, MN (US)

(*) Notice: Subject to any disclaimer, the term of this patent is extended or adjusted under 35 U.S.C. 154(b) by 475 days.

(21) Appl. No.: 16/683,413

(22) Filed: Nov. 14, 2019

(65) Prior Publication Data

US 2020/0155845 A1     May 21, 2020

Related U.S. Application Data

(60) Provisional application No. 62/768,891, filed on Nov. 17, 2018.

(51) Int. Cl.
*A61N 1/36* (2006.01)
*A61N 1/05* (2006.01)
(Continued)

(52) U.S. Cl.
CPC .............. *A61N 1/368* (2013.01); *A61N 1/05* (2013.01); *A61N 1/37518* (2017.08);
(Continued)

(58) Field of Classification Search
CPC ...... A61N 1/368; A61N 1/05; A61N 1/37518; A61N 1/3756; A61N 1/37512;
(Continued)

(56) References Cited

U.S. PATENT DOCUMENTS 3,835,864 A   9/1974   Rasor et al.
3,865,118 A   2/1975   Bures
(Continued)

FOREIGN PATENT DOCUMENTS

AU   2008279789   10/2011
AU   2008329620   5/2014
(Continued)

OTHER PUBLICATIONS

US 8,886,318 B2, 11/2014, Jacobson et al. (withdrawn)
(Continued)

*Primary Examiner* — Amanda K Hulbert
*Assistant Examiner* — Natasha Patel
(74) *Attorney, Agent, or Firm* — Mueting Raasch Group

(57) ABSTRACT

Devices, systems, and methods deliver implantable medical devices for ventricular-from-atrial (VfA) cardiac therapy. A VfA device may be implanted in the right atrium (RA) with an electrode extending from the right atrium into the left ventricular myocardium. A flexible leed, or another probe, may be advanced to the potential implantation site and used to identify a precise location for implantation of a medical device, such as an electrode, leadlet, lead, or intracardiac device. Some methods may include locating a potential implantation site in the triangle of Koch region in the right atrium of a patient's heart; attaching a fixation sheath to the right-atrial endocardium in the potential implantation site; and implanting the medical device over a guide wire at the potential implantation site. An implantable medical device may include an intracardiac housing and a leadlet, which may be delivered by these methods.

6 Claims, 44 Drawing Sheets

(51) Int. Cl.
*A61N 1/368* (2006.01)
*A61N 1/375* (2006.01)
*A61N 1/39* (2006.01)

(52) U.S. Cl.
CPC ........ *A61N 1/3756* (2013.01); *A61N 1/37512* (2017.08); *A61N 1/39622* (2017.08)

(58) Field of Classification Search
CPC .............. A61N 1/39622; A61N 1/3684; A61N 1/3702; A61B 5/287; A61B 5/349; A61B 17/3468; A61B 17/3478; A61B 5/6852; A61B 5/6869; A61B 5/4836
See application file for complete search history.

(56) References Cited

U.S. PATENT DOCUMENTS

| | | |
|---|---|---|
| 3,943,936 A | 3/1976 | Rasor et al. |
| 3,949,757 A | 4/1976 | Sabel |
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Mass |
| 4,250,884 A | 2/1981 | Hartlaub et al. |
| 4,256,115 A | 3/1981 | Bilitch |
| 4,263,919 A | 4/1981 | Levin |
| 4,280,502 A | 7/1981 | Baker, Jr. et al. |
| 4,289,144 A | 9/1981 | Gilman |
| 4,310,000 A | 1/1982 | Lindemans |
| 4,312,354 A | 1/1982 | Walters |
| 4,323,081 A | 4/1982 | Wiebusch |
| 4,332,259 A | 6/1982 | McCorkle, Jr. |
| 4,357,946 A | 11/1982 | Dutcher et al. |
| 4,365,639 A | 12/1982 | Goldreyer |
| 4,374,382 A | 2/1983 | Markowitz et al. |
| 4,393,883 A | 7/1983 | Smyth et al. |
| 4,440,173 A | 4/1984 | Hudziak et al. |
| 4,476,868 A | 10/1984 | Thompson |
| 4,479,500 A | 10/1984 | Smits |
| 4,522,208 A | 6/1985 | Buffet |
| 4,537,200 A | 8/1985 | Widrow |
| 4,546,777 A | 10/1985 | Groch et al. |
| 4,556,063 A | 12/1985 | Thompson et al. |
| 4,562,841 A | 1/1986 | Brockway et al. |
| 4,574,814 A | 3/1986 | Buffet |
| 4,593,702 A | 6/1986 | Kepski et al. |
| 4,593,955 A | 6/1986 | Leiber |
| 4,630,204 A | 12/1986 | Mortara |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,830,006 A | 5/1989 | Haluska et al. |
| 4,858,610 A | 8/1989 | Callaghan et al. |
| 4,865,037 A | 9/1989 | Chin et al. |
| 4,886,064 A | 12/1989 | Strandberg |
| 4,887,609 A | 12/1989 | Cole, Jr. |
| 4,928,688 A | 5/1990 | Mower |
| 4,953,564 A | 9/1990 | Berthelsen |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,053,004 A | 10/1991 | Markel et al. |
| 5,058,581 A | 10/1991 | Silvian |
| 5,078,134 A | 1/1992 | Heilman et al. |
| 5,107,850 A | 4/1992 | Olive |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grievous et al. |
| 5,133,353 A | 7/1992 | Hauser |
| 5,144,950 A | 9/1992 | Stoop et al. |
| 5,154,170 A | 10/1992 | Bennett et al. |
| 5,170,784 A | 12/1992 | Ramon et al. |
| 5,174,289 A | 12/1992 | Cohen |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,255,692 A | 10/1993 | Neubauer et al. |
| 5,259,387 A | 11/1993 | dePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,594 A | 6/1994 | Limousin et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | Decoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,487,758 A | 1/1996 | Hoegnelid et al. |
| 5,507,802 A | 4/1996 | Imran |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,554,177 A | 9/1996 | Kieval et al. |
| 5,562,711 A | 10/1996 | Yerich et al. |
| 5,571,146 A | 11/1996 | Jones et al. |
| 5,591,214 A | 1/1997 | Lu |
| 5,601,615 A | 2/1997 | Markowitz et al. |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,140 A | 3/1998 | Salo et al. |
| 5,728,154 A | 3/1998 | Crossett et al. |
| 5,741,314 A | 4/1998 | Daly et al. |
| 5,741,315 A | 4/1998 | Lee et al. |
| 5,749,909 A | 5/1998 | Schroeppel et al. |
| 5,752,976 A | 5/1998 | Duffin et al. |
| 5,752,977 A | 5/1998 | Grievous et al. |
| 5,755,736 A | 5/1998 | Gillberg et al. |
| 5,759,199 A | 6/1998 | Snell et al. |
| 5,774,501 A | 6/1998 | Halpern et al. |

(56) References Cited

U.S. PATENT DOCUMENTS

| | | |
|---|---|---|
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,817,130 A | 10/1998 | Cox et al. |
| 5,827,216 A | 10/1998 | Igo et al. |
| 5,836,985 A | 11/1998 | Goyal et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,928,271 A | 7/1999 | Hess et al. |
| 5,935,078 A | 8/1999 | Feierbach |
| 5,941,906 A | 8/1999 | Barreras et al. |
| 5,944,744 A | 8/1999 | Paul et al. |
| 5,954,757 A | 9/1999 | Gray |
| 5,964,795 A | 10/1999 | McVenes et al. |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | dePinto |
| 6,044,298 A | 3/2000 | Salo et al. |
| 6,044,300 A | 3/2000 | Gray |
| 6,055,454 A | 4/2000 | Heemels |
| 6,070,104 A | 5/2000 | Hine et al. |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,132,456 A | 10/2000 | Sommer et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,212,434 B1 | 4/2001 | Scheiner et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,256,537 B1 | 7/2001 | Stoop et al. |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,903 B1 | 9/2001 | Rosenthal et al. |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,393,316 B1 | 5/2002 | Gillberg et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,756 B1 | 1/2003 | Heynen |
| 6,507,759 B1 | 1/2003 | Prutchi et al. |
| 6,508,771 B1 | 1/2003 | Padmanabhan et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,544,270 B1 | 4/2003 | Zhang |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,623,518 B2 | 9/2003 | Thompson et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,754,528 B2 | 6/2004 | Bardy et al. |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |

(56) References Cited

U.S. PATENT DOCUMENTS

| | | |
|---|---|---|
| 6,847,844 B2 | 1/2005 | Sun et al. |
| 6,869,404 B2 | 3/2005 | Schulhauser et al. |
| 6,871,095 B2 | 3/2005 | Stahmann et al. |
| 6,871,096 B2 | 3/2005 | Hill |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,931,286 B2 | 8/2005 | Sigg et al. |
| 6,934,585 B1 | 8/2005 | Schloss et al. |
| 6,941,169 B2 | 9/2005 | Pappu |
| 6,957,107 B2 | 10/2005 | Rogers et al. |
| 6,978,176 B2 | 12/2005 | Lattouf |
| 6,980,675 B2 | 12/2005 | Evron et al. |
| 6,985,773 B2 | 1/2006 | Von Arx et al. |
| 6,988,007 B1 | 1/2006 | Morgan et al. |
| 6,990,375 B2 | 1/2006 | Kloss et al. |
| 6,993,389 B2 | 1/2006 | Ding et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,176 B2 | 3/2006 | Ding et al. |
| 7,013,178 B2 | 3/2006 | Reinke et al. |
| 7,027,871 B2 | 4/2006 | Burnes et al. |
| 7,031,711 B2 | 4/2006 | Brown et al. |
| 7,031,771 B2 | 4/2006 | Brown et al. |
| 7,035,684 B2 | 4/2006 | Lee et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,177,704 B2 | 2/2007 | Laske et al. |
| 7,181,284 B2 | 2/2007 | Burnes et al. |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,231,248 B2 | 6/2007 | Kramer et al. |
| 7,231,253 B2 | 6/2007 | Tidemand et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,286,866 B2 | 10/2007 | Okerlund et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,307,321 B1 | 12/2007 | Avanzino |
| 7,308,297 B2 | 12/2007 | Reddy et al. |
| 7,308,299 B2 | 12/2007 | Burrell et al. |
| 7,310,556 B2 | 12/2007 | Bulkes |
| 7,317,950 B2 | 1/2008 | Lee |
| 7,319,905 B1 | 1/2008 | Morgan et al. |
| 7,321,677 B2 | 1/2008 | Evron et al. |
| 7,321,798 B2 | 1/2008 | Muhlenberg et al. |
| 7,333,853 B2 | 2/2008 | Mazar et al. |
| 7,336,994 B2 | 2/2008 | Hettrick et al. |
| 7,346,381 B2 | 3/2008 | Okerlund et al. |
| 7,346,393 B2 | 3/2008 | Spinelli et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,386,351 B2 | 6/2008 | Hine et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,454,248 B2 | 11/2008 | Burrell et al. |
| 7,496,409 B2 | 2/2009 | Greenhut et al. |
| 7,496,410 B2 | 2/2009 | Heil |
| 7,499,743 B2 | 3/2009 | Vass et al. |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,515,971 B1 * | 4/2009 | Doan .................. A61B 5/0215 600/375 |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,546,166 B2 | 6/2009 | Michels et al. |
| 7,558,626 B2 | 7/2009 | Corbucci |
| 7,558,631 B2 | 7/2009 | Cowan et al. |
| 7,565,190 B2 | 7/2009 | Okerlund et al. |
| 7,565,195 B1 | 7/2009 | Kroll et al. |
| 7,584,002 B2 | 9/2009 | Burnes et al. |
| 7,587,074 B2 | 9/2009 | Zarkh et al. |
| 7,590,455 B2 | 9/2009 | Heruth et al. |
| 7,599,730 B2 | 10/2009 | Hunter et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,613,500 B2 | 11/2009 | Vass et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,764 B2 | 12/2009 | Ding et al. |
| 7,630,767 B1 | 12/2009 | Poore et al. |
| 7,634,313 B1 | 12/2009 | Kroll et al. |
| 7,635,541 B2 | 12/2009 | Scott et al. |
| 7,637,867 B2 | 12/2009 | Zdeblick |
| 7,640,057 B2 | 12/2009 | Libbus et al. |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,657,313 B2 | 2/2010 | Rom |
| 7,668,596 B2 | 2/2010 | Von Arx et al. |
| 7,682,316 B2 | 3/2010 | Anderson et al. |
| 7,691,047 B2 | 4/2010 | Ferrari |

(56) References Cited

U.S. PATENT DOCUMENTS

| | | | |
|---|---|---|---|
| 7,702,392 B2 | 4/2010 | Echt et al. |
| 7,706,879 B2 | 4/2010 | Burnes et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,629 B2 | 6/2010 | Zarkh et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,047 B2 | 6/2010 | Okerlund et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,778,685 B2 | 8/2010 | Evron et al. |
| 7,778,686 B2 | 8/2010 | Vass et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,813,785 B2 | 10/2010 | Okerlund et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,877,144 B2 | 1/2011 | Coles, Jr. et al. |
| 7,881,786 B2 | 2/2011 | Jackson |
| 7,881,791 B2 | 2/2011 | Sambelashvili et al. |
| 7,881,798 B2 | 2/2011 | Miesel et al. |
| 7,881,806 B2 | 2/2011 | Horrigan et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,902 B2 | 2/2011 | Rom |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,912,544 B1 | 3/2011 | Min et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,027 B2 | 4/2011 | Prakash et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,941,218 B2 | 5/2011 | Sambelashvili et al. |
| 7,945,333 B2 | 5/2011 | Jacobson |
| 7,946,997 B2 | 5/2011 | Hubinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,063 B2 | 8/2011 | Vass et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,002,718 B2 | 8/2011 | Buchholtz et al. |
| 8,010,191 B2 | 8/2011 | Zhu et al. |
| 8,010,209 B2 | 8/2011 | Jacobson |
| 8,014,861 B2 | 9/2011 | Zhu et al. |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,065 B2 | 10/2011 | Burnes et al. |
| 8,046,079 B2 | 10/2011 | Bange et al. |
| 8,046,080 B2 | 10/2011 | Von Arx et al. |
| 8,050,297 B2 | 11/2011 | Delmain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,185 B2 | 11/2011 | Hunter et al. |
| 8,060,212 B1 | 11/2011 | Rios et al. |
| 8,065,018 B2 | 11/2011 | Haubrich et al. |
| 8,068,920 B2 | 11/2011 | Gaudiani |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,105,714 B2 | 1/2012 | Schmidt et al. |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,142,363 B1 | 3/2012 | Eigler et al. |
| 8,145,308 B2 | 3/2012 | Sambelashvili et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,428 B2 | 5/2012 | Kaiser et al. |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,590 B2 | 6/2012 | Sambelashvili et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,041 B2 | 7/2012 | Van Gelder et al. |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,262,578 B1 | 9/2012 | Bharmi et al. |
| 8,265,748 B2 | 9/2012 | Liu et al. |
| 8,265,757 B2 | 9/2012 | Mass et al. |
| 8,280,521 B2 | 10/2012 | Haubrich et al. |

(56) References Cited

U.S. PATENT DOCUMENTS

| | | |
|---|---|---|
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,014 B2 | 11/2012 | Maskara et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,027 B2 | 1/2013 | Spinelli et al. |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,383,269 B2 | 2/2013 | Scott et al. |
| 8,386,051 B2 | 2/2013 | Rys |
| 8,391,964 B2 | 3/2013 | Musley et al. |
| 8,391,981 B2 | 3/2013 | Mosesov |
| 8,391,990 B2 | 3/2013 | Smith et al. |
| 8,401,616 B2 | 3/2013 | Verard et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,406,899 B2 | 3/2013 | Reddy et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,716 B2 | 4/2013 | Mullen et al. |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,467,871 B2 | 6/2013 | Maskara |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,509,916 B2 | 8/2013 | Byrd et al. |
| 8,515,559 B2 | 8/2013 | Roberts et al. |
| 8,521,268 B2 | 8/2013 | Zhang et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matoes |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,594,775 B2 | 11/2013 | Ghosh et al. |
| 8,612,002 B2 | 12/2013 | Faltys et al. |
| 8,615,310 B2 | 12/2013 | Khairkhahan et al. |
| 8,617,082 B2 | 12/2013 | Zhang et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,333 B2 | 1/2014 | Stadler et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,314 B2 | 3/2014 | Maskara et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | Dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,731,642 B2 | 5/2014 | Zarkh et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,750,994 B2 | 6/2014 | Ghosh et al. |
| 8,750,998 B1 | 6/2014 | Ghosh et al. |
| 8,755,884 B2 | 6/2014 | Demmer et al. |
| 8,758,365 B2 | 6/2014 | Bonner et al. |
| 8,768,459 B2 | 7/2014 | Ghosh et al. |
| 8,768,483 B2 | 7/2014 | Schmitt et al. |
| 8,774,572 B2 | 7/2014 | Hamamoto |
| 8,781,582 B2 | 7/2014 | Ziegler et al. |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,861,830 B2 | 10/2014 | Brada et al. |
| 8,868,186 B2 | 10/2014 | Kroll |
| 8,886,307 B2 | 11/2014 | Sambelashvili et al. |
| 8,886,311 B2 | 11/2014 | Anderson et al. |
| 8,886,339 B2 | 11/2014 | Faltys et al. |
| 8,903,473 B2 | 12/2014 | Rogers et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,948,883 B2 | 2/2015 | Eggen et al. |
| 8,958,892 B2 | 2/2015 | Khairkhahan et al. |
| 8,972,228 B2 | 3/2015 | Ghosh et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,033,996 B1 | 5/2015 | West |
| 9,037,262 B2 | 5/2015 | Regnier et al. |
| 9,042,984 B2 | 5/2015 | Demmer et al. |
| 9,072,872 B2 | 7/2015 | Asleson et al. |

(56) References Cited

U.S. PATENT DOCUMENTS

| | | |
|---|---|---|
| 9,072,911 B2 | 7/2015 | Hastings et al. |
| 9,072,913 B2 | 7/2015 | Jacobson |
| 9,101,281 B2 | 8/2015 | Reinert et al. |
| 9,119,959 B2 | 9/2015 | Rys et al. |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashbili et al. |
| 9,302,115 B2 | 4/2016 | Molin et al. |
| 9,320,446 B2 | 4/2016 | Gillberg et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Regnier et al. |
| 9,457,193 B2 | 10/2016 | Klimovitch et al. |
| 9,474,457 B2 | 10/2016 | Ghosh et al. |
| 9,486,151 B2 | 11/2016 | Ghosh et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,510,763 B2 | 12/2016 | Ghosh et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,517,336 B2 | 12/2016 | Eggen et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,579,500 B2 | 2/2017 | Rys et al. |
| 9,623,234 B2 | 4/2017 | Anderson |
| 9,636,511 B2 | 5/2017 | Carney et al. |
| 9,643,014 B2 | 5/2017 | Zhang et al. |
| 9,675,579 B2 | 6/2017 | Rock et al. |
| 9,707,399 B2 | 7/2017 | Zielinski et al. |
| 9,724,519 B2 | 8/2017 | Demmer et al. |
| 9,731,138 B1 | 8/2017 | Stadler et al. |
| 9,789,319 B2 | 10/2017 | Sambelashvili |
| 9,808,628 B2 | 11/2017 | Sheldon et al. |
| 9,808,633 B2 | 11/2017 | Bonner et al. |
| 9,877,789 B2 | 1/2018 | Ghosh |
| 9,901,732 B2 | 2/2018 | Sommer et al. |
| 9,924,884 B2 | 3/2018 | Ghosh et al. |
| 10,004,467 B2 | 6/2018 | Lahm et al. |
| 10,039,305 B2 | 8/2018 | Asleson et al. |
| 10,064,567 B2 | 9/2018 | Ghosh et al. |
| 10,092,744 B2 | 10/2018 | Sommer et al. |
| 10,099,050 B2 | 10/2018 | Chen et al. |
| 10,166,396 B2 | 1/2019 | Schrock et al. |
| 10,251,555 B2 | 4/2019 | Ghosh et al. |
| 10,315,028 B2 | 6/2019 | Sommer et al. |
| 10,406,370 B1 | 9/2019 | Makharinsky |
| 10,456,581 B2 | 10/2019 | Liu et al. |
| 10,463,853 B2 | 11/2019 | Drake et al. |
| 10,478,627 B2 | 11/2019 | Muessig |
| 10,850,107 B2 | 12/2020 | Li et al. |
| 10,850,108 B2 | 12/2020 | Li et al. |
| 11,058,880 B2 | 7/2021 | Yang |
| 2001/0044619 A1 | 11/2001 | Altman |
| 2002/0026220 A1 | 2/2002 | Groenewegen et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0049476 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082652 A1 | 6/2002 | Wentkowski |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0169484 A1 | 11/2002 | Mathis et al. |
| 2002/0173830 A1 | 11/2002 | Starkweather et al. |
| 2002/0193846 A1 | 12/2002 | Pool et al. |
| 2003/0004549 A1 | 1/2003 | Hill et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0083702 A1 | 5/2003 | Stadler et al. |
| 2003/0088278 A1 | 5/2003 | Bardy et al. |
| 2003/0092995 A1 | 5/2003 | Thompson |
| 2003/0093122 A1 | 5/2003 | Vanhout |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2003/0199938 A1 | 10/2003 | Smits et al. |
| 2003/0204233 A1 | 10/2003 | Laske et al. |
| 2004/0024435 A1 | 2/2004 | Leckrone et al. |
| 2004/0064158 A1 | 4/2004 | Klein |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0116878 A1 | 6/2004 | Byrd et al. |
| 2004/0127959 A1 | 7/2004 | Amundson et al. |
| 2004/0127967 A1 | 7/2004 | Osypka |
| 2004/0133242 A1 | 7/2004 | Chapman et al. |

(56) References Cited

U.S. PATENT DOCUMENTS

| | | |
|---|---|---|
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0230236 A1 | 11/2004 | Struble et al. |
| 2004/0230283 A1 | 12/2004 | Prinzen et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0008210 A1 | 1/2005 | Evron et al. |
| 2005/0038477 A1 | 2/2005 | Kramer et al. |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0137629 A1 | 6/2005 | Dyjach et al. |
| 2005/0137632 A1 | 6/2005 | Ding |
| 2005/0137638 A1 | 6/2005 | Yonce et al. |
| 2005/0137671 A1 | 6/2005 | Liu |
| 2005/0149138 A1 | 7/2005 | Min et al. |
| 2005/0165466 A1* | 7/2005 | Morris ............. A61B 17/00234 607/116 |
| 2005/0182465 A1 | 8/2005 | Ness |
| 2005/0203410 A1 | 9/2005 | Jenkins |
| 2005/0277990 A1 | 12/2005 | Ostroff et al. |
| 2005/0283208 A1 | 12/2005 | Von Arx et al. |
| 2005/0288720 A1 | 12/2005 | Ross et al. |
| 2005/0288743 A1 | 12/2005 | Ahn et al. |
| 2006/0041300 A1 | 2/2006 | Zhang et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0074285 A1 | 4/2006 | Zarkh et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0161205 A1 | 7/2006 | Mitrani et al. |
| 2006/0161211 A1 | 7/2006 | Thompson |
| 2006/0200002 A1 | 9/2006 | Guenst |
| 2006/0206151 A1 | 9/2006 | Lu |
| 2006/0206153 A1 | 9/2006 | Libbus |
| 2006/0212079 A1 | 9/2006 | Routh et al. |
| 2006/0235478 A1 | 10/2006 | Van Gelder et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0247751 A1 | 11/2006 | Seifert |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0021767 A1* | 1/2007 | Breznock ......... A61B 17/00234 606/185 |
| 2007/0021813 A1 | 1/2007 | Sommer et al. |
| 2007/0027508 A1 | 2/2007 | Cowan |
| 2007/0049975 A1 | 3/2007 | Cates et al. |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jaconson |
| 2007/0135882 A1 | 6/2007 | Drasler et al. |
| 2007/0135883 A1 | 6/2007 | Drasler et al. |
| 2007/0150009 A1 | 6/2007 | Kveen |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0167758 A1 | 7/2007 | Costello |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0233216 A1 | 10/2007 | Liu |
| 2007/0239244 A1 | 10/2007 | Morgan et al. |
| 2007/0239248 A1 | 10/2007 | Hastings |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2007/0299475 A1 | 12/2007 | Levin et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0027488 A1 | 1/2008 | Coles |
| 2008/0058656 A1 | 3/2008 | Costello |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0082136 A1 | 4/2008 | Gaudiani |
| 2008/0103539 A1 | 5/2008 | Stegemann et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0183072 A1 | 7/2008 | Robertson et al. |
| 2008/0228234 A1 | 9/2008 | Stancer |
| 2008/0234771 A1 | 9/2008 | Chinchoy et al. |
| 2008/0242976 A1 | 10/2008 | Robertson |
| 2008/0243217 A1 | 10/2008 | Wildon |
| 2008/0269814 A1 | 10/2008 | Rosero |
| 2008/0269816 A1 | 10/2008 | Prakash et al. |
| 2008/0269823 A1 | 10/2008 | Burnes et al. |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288008 A1 | 11/2008 | Lee |
| 2008/0288039 A1 | 11/2008 | Reddy |
| 2008/0294208 A1 | 11/2008 | Willis et al. |
| 2008/0294210 A1 | 11/2008 | Rosero |
| 2008/0294229 A1 | 11/2008 | Friedman et al. |
| 2008/0306359 A1 | 12/2008 | Zdeblick et al. |
| 2008/0319500 A1 | 12/2008 | Zhu et al. |
| 2009/0018599 A1 | 1/2009 | Hastings et al. |
| 2009/0024180 A1 | 1/2009 | Kisker et al. |
| 2009/0036769 A1 | 2/2009 | Zdeblick |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0099619 A1 | 4/2009 | Lessmeier et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |

(56) References Cited

U.S. PATENT DOCUMENTS

| | | |
|---|---|---|
| 2009/0210024 A1 | 8/2009 | Jason |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0234412 A1 | 9/2009 | Sambelashvili |
| 2009/0234413 A1 | 9/2009 | Sambelashvili et al. |
| 2009/0234414 A1 | 9/2009 | Sambelashvili et al. |
| 2009/0234415 A1 | 9/2009 | Sambelashvili et al. |
| 2009/0248103 A1 | 10/2009 | Sambelashvili et al. |
| 2009/0259272 A1 | 10/2009 | Reddy et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0281590 A1 | 11/2009 | Maskara et al. |
| 2009/0299447 A1 | 12/2009 | Jensen et al. |
| 2009/0306732 A1 | 12/2009 | Rosenberg et al. |
| 2009/0326397 A1 | 12/2009 | Behzadi et al. |
| 2010/0013668 A1 | 1/2010 | Kantervik |
| 2010/0016911 A1 | 1/2010 | Willis et al. |
| 2010/0016914 A1 | 1/2010 | Mullen et al. |
| 2010/0016917 A1 | 1/2010 | Efimov et al. |
| 2010/0016918 A1 | 1/2010 | Mann |
| 2010/0023078 A1 | 1/2010 | Dong et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0063375 A1 | 3/2010 | Kassab et al. |
| 2010/0063562 A1 | 3/2010 | Cowan et al. |
| 2010/0065871 A1 | 3/2010 | Govari et al. |
| 2010/0069983 A1 | 3/2010 | Peacock, III et al. |
| 2010/0094250 A1 | 4/2010 | Gumm |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0114284 A1 | 5/2010 | Doerr |
| 2010/0125281 A1 | 5/2010 | Jacobson et al. |
| 2010/0152798 A1 | 6/2010 | Sanghera et al. |
| 2010/0152801 A1 | 6/2010 | Joh |
| 2010/0168761 A1 | 7/2010 | Kassab et al. |
| 2010/0168819 A1 | 7/2010 | Freeberg |
| 2010/0185250 A1 | 7/2010 | Rom |
| 2010/0198288 A1 | 8/2010 | Ostroff |
| 2010/0198291 A1 | 8/2010 | Sambelashvili et al. |
| 2010/0198304 A1 | 8/2010 | Wang |
| 2010/0204766 A1 | 8/2010 | Zdeblick et al. |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286541 A1 | 11/2010 | Musley et al. |
| 2010/0286626 A1 | 11/2010 | Petersen |
| 2010/0286744 A1 | 11/2010 | Echt et al. |
| 2010/0298841 A1 | 11/2010 | Prinzen et al. |
| 2010/0305451 A1 | 12/2010 | Kim et al. |
| 2010/0312309 A1 | 12/2010 | Harding |
| 2010/0318147 A1 | 12/2010 | Forslund |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0098562 A1 | 4/2011 | Salgo et al. |
| 2011/0106202 A1 | 5/2011 | Ding et al. |
| 2011/0112398 A1 | 5/2011 | Zarkh et al. |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184297 A1 | 7/2011 | Vitali et al. |
| 2011/0184491 A1 | 7/2011 | Kivi |
| 2011/0190835 A1 | 8/2011 | Brockway et al. |
| 2011/0190841 A1 | 8/2011 | Sambelashvili et al. |
| 2011/0196444 A1 | 8/2011 | Prakash et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0230922 A1 | 9/2011 | Fishel |
| 2011/0237967 A1 | 9/2011 | Moore et al. |
| 2011/0238102 A1 | 9/2011 | Gutfinger et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0029586 A1 | 2/2012 | Kumar |
| 2012/0035685 A1 | 2/2012 | Saha et al. |
| 2012/0041500 A1 | 2/2012 | Zhu |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078129 A1 | 3/2012 | Bailin |
| 2012/0078322 A1 | 3/2012 | Dal Molin et al. |
| 2012/0089198 A1 | 4/2012 | Ostroff |
| 2012/0089214 A1 | 4/2012 | Kroll et al. |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109235 A1 | 5/2012 | Sheldon et al. |
| 2012/0109236 A1 | 5/2012 | Jacobson et al. |
| 2012/0109244 A1 | 5/2012 | Anderson |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0179221 A1 | 7/2012 | Reddy et al. |
| 2012/0185008 A1 | 7/2012 | Zhou |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232478 A1 | 9/2012 | Haslinger |
| 2012/0232563 A1 | 9/2012 | Williams |
| 2012/0232565 A1 | 9/2012 | Kveen et al. |
| 2012/0245665 A1 | 9/2012 | Friedman et al. |
| 2012/0263218 A1 | 10/2012 | Dal Molin et al. |
| 2012/0271369 A1 | 10/2012 | Ollivier |
| 2012/0277600 A1 | 11/2012 | Greenhut |
| 2012/0277606 A1 | 11/2012 | Ellingson et al. |
| 2012/0277725 A1 | 11/2012 | Kassab |
| 2012/0283587 A1 | 11/2012 | Gosh et al. |
| 2012/0283795 A1 | 11/2012 | Stancer et al. |
| 2012/0283807 A1 | 11/2012 | Deterre et al. |
| 2012/0284003 A1 | 11/2012 | Gosh et al. |
| 2012/0290025 A1 | 11/2012 | Keimel |
| 2012/0296228 A1 | 11/2012 | Zhang et al. |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0013017 A1 | 1/2013 | Mullen et al. |
| 2013/0023975 A1 | 1/2013 | Locsin |

(56) References Cited

U.S. PATENT DOCUMENTS

| | | |
|---|---|---|
| 2013/0035748 A1 | 2/2013 | Bonner et al. |
| 2013/0041422 A1 | 2/2013 | Jacobson |
| 2013/0053906 A1 | 2/2013 | Ghosh et al. |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourg et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116739 A1 | 5/2013 | Brada et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0131750 A1 | 5/2013 | Stadler et al. |
| 2013/0131751 A1 | 5/2013 | Stadler et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0196703 A1 | 8/2013 | Masoud et al. |
| 2013/0197599 A1 | 8/2013 | Sambelashvili et al. |
| 2013/0197609 A1 | 8/2013 | Moore et al. |
| 2013/0231710 A1 | 9/2013 | Jacobson |
| 2013/0231728 A1 | 9/2013 | Ollivier |
| 2013/0238072 A1 | 9/2013 | Deterre et al. |
| 2013/0238073 A1 | 9/2013 | Makdissi et al. |
| 2013/0253342 A1 | 9/2013 | Griswold et al. |
| 2013/0253343 A1 | 9/2013 | Walfhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268017 A1 | 10/2013 | Zhang et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0138006 A1 | 11/2013 | Bornzin et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039591 A1 | 2/2014 | Drasler et al. |
| 2014/0043146 A1 | 2/2014 | Makdissi et al. |
| 2014/0046389 A1 | 2/2014 | Anderson |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0339570 A1 | 2/2014 | Carroll et al. |
| 2014/0067036 A1* | 3/2014 | Shuros ............. A61N 1/0573 606/129 |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0114173 A1 | 4/2014 | Bar-Tal et al. |
| 2014/0114372 A1 | 4/2014 | Ghosh et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172033 A1 | 6/2014 | Pei |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0323882 A1 | 10/2014 | Ghosh et al. |
| 2014/0323892 A1 | 10/2014 | Ghosh et al. |
| 2014/0330208 A1 | 11/2014 | Christie et al. |
| 2014/0330287 A1 | 11/2014 | Thompson-Nauman et al. |
| 2014/0330326 A1 | 11/2014 | Thompson-Nauman et al. |
| 2014/0358135 A1 | 12/2014 | Sambelashvili et al. |
| 2014/0371832 A1 | 12/2014 | Ghosh |
| 2014/0371833 A1 | 12/2014 | Ghosh et al. |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Foster et al. |
| 2015/0105836 A1 | 4/2015 | Bonner et al. |
| 2015/0142070 A1 | 5/2015 | Sambelashvili |
| 2015/0148697 A1 | 5/2015 | Burnes et al. |
| 2015/0149096 A1 | 5/2015 | Soykan |
| 2015/0157861 A1 | 6/2015 | Aghassian |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0238768 A1 | 8/2015 | Bornzin |
| 2015/0238769 A1 | 8/2015 | Demmer et al. |

(56) References Cited

U.S. PATENT DOCUMENTS

| | | | |
|---|---|---|---|
| 2015/0258312 A1* | 9/2015 | Tuseth | A61B 17/00234 604/8 |
| 2015/0258345 A1 | 9/2015 | Smith et al. | |
| 2015/0290468 A1 | 10/2015 | Zhang | |
| 2015/0297905 A1 | 10/2015 | Greenhut et al. | |
| 2015/0297907 A1 | 10/2015 | Zhang | |
| 2015/0305637 A1 | 10/2015 | Greenhut et al. | |
| 2015/0305638 A1 | 10/2015 | Zhang | |
| 2015/0305639 A1 | 10/2015 | Greenhut et al. | |
| 2015/0305640 A1 | 10/2015 | Reinke et al. | |
| 2015/0305641 A1 | 10/2015 | Stadler et al. | |
| 2015/0305642 A1 | 10/2015 | Reinke et al. | |
| 2015/0305695 A1 | 10/2015 | Lahm et al. | |
| 2015/0306374 A1 | 10/2015 | Seifert et al. | |
| 2015/0306375 A1 | 10/2015 | Marshall et al. | |
| 2015/0306406 A1 | 10/2015 | Crutchfield et al. | |
| 2015/0306407 A1 | 10/2015 | Crutchfield et al. | |
| 2015/0306408 A1 | 10/2015 | Greenhut et al. | |
| 2015/0321016 A1 | 11/2015 | O'Brien et al. | |
| 2015/0328459 A1 | 11/2015 | Chin et al. | |
| 2015/0335894 A1 | 11/2015 | Bornzin et al. | |
| 2016/0015287 A1 | 1/2016 | Anderson et al. | |
| 2016/0015322 A1 | 1/2016 | Anderson et al. | |
| 2016/0023000 A1 | 1/2016 | Cho et al. | |
| 2016/0030757 A1 | 2/2016 | Jacobson | |
| 2016/0033177 A1 | 2/2016 | Barot et al. | |
| 2016/0045738 A1 | 2/2016 | Ghosh et al. | |
| 2016/0045744 A1 | 2/2016 | Gillberg et al. | |
| 2016/0051821 A1 | 2/2016 | Sambelashvili et al. | |
| 2016/0059002 A1 | 3/2016 | Grubac et al. | |
| 2016/0067486 A1 | 3/2016 | Brown et al. | |
| 2016/0067487 A1 | 3/2016 | Demmer et al. | |
| 2016/0067490 A1 | 3/2016 | Carney et al. | |
| 2016/0110856 A1 | 4/2016 | Hoof et al. | |
| 2016/0114161 A1 | 4/2016 | Amblard et al. | |
| 2016/0121127 A1 | 5/2016 | Klimovitch et al. | |
| 2016/0121128 A1 | 5/2016 | Fishler et al. | |
| 2016/0121129 A1 | 5/2016 | Persson et al. | |
| 2016/0129239 A1 | 5/2016 | Anderson | |
| 2016/0129262 A1 | 5/2016 | Sheldon et al. | |
| 2016/0213919 A1 | 7/2016 | Suwito et al. | |
| 2016/0213937 A1 | 7/2016 | Reinke et al. | |
| 2016/0213939 A1 | 7/2016 | Carney et al. | |
| 2016/0228026 A1 | 8/2016 | Jackson | |
| 2016/0242887 A1 | 8/2016 | Watschke et al. | |
| 2016/0310733 A1 | 10/2016 | Sheldon et al. | |
| 2016/0317825 A1 | 11/2016 | Jacobson | |
| 2016/0361536 A1 | 12/2016 | Grubac et al. | |
| 2016/0367823 A1 | 12/2016 | Cowan et al. | |
| 2017/0014629 A1 | 1/2017 | Ghosh et al. | |
| 2017/0035315 A1 | 2/2017 | Jackson | |
| 2017/0043173 A1 | 2/2017 | Sharma et al. | |
| 2017/0043174 A1 | 2/2017 | Greenhut et al. | |
| 2017/0056670 A1 | 3/2017 | Sheldon et al. | |
| 2017/0182327 A1 | 6/2017 | Liu | |
| 2017/0189674 A1 | 7/2017 | Camps | |
| 2017/0189681 A1 | 7/2017 | Anderson | |
| 2017/0209689 A1 | 7/2017 | Chen | |
| 2017/0216575 A1 | 8/2017 | Asleson et al. | |
| 2017/0246461 A1 | 8/2017 | Ghosh | |
| 2017/0303840 A1 | 10/2017 | Stadler et al. | |
| 2017/0304624 A1 | 10/2017 | Friedman et al. | |
| 2017/0326369 A1 | 11/2017 | Koop et al. | |
| 2017/0326372 A1 | 11/2017 | Koop et al. | |
| 2017/0340885 A1 | 11/2017 | Sambelashvili | |
| 2018/0008829 A1 | 1/2018 | An et al. | |
| 2018/0021567 A1 | 1/2018 | An et al. | |
| 2018/0021581 A1 | 1/2018 | An et al. | |
| 2018/0021582 A1 | 1/2018 | An et al. | |
| 2018/0050208 A1 | 2/2018 | Shuros et al. | |
| 2018/0071539 A1 | 3/2018 | Hastings et al. | |
| 2018/0078773 A1 | 3/2018 | Thakur et al. | |
| 2018/0078779 A1 | 3/2018 | An et al. | |
| 2018/0117324 A1 | 5/2018 | Schilling et al. | |
| 2018/0140848 A1 | 5/2018 | Stahmann | |
| 2018/0178007 A1 | 6/2018 | Shuros et al. | |
| 2018/0185653 A1 | 7/2018 | Baru et al. | |
| 2018/0212451 A1 | 7/2018 | Schmidt et al. | |
| 2018/0256902 A1 | 9/2018 | Toy et al. | |
| 2018/0256904 A1 | 9/2018 | Li et al. | |
| 2018/0263522 A1 | 9/2018 | Ghosh et al. | |
| 2018/0264262 A1 | 9/2018 | Haasl et al. | |
| 2018/0264272 A1 | 9/2018 | Haasl et al. | |
| 2018/0264273 A1 | 9/2018 | Haasl et al. | |
| 2018/0264274 A1 | 9/2018 | Haasl et al. | |
| 2018/0272121 A1 | 9/2018 | Yankelson | |
| 2018/0280686 A1 | 10/2018 | Shuros et al. | |
| 2018/0326215 A1 | 11/2018 | Ghosh | |
| 2019/0029090 A1 | 1/2019 | Ikehara et al. | |
| 2019/0030346 A1 | 1/2019 | Li | |
| 2019/0038906 A1 | 2/2019 | Koop et al. | |
| 2019/0083779 A1 | 3/2019 | Yang et al. | |
| 2019/0083800 A1 | 3/2019 | Yang et al. | |
| 2019/0083801 A1 | 3/2019 | Yang et al. | |
| 2019/0111270 A1 | 4/2019 | Zhou | |
| 2019/0126050 A1 | 5/2019 | Shuros et al. | |
| 2019/0134412 A1 | 5/2019 | Shuros et al. | |
| 2019/0151666 A1 | 5/2019 | Bonnet | |
| 2019/0192034 A1 | 6/2019 | Ghosh | |
| 2019/0192860 A1 | 6/2019 | Ghosh et al. | |
| 2019/0192863 A1 | 6/2019 | Koop et al. | |
| 2019/0261876 A1 | 8/2019 | Ghosh et al. | |
| 2019/0269926 A1 | 9/2019 | Ghosh | |
| 2019/0269929 A1* | 9/2019 | Bjorklund | A61N 1/0573 |
| 2019/0290905 A1 | 9/2019 | Yang et al. | |
| 2019/0290909 A1 | 9/2019 | Ghosh | |
| 2019/0290910 A1 | 9/2019 | Yang | |
| 2019/0290915 A1 | 9/2019 | Yang | |
| 2019/0298903 A1 | 10/2019 | Gillberg et al. | |
| 2019/0298990 A1 | 10/2019 | De Kock et al. | |
| 2019/0314636 A1 | 10/2019 | Shuros et al. | |
| 2019/0351236 A1 | 11/2019 | Koop | |
| 2020/0016418 A1 | 1/2020 | Makharinsky | |
| 2020/0069949 A1 | 3/2020 | Ghosh | |
| 2020/0095061 A1 | 3/2020 | Ghosh | |
| 2020/0139130 A1 | 5/2020 | Li et al. | |
| 2020/0197705 A1 | 6/2020 | Drake | |
| 2020/0197706 A1 | 6/2020 | Grenz | |
| 2020/0206511 A1 | 7/2020 | Goedeke et al. | |
| 2020/0261725 A1 | 8/2020 | Yang | |
| 2020/0261731 A1 | 8/2020 | Ghosh | |
| 2020/0261734 A1 | 8/2020 | Yang | |
| 2020/0306529 A1 | 10/2020 | Asleson | |
| 2020/0306546 A1 | 10/2020 | Ghosh | |
| 2020/0338336 A1 | 10/2020 | Makharinsky et al. | |
| 2020/0338356 A1 | 10/2020 | Anderson | |
| 2020/0352470 A1 | 11/2020 | Ghosh | |
| 2021/0060340 A1 | 3/2021 | Klepfer et al. | |
| 2021/0085986 A1 | 3/2021 | Li et al. | |
| 2021/0106227 A1 | 4/2021 | Ghosh | |
| 2021/0106245 A1 | 4/2021 | Ghosh | |
| 2021/0106839 A1 | 4/2021 | Hine | |
| 2021/0128925 A1 | 5/2021 | Ghosh | |
| 2021/0204879 A1 | 7/2021 | Gelfman | |
| 2021/0228892 A1 | 7/2021 | Kornet et al. | |
| 2021/0298658 A1 | 9/2021 | Ghosh | |
| 2021/0307670 A1 | 10/2021 | Ghosh | |
| 2021/0308458 A1 | 10/2021 | Ghosh | |
| 2022/0202486 A1 | 6/2022 | Morales | |

FOREIGN PATENT DOCUMENTS

| | | |
|---|---|---|
| AU | 2014203793 | 7/2014 |
| CN | 202933393 | 5/2013 |
| EP | 0362611 | 4/1990 |
| EP | 0459 239 A2 | 12/1991 |
| EP | 0 728 497 A2 | 8/1996 |
| EP | 1 541 191 | 6/2005 |
| EP | 1 702 648 | 9/2006 |
| EP | 1 904 166 | 6/2011 |
| EP | 2 452 721 | 5/2012 |
| EP | 2 471 452 | 7/2012 |
| EP | 2 662 113 A2 | 11/2013 |
| EP | 1 703 944 | 7/2015 |

(56) References Cited

FOREIGN PATENT DOCUMENTS

| | | |
|---|---|---|
| JP | 2005245215 | 9/2005 |
| WO | WO 95/00202 | 1/1995 |
| WO | WO 96/36134 | 11/1996 |
| WO | WO 97/24981 | 7/1997 |
| WO | WO 02/22206 | 3/2002 |
| WO | WO 03/092800 | 11/2003 |
| WO | 2005007228 A1 | 1/2005 |
| WO | WO 2005/000206 A2 | 1/2005 |
| WO | WO 2005/042089 | 5/2005 |
| WO | WO 2006/086435 A2 | 8/2006 |
| WO | WO 2006/113659 | 10/2006 |
| WO | WO 2006/116595 A2 | 11/2006 |
| WO | WO 2007/073435 | 6/2007 |
| WO | WO 2007/075974 A2 | 7/2007 |
| WO | WO 2008/0422887 A2 | 4/2008 |
| WO | WO 2008/058265 A2 | 5/2008 |
| WO | WO 2008/064682 A2 | 6/2008 |
| WO | WO 2009/006531 | 1/2009 |
| WO | WO 2013/080038 A2 | 6/2013 |
| WO | WO 2013/098644 A2 | 7/2013 |
| WO | WO 2015/081221 | 6/2015 |
| WO | WO 2015/193047 A2 | 12/2015 |
| WO | WO 2016/011042 | 1/2016 |
| WO | WO 2016/077099 | 5/2016 |
| WO | 2016110856 A9 | 7/2016 |
| WO | WO 2016/110856 | 7/2016 |
| WO | WO 2016/171891 | 10/2016 |
| WO | WO 2017/075193 | 5/2017 |
| WO | WO 2018/009569 | 1/2018 |
| WO | WO 2018/017226 | 1/2018 |
| WO | WO 2018/017361 | 1/2018 |
| WO | WO 2018/035343 | 2/2018 |
| WO | WO 2018/081519 | 5/2018 |
| WO | WO 2020/226754 | 11/2020 |
| WO | WO 2021/123271 | 6/2021 |

OTHER PUBLICATIONS (PCT/US2019/061601) Written Opinion of the International Searching Authority and the International Search Report, dated Mar. 11, 2020, 7 pages.
U.S. Appl. No. 17/361,721, filed Jun. 29, 2021, Klepfer et al.
U.S. Appl. No. 17/385,609, filed Jul. 26, 2021, Whitman et al.
http://www.isrctn.com/ISRCTN47824547, public posting published Aug. 2019.
Abed et al., "Obesity results in progressive atrial structural and electrical remodeling: Implications for atrial fibrillation," *Heart Rhythm Society*, Jan. 2013; 10(1):90-100.
Adragão et al., "Ablation of pulmonary vein foci for the treatment of atrial fibrillation; percutaneous electroanatomical guided approach," *Europace*, Oct. 2002; 4(4):391-9.
Aliot et al., "Arrhythmia detection by dual-chamber implantable cardioverter defibrillators: A review of current algorithms," *Europace*, Jul. 2004; 6(4):273-86.
Amirahmadi et al., "Ventricular Tachycardia Caused by Mesothelial Cyst", *Indian Pacing and Electrophysiology Journal*, 2013; 13(1):43-44.
Ammirabile et al., "Pitx2 confers left morphological, molecular, and functional identity to the sinus venosus myocardium," *Cardiovasc Res.*, Feb. 2012; 93(2):291-301.
Anderson et al., "Left bundle branch block and the evolving role of QRS morphology in selection of patients for cardiac resynchronization", Journal of Interventional Cardio Electrophysiology, vol. 52, No. 3. Aug. 20, 2018, pp. 353-374.
Anfinsen, "Non-pharmacological Treatment of Atrial Fibrillation," *Indian Pacing and Electrophysiology Journal*, Jan. 2002; 2(1):4-14.
Anné et al., "Ablation of post-surgical intra-atrial reentrant Tachycardia," *European Heart Journal*, 2002; 23:169-1616.
Arenal et al., "Dominant frequency differences in atrial fibrillation patients with and without left ventricular systolic dysfunction," *Europace*, Apr. 2009; 11(4):450-457.
Arriagada et al., "Predictors of arrhythmia recurrence in patients with lone atrial fibrillation," *Europace*, Jan. 2008; 10(1):9-14.
Asirvatham et al., "Cardiac Anatomic Considerations in Pediatric Electrophysiology," *Indian Pacing and Electrophysiology Journal*, Apr. 2008; 8(Suppl 1):S75-S91.
Asirvatham et al., "Intramyocardial Pacing and Sensing for the Enhancement of Cardiac Stimulation and Sensing Specificity," *Pacing Clin. Electrophysiol.*, Jun. 2007; 30(6):748-754.
Asirvatham et al., "Letter to the Editor," *J Cardiovasc Electrophysiol.*, Mar. 2010; 21(3): E77.
Balmer et al., "Long-term follow up of children with congenital complete atrioventricular block and the impact of pacemaker therapy," *Europace*, Oct. 2002; 4(4):345-349.
Barold et al., "Conventional and biventricular pacing in patients with first-degree atrioventricular block," *Europace*, Oct. 2012; 14(10): 1414-9.
Barold et al., "The effect of hyperkalaemia on cardiac rhythm devices," *Europace*, Apr. 2014; 16(4):467-76.
Bayrak et al., "Added value of transoesophageal echocardiography during transseptal puncture performed by inexperienced operators," *Europace*, May 2012; 14(5):661-5.
Bergau et al., "Measurement of Left Atrial Pressure is a Good Predictor of Freedom From Atrial Fibrillation," *Indian Pacing and Electrophysiology Journal*, Jul. 2014; 14(4): 181-93.
Bernstein et al., "The revised NASPE/BPEG generic code for antibradycardia, adaptive-rate, and multisite pacing. North American Society of Pacing and Electrophysiology/British Pacing and Electrophysiology Group," *Pacing Clin Electrophysiol.*, Feb. 2002; 25(2):260-4.
Bito et al., "Early exercise training after myocardial infarction prevents contractile but not electrical remodeling or hypertrophy," *Cardiovascular Research*, Apr. 2010; 86(1):72-81.
Bollmann et al., "Analysis of surface electrocardiograms in atrial fibrillation: techniques, research, and clinical applications," *Europace*, Nov. 2006; 8(11):911-926.
Bortone et al., "Evidence for an incomplete mitral isthmus block after failed ablation of a left postero-inferior concealed accessory pathway," *Europace*, Jun. 2006; 8(6):434-7.
Boulos et al., "Electroanatomical mapping and radiofrequency ablation of an accessory pathway associated with a large aneurysm of the coronary sinus," *Europace*, Nov. 2004; 6(6):608-12.
Brembilla-Perrot et al., "Incidence and prognostic significance of spontaneous and inducible antidromic tachycardia," *Europace*, Jun. 2013; 15(6):871-876.
Buber et al., "Morphological features of the P-waves at surface electrocardiogram as surrogate to mechanical function of the left atrium following a successful modified maze procedure," *Europace*, Apr. 2014; 16(4):578-86.
Burashnikov et al., "Late-phase 3 EAD. A unique mechanism contributing to initiation of atrial fibrillation," *Pacing Clin Electrophysiol.*, Mar. 2006; 29(3):290-5.
Burashnikov et al., "Atrial-selective inhibition of sodium-channel current by Wenxin Keli is effective in suppressing atrial fibrillation," *Heart Rhythm*, Jan. 2012; 9(1):125-31.
Calvo et al., "Efficacy of circumferential pulmonary vein ablation of atrial fibrillation in endurance athletes," *Europace*, Jan. 2010; 12(1):30-6.
Can et al., ""Atrial torsades de pointes" Induced by Low-Energy Shock From Implantable-Cardioverter Defibrillator," *Indian Pacing and Electrophysiology Journal*, Sep. 2013; 13(5):194-199.
Carroz et al., "Pseudo-pacemaker syndrome in a young woman with first-degree atrio-ventricular block," *Europace*, Apr. 2010; 12(4):594-596.
Catanchin et al., "Wolff-Parkinson-White syndrome with an unroofed coronary sinus without persistent left superior vena cava treated with catheter cryoablation," *Indian Pacing and Electrophysiology Journal*, Aug. 2008; 8(3): 227-233.
Cazeau et al., "Cardiac resynchronization therapy," *Europace*, Sep. 2004; 5 Suppl 1:S42-8.
Cerqueira et al., "Standardized myocardial segmentation and nomenclature for tomographic imaging of the heart. A statement for healthcare professionals from the Cardiac Imaging Committee of

(56) References Cited

OTHER PUBLICATIONS the Council on Clinical Cardiology of the American Heart Association," *Circulation*, Jan. 29, 2002; 105(4):539-42.
Chandra et al., "Evaluation of KCB-328, a new IKr blocking antiarrhythmic agent in pacing induced canine atrial fibrillation," *Europace*, Sep. 2004; 6(5):384-91.
Chang et al., "Electrophysiological characteristics and catheter ablation in patients with paroxysmal supraventricular tachycardia and paroxysmal atrial fibrillation," *J Cardiovasc Electrophysiol.*, Apr. 2008; 19(4):367-73.
Charron et al., "A familial form of conduction defect related to a mutation in the PRKAG2 gene," *Europace*, Aug. 2007; 9(8):597-600.
Chou et al., "Effects of SEA0400 on Arrhythmogenicity in a Langendorff-Perfused 1-Month Myocardial Infarction Rabbit Model," *Pacing Clin Electrophysiol.*, May 2013; 36(5):596-606.
Ciploetta et al., "Posterior Coronary Vein as the Substrate for an Epicardial Accessory Pathway," *Indian Pacing and Electrophysiology Journal*, Aug. 2013; 13(4): 142-7.
Climent et al., "Effects of endocardial microwave energy ablation," *Indian Pacing and Electrophysiology Journal*, Jul. 2005; 5(3):233-43.
Comtois et al., "Of circles and spirals: bridging the gap between the leading circle and spiral wave concepts of cardiac reentry," *Europace*, Sep. 2005; 7 Suppl 2:10-20.
Crick et al., "Anatomy of the pig heart: comparisons with normal human cardiac structure," *J. Anat.*, 1998, 193:105-119.
Daoulah et al., "Unintended Harm and Benefit of the Implantable Defibrillator in an Unfortunate 19-Year-Old Male: Featuring a Sequence of Rare Life-threatening Complications of Cardiac Procedures," *Indian Pacing and Electrophysiology Journal*, Aug. 2013; 13(4):151-6.
De Mattia et al., "Paroxysmal atrial fibrillation triggered by a monomorphic ventricular couplet in a patient with acute coronary syndrome," *Indian Pacing and Electrophysiology Journal*, Jan. 2012; 12(1): 19-23.
DeSimone et al., "New approach to cardiac resynchronization therapy: CRT without left ventricular lead," Apr. 25, 2014, 2 pages.
De Sisti et al., "Electrophysiological determinants of atrial fibrillation in sinus node dysfunction despite atrial pacing," *Europace*, Oct. 2000; 2(4):304-11.
De Voogt et al., "Electrical characteristics of low atrial septum pacing compared with right atrial appendage pacing," *Europace*, Jan. 2005; 7(1):60-6.
De Voogt et al., "A technique of lead insertion for low atrial septal pacing," *Pacing Clin Electrophysiol.*, Jul. 2005; 28(7):639-46.
Dizon et al. "Real-time stroke volume measurements for the optimization of cardiac resynchronization therapy parameters," *Europace*, Sep. 2010; 12(9):1270-1274.
Duckett et al., "Relationship between endocardial activation sequences defined by high-density mapping to early septal contraction (septal flash) in patients with left bundle branch block undergoing cardiac resynchronization therapy," *Europace*, Jan. 2012; 14(1):99-106.
Eksik et al., "Influence of atrioventricular nodal reentrant tachycardia ablation on right to left inter-atrial conduction," *Indian Pacing and Electrophysiology Journal*, Oct. 2005; 5(4):279-88.
Fiala et al., "Left Atrial Voltage during Atrial Fibrillation in Paroxysmal and Persistent Atrial Fibrillation Patients," *PACE*, May 2010; 33(5):541-548.
Fragakis et al., "Acute beta-adrenoceptor blockade improves efficacy of ibutilide in conversion of atrial fibrillation with a rapid ventricular rate," *Europace*, Jan. 2009; 11(1):70-4.
Frogoudaki et al., "Pacing for adult patients with left atrial isomerism: efficacy and technical considerations," *Europace*, Apr. 2003; 5(2):189-193.
Ganapathy et al., "Implantable Device to Monitor Cardiac Activity with Sternal Wires," *Pacing Clin. Electrophysiol.*, Dec. 2014; Epub Aug. 24, 2014; 37(12): 1630-40.
Geddes, "Accuracy limitations of chronaxie values," *IEEE Trans Biomed Eng.*, Jan. 2004; 51(1):176-81.

Gertz et al., "The impact of mitral regurgitation on patients undergoing catheter ablation of atrial fibrillation," *Europace*, Aug. 2011; 13(8):1127-32.
Girmatsion et al., "Changes in microRNA-1 expression and IK1 up-regulation in human atrial fibrillation," *Heart Rhythm*, Dec. 2009; 6(12):1802-9.
Goette et al., "Acute atrial tachyarrhythmia induces angiotensin II type 1 receptor-mediated oxidative stress and microvascular flow abnormalities in the ventricles," *European Heart Journal*, Jun. 2009; 30(11):1411-20.
Goette et al., "Electrophysiological effects of angiotensin II. Part I: signal transduction and basic electrophysiological mechanisms," *Europace*, Feb. 2008; 10(2):238-41.
Gómez et al., "Nitric oxide inhibits Kv4.3 and human cardiac transient outward potassium current (Ito1)," *Cardiovasc Res.*, Dec. 2008; 80(3):375-84.
Gros et al., "Connexin 30 is expressed in the mouse sino-atrial node and modulates heart rate," *Cardiovascular Research*, Jan. 2010; 85(1):45-55.
Guenther et al., "Substernal Lead Implantation: A Novel Option to Manage OFT Failure in S-ICD patients," *Clinical Research Cardiology*, Feb. 2015; Epub Oct. 2, 2014; 104(2): 189-91.
Guillem et al., "Noninvasive mapping of human atrial fibrillation," *J Cardiovasc Electrophysiol.*, May 2009; 20(5):507-513.
Hachisuka et al., "Development and Performance Analysis of an Intra-Body Communication Device," The $12^{th}$ International Conference on Solid State Sensors, Actuators and Microsystems, vol. 4.3, pp. 1722-1725, 2003.
Hakacova et al., "Septal atrial pacing for the prevention of atrial fibrillation," *Europace*, 2007; 9:1124-1128.
Hasan et al., "Safety, efficacy, and performance of implanted recycled cardiac rhythm management (CRM) devices in underprivileged patients," *Pacing Clin Electrophysiol.*, Jun. 2011; 34(6):653-8.
Hawkins, "Epicardial Wireless Pacemaker for Improved Left Ventricular Reynchronization (Conceptual Design)", Dec. 2010, A Thesis presented to the Faculty of California Polytechnic State University, San Luis Obispo, 57 pp.
He et al., "Three-dimensional cardiac electrical imaging from intracavity recordings," *IEEE Trans Biomed Eng.*, Aug. 2007; 54(8): 1454-60.
Heist et al., "Direct visualization of epicardial structures and ablation utilizing a visually guided laser balloon catheter: preliminary findings," *J Cardiovasc Electrophysiol.*, Jul. 2011; 22(7):808-12.
Henz et al., "Synchronous Ventricular Pacing without Crossing the Tricuspid Valve or Entering the Coronary Sinus-Preliminary Results," *J Cardiovasc Electrophysiol.*, Dec. 2009; 20(12):1391-1397.
Hiippala et al., "Automatic Atrial Threshold Measurement and Adjustment in Pediatric Patients," *Pacing Clin Electrophysiol.*, Mar. 2010; 33(3):309-13.
Ho, "Letter to the Editor" *J Cardiovasc Electrophysiol.*, Mar. 2010; 21(3): E76.
Höijer et al., "Improved cardiac function and quality of life following upgrade to dual chamber pacing after long-term ventricular stimulation," *European Heart Journal*, Mar. 2002; 23(6):490-497.
Huang et al., "A Novel Pacing Strategy With Low and Stable Output: Pacing the Left Bundle Branch Immediately Beyond the Conduction Block," *Can J Cardiol.*, Dec. 2007; Epub Sep. 22, 2017; 33(12):1736.e1-1736.e.
Ishigaki et al., "Prevention of immediate recurrence of atrial fibrillation with low-dose landiolol after radiofrequency catheter ablation," *Journal of Arrhythmia*, Oct. 2015; 31(5):279-285.
Israel, "The role of pacing mode in the development of atrial fibrillation," *Europace*, Feb. 2006; 8(2):89-95.
Janion et al., "Dispersion of P wave duration and P wave vector in patients with atrial septal aneurysm," *Europace*, Jul. 2007; 9(7):471-4.
Kabra et al., "Recent Trends in Imaging for Atrial Fibrillation Ablation," *Indian Pacing and Electrophysiology Journal*, 2010; 10(5):215-227.

(56) References Cited

OTHER PUBLICATIONS

Kalbfleisch et al., "Catheter Ablation with Radiofrequency Energy: Biophysical Aspects and Clinical Applications," *Journal of Cardiovascular Electrophysiology*, Oct. 2008; 3(2):173-186.

Katritsis et al., "Classification and differential diagnosis of atrioventricular nodal re-entrant tachycardia," *Europace*, Jan. 2006; 8(1):29-36.

Katritsis et al., "Anatomically left-sided septal slow pathway ablation in dextrocardia and situs inversus totalis," *Europace*, Aug. 2008; 10(8): 1004-5.

Khairy et al., "Cardiac Arrhythmias In Congenital Heart Diseases," *Indian Pacing and Electrophysiology Journal*, Nov.-Dec. 2009; 9(6): 299-317.

Kimmel et al., "Single-site ventricular and biventricular pacing: investigation of latest depolarization strategy," *Europace*, Dec. 2007; 9(12):1163-1170.

Klimek-Piotrowska et al., "Geometry of Koch's Triangle", *Eurospace*, 19, 2017, pp. 452-457.

Knackstedt et al., "Electro-anatomic mapping systems in arrhythmias," *Europace*, Nov. 2008; 10 Suppl 3:iii28-ii34.

Kobayashi et al., "Successful Ablation of Antero-septal Accessory Pathway in the Non-Coronary Cusp in a Child," *Indian Pacing and Electrophysiology Journal*, 2012; 12(3):124-130.

Kojodjojo et al., "4:2:1 conduction of an AF initiating trigger," *Indian Pacing and Electrophysiology Journal*, Nov. 2015; 15(5):255-8.

Kołodzińska et al., "Differences in encapsulating lead tissue in patients who underwent transvenous lead removal," *Europace*, Jul. 2012; 14(7):994-1001.

Konecny et al., "Synchronous intra-myocardial ventricular pacing without crossing the tricuspid valve or entering the coronary sinus," *Cardiovascular Revascularization Medicine*, 2013; 14:137-138.

Kriatselis et al., "Ectopic atrial tachycardias with early activation at His site: radiofrequency ablation through a retrograde approach," *Europace*, Jun. 2008; 10(6):698-704.

Lalu et al., "Ischaemia-reperfusion injury activates matrix metalloproteinases in the human heart," *Eur Heart J.*, Jan. 2005; 26(1):27-35.

Laske et al., "Excitation of the Intrinsic Conduction System Through His and Interventricular Septal Pacing," *Pacing Clin. Electrophysiol.*, Apr. 2006; 29(4):397-405.

Leclercq, "Problems and troubleshooting in regular follow-up of patients with cardiac resynchronization therapy," *Europace*, Nov. 2009; 11 Suppl 5:v66-71.

Lee et al., "An unusual atrial tachycardia in a patient with Friedreich ataxia," *Europace*, Nov. 2011; 13(11):1660-1.

Lee et al., "Blunted Proarrhythmic Effect of Nicorandil in a Langendorff-Perfused Phase-2 Myocardial Infarction Rabbit Model," *Pacing Clin Electrophysiol.*, Feb. 2013; 36(2):142-51.

Lemay et al., "Spatial dynamics of atrial activity assessed by the vectorcardiogram: from sinus rhythm to atrial fibrillation," *Europace*, Nov. 2007; 9 Suppl 6:vi109-18.

Levy et al., "Does the mechanism of action of biatrial pacing for atrial fibrillation involve changes in cardiac haemodynamics? Assessment by Doppler echocardiography and natriuretic peptide measurements," *Europace*, Apr. 2000; 2(2):127-35.

Lewalter et al., "Comparison of spontaneous atrial fibrillation electrogram potentials to the P wave electrogram amplitude in dual chamber pacing with unipolar atrial sensing," *Europace*, Apr. 2000; 2(2): 136-40.

Liakopoulos et al., "Sequential deformation and physiological considerations in unipolar right and left ventricular pacing," *European Journal of Cardio-thoracic Surgery*, Apr. 1, 2006; 29S1:S188-197.

Lian et al., "Computer modeling of ventricular rhythm during atrial fibrillation and ventricular pacing," *IEEE Transactions on Biomedical Engineering*, Aug. 2006; 53(8):1512-1520.

Lim et al., "Right ventricular lead implantation facilitated by a guiding sheath in a patient with severe chamber dilatation with tricuspid regurgitation," *Indian Pacing and Electrophysiology Journal*, Sep. 2011; 11(5):156-8.

Lim et al., "Coupled pacing improves left ventricular function during simulated atrial fibrillation without mechanical dyssynchrony," *Europace*, Mar. 2010; 12(3):430-6.

Lou et al., "Tachy-brady arrhythmias: The critical role of adenosine-induced sinoatrial conduction block in post-tachycardia pauses," *Heart Rhythm.*, Jan. 2013; 10(1):110-8.

Lutomsky et al., "Catheter ablation of paroxysmal atrial fibrillation improves cardiac function: a prospective study on the impact of atrial fibrillation ablation on left ventricular function assessed by magnetic resonance imaging," *Europace*, May 2008; 10(5):593-9.

Macedo et al., "Septal accessory pathway: anatomy, causes for difficulty, and an approach to ablation," *Indian Pacing and Electrophysiology Journal*, Jul. 2010; 10(7):292-309.

Mafi-Rad et al., "Feasibility and Acute Hemodynamic Effect of Left Ventricular Septal Pacing by Transvenous Approach Through the Interventricular Septum," *Circ Arrhythm Electrophysoil.*, Mar. 2016; 9(3): e003344.

Mani et al., "Dual Atrioventricular Nodal Pathways Physiology: A Review of Relevant Anatomy, Electrophysiology, and Electrocardiogramanifestations," *Indian Pacing and Electrophysiology Journal*, Jan. 2014; 14(1): 12-25.

Manios et al., "Effects of successful cardioversion of persistent atrial fibrillation on right ventricular refractoriness and repolarization," *Europace*, Jan. 2005; 7(1):34-9.

Manolis et al., "Prevention of atrial fibrillation by inter-atrial septum pacing guided by electrophysiological testing, in patients with delayed interatrial conduction," *Europace*, Apr. 2002; 4(2): 165-174.

Marino et al., "Inappropriate mode switching clarified by using a chest radiograph," *Journal of Arrhythmia*, Aug. 2015; 31(4):246-248.

Markowitz et al., "Time course and predictors of autonomic dysfunction after ablation of the slow atrioventricular nodal pathway," *Pacing Clin Electrophysiol.*, Dec. 2004; 27(12):1638-43.

Marshall et al., "The effects of temperature on cardiac pacing thresholds," *Pacing Clin Electrophysiol.*, Jul. 2010; 33(7):826-833.

McSharry et al., "A Dynamical Model for Generating Synthetic Electrocardiogram Signals," *IEEE Transactions on Biomedical Engineering*, Mar. 2003; 50(3):289-294.

Meijler et al., "Scaling of Atrioventricular Transmission in Mammalian Species: An Evolutionary Riddle!," *Journal of Cardiovascular Electrophysiology*, Aug. 2002; 13(8):826-830.

Meiltz et al., "Permanent form of junctional reciprocating tachycardia in adults: peculiar features and results of radiofrequency catheter ablation," *Europace*, Jan. 2006; 8(1):21-8.

Mellin et al., "Transient reduction in myocardial free oxygen radical levels is involved in the improved cardiac function and structure after long-term allopurinol treatment initiated in established chronic heart failure," *Eur Heart J.*, Aug. 2005; 26(15):1544-50.

Mestan et al., "The influence of fluid and diuretic administration on the index of atrial contribution in sequentially paced patients," *Europace*, Apr. 2006; 8(4):273-8.

Metin et al., "Assessment of the P Wave Dispersion and Duration in Elite Women Basketball Players," *Indian Pacing and Electrophysiology Journal*, 2010; 10(1): 11- 20.

Mills et al., "Left Ventricular Septal and Left Ventricular Apical Pacing Chronically Maintain Cardiac Contractile Coordination, Pump Function and Efficiency," *Circ Arrhythm Electrophysoil.*, Oct. 2009; 2(5):571-579.

Mitchell et al., "How do atrial pacing algorithms prevent atrial arrhythmias?" *Europace*, Jul. 2004; 6(4):351-62.

Mirzoyev et al., "Embryology of the Conduction System for the Electrophysiologist," *Indian Pacing and Electrophysiology Journal*, 2010; 10(8):329-338.

Modre et al., "Noninvasive Myocardial Activation Time Imaging: A Novel Inverse Algorithm Applied to Clinical ECG Mapping Data," *IEE Transactions on Biomedical Engineering*, Oct. 2002; 49(10):1153-1161.

Montgomery et al., "Measurement of diffuse ventricular fibrosis with myocardial T1 in patients with atrial fibrillation," *J Arrhythm.*, Feb. 2016; 32(1):51-6.

(56) References Cited

OTHER PUBLICATIONS

Mulpuru et al., "Synchronous ventricular pacing with direct capture of the atrioventricular conduction system: Functional anatomy, terminology, and challenges," *Heart Rhythm*, Nov. 2016; Epub Aug. 3, 2016; 13(11):2237- 2246.
Musa et al., "Inhibition of Platelet-Derived Growth Factor-AB Signaling Prevents Electromechanical Remodeling of Adult Atrial Myocytes that Contact Myofibroblasts," *Heart Rhythm*, Jul. 2013; 10(7): 1044-1051.
Nagy et al., "Wnt-11 signalling controls ventricular myocardium development by patterning N-cadherin and B-catenin expression," *Cardiovascular Research*, Jan. 2010; 85(1):100-9.
Namboodiri et al., "Electrophysiological features of atrial flutter in cardiac sarcoidosis: a report of two cases," *Indian Pacing and Electrophysiology Journal*, Nov. 2012; 12(6):284-9.
Nanthakumar et al., "Assessment of accessory pathway and atrial refractoriness by transesophageal and intracardiac atrial stimulation: An analysis of methodological agreement," *Europace*, Jan. 1999; 1(1):55-62.
Neto et al., "Temporary atrial pacing in the prevention of postoperative atrial fibrillation," *Pacing Clin Electrophysiol.*, Jan. 2007; 30(Suppl 1):S79-83.
Nishijima et al., "Tetrahydrobiopterin depletion and NOS2 uncoupling contribute to heart failure-induced alterations in atrial electrophysiology," *Cardiovasc Res.*, Jul. 2011; 91(1):71-9.
Niwano et al., "Effect of oral L-type calcium channel blocker on repetitive paroxysmal atrial fibrillation: spectral analysis of fibrillation waves in the Holter monitoring," *Europace*, Dec. 2007; 9(12):1209-1215.
Okumura et al., "Effects of a high-fat diet on the electrical properties of porcine atria," *Journal of Arrhythmia*, Dec. 2015; 31(6):352-358.
Olesen et al., "Mutations in sodium channel B-subunit SCN3B are associated with early-onset lone atrial fibrillation," *Cardiovascular Research*, Mar. 2011; 89(4): 786-93.
Ozcan Cetin et al., "Coronary Sinus Diameter to Inferior Vena Cava Diameter Ratio in the Diagnosis of Cardiac Tamponade A Novel Approach", J Comput Assist Tomogr, vol. 44, No. 4, Jul./Aug. 2020, pp. 599-604.
Ozmen et al., "P wave dispersion is increased in pulmonary stenosis," *Indian Pacing and Electrophysiology Journal*, Jan. 2006; 6(1):25-30.
Packer et al., "New generation of electro-anatomic mapping: Full intracardiac image integration," *Europace*, Nov. 2008; 10 Suppl 3:iii35-41.
Page et al., "Ischemic ventricular tachycardia presenting as a narrow complex tachycardia," *Indian Pacing and Electrophysiology Journal*, Jul. 2014; 14(4):203- 210.
Pakarinen et al., "Pre-implant determinants of adequate long-term function of single lead VDD pacemakers," *Europace*, Apr. 2002; 4:137-141.
Patel et al., "Atrial Fibrillation after Cardiac Surgery: Where are we now?" *Indian Pacing and Electrophysiology Journal*, Oct.-Dec. 2008; 8(4):281-291.
Patel et al., "Successful ablation of a left-sided accessory pathway in a patient with coronary sinus atresia and arteriovenous fistula: clinical and developmental insights," *Indian Pacing and Electrophysiology Journal*, Mar. 2011; 11(2):43-49.
Peschar et al., "Left Ventricular Septal and Apex Pacing for Optimal Pump Function in Canine Hearts," *J Am Coll Cardiol.*, Apr. 2, 2003; 41(7): 1218-1226.
Physiological Research Laboratories, Final Report for an Acute Study for Model 6426-85 AV Septal Leads, Feb. 1996.
Porciani et al., "Interatrial septum pacing avoids the adverse effect of interatrial delay in biventricular pacing: an echo-Doppler evaluation," *Europace*, Jul. 2002; 4(3):317-324.
Potse et al., "A Comparison of Monodomain and Bidomain Reaction-Diffusion Models for Action Potential Propagation in the Human Heart," *IEEE Transactions on Biomedical Engineering*, Dec. 2006; 53(12 Pt 1):2425-35.
Prystowsky et al., "Case studies with the experts: management decisions in atrial fibrillation," *J Cardiovasc Electrophysiol.*, Feb. 2008; 19(Suppl. 1):S1-12.
Prystowsky, "The history of atrial fibrillation: the last 100 years," *J Cardiovasc Electrophysiol*, Jun. 2008; 19(6):575-582.
Pytkowski et al., "Paroxysmal atrial fibrillation is associated with increased intra-atrial conduction delay," *Europace*, Dec. 2008; 10(12):1415-20.
Qu et al., "Dynamics and cardiac arrhythmias," *J Cardiovasc Electrophysiol.*, Sep. 2006; 17(9):1042-9.
Ravens et al., "Role of potassium currents in cardiac arrhythmias," *Europace*, Oct. 2008; 10(10):1133-7.
Ricci et al., Efficacy of a dual chamber defibrillator with atrial antitachycardia functions in treating spontaneous atrial tachyarrhythmias in patients with life-threatening ventricular tachyarrhythmias, *European Heart Journal*, Sep. 2002; 23(18):1471-9.
Roberts-Thomson et al., "Focal atrial tachycardia II: management," *Pacing Clin Electrophysiol.*, Jul. 2006; 29(7):769-78.
Rossi et al., "Endocardial vagal atrioventricular node stimulation in humans: reproducibility on 18-month follow-up," *Europace*, Dec. 2010; 12(12): 1719-24.
Rouzet et al., "Contraction delay of the RV outflow tract in patients with Brugada syndrome is dependent on the spontaneous ST-segment elevation pattern," *Heart Rhythm*, Dec. 2011; 8(12):1905-12.
Russo et al., "Atrial Fibrillation and Beta Thalassemia Major: The Predictive Role of the 12-lead Electrocardiogram Analysis," *Indian Pacing and Electrophysiology Journal*, May 2014; 14(3):121-32.
Ryu et al., "Simultaneous Electrical and Mechanical Mapping Using 3D Cardiac Mapping System: Novel Approach for Optimal Cardiac Resynchronization Therapy," Journal of Cardiovascular Electrophysiology, Feb. 2010, 21(2): 219-22.
Sairaku et al., "Prediction of sinus node dysfunction in patients with persistent atrial flutter using the flutter cycle length," *Europace*, Mar. 2012; 14(3):380-7.
Santini et al., "Immediate and long-term atrial sensing stability in single-lead VDD pacing depends on right atrial dimensions," *Europace*, Oct. 2001; 3(4):324-31.
Saremi et al., "Cardiac Conduction System: Delineation of Anatomic Landmarks With Multidetector CT," *Indian Pacing and Electrophysiology Journal*, Nov. 2009; 9(6):318-33.
Savelieva et al., "Anti-arrhythmic drug therapy for atrial fibrillation: current anti-arrhythmic drugs, investigational agents, and innovative approaches," *Europace*, Jun. 2008; 10(6):647-665.
Schmidt et al., "Navigated DENSE strain imaging for post-radiofrequency ablation lesion assessment in the swine left atria," *Europace*, Jan. 2014; 16(1): 133-41.
Schoonderwoerd et al., "Rapid Pacing Results in Changes in Atrial but not in Ventricular Refractoriness," *Pacing Clin Electrophysiol.*, Mar. 2002; 25(3):287-90.
Schoonderwoerd et al., "Atrial natriuretic peptides during experimental atrial tachycardia: role of developing tachycardiomyopathy," *J Cardiovasc Electrophysiol.*, Aug. 2004; 15(8):927-32.
Schoonderwoerd et al., "Atrial ultrastructural changes during experimental atrial tachycardia depend on high ventricular rate," *J Cardiovasc Electrophysiol.*, Oct. 2004; 15(10):1167-74.
Sedmera, "Function and form in the developing cardiovascular system," *Cardiovasc Res.*, Jul. 2011; 91(2):252-9.
Severi et al., "Alterations of atrial electrophysiology induced by electrolyte variations: combined computational and P-wave analysis," *Europace*, Jun. 2010; 12(6):842-9.
Seyedi et al., "A Survey on Intrabody Communications for Body Area Network Application," IEEE Transactions on Biomedical Engineering, vol. 60(8): 2067-2079, 2013.
Shah et al., "Stable atrial sensing on long-term follow up of VDD pacemakers," *Indian Pacing and Electrophysiology Journal*, Oct. 2006; 6(4): 189-93.
Shenthar et al., "Permanent pacemaker implantation in a patient with situs solitus, dextrocardia, and corrected transposition of the great arteries using a novel angiographic technique," *Journal of Arrhythmia*, Apr. 2014; 30(2):134-138.

(56) References Cited

OTHER PUBLICATIONS

Shenthar et al., "Transvenous permanent pacemaker implantation in dextrocardia: technique, challenges, outcome, and a brief review of literature," Europace, Sep. 2014; 16(9):1327-33.
Shirayama, "Role of atrial fibrillation threshold evaluation on guiding treatment," Indian Pacing and Electrophysiology Journal, Oct. 2003; 3(4):224-230.
Sperzel et al., "Intraoperative Characterization of Interventricular Mechanical Dyssynchrony Using Electroanatomic Mapping System—A Feasibility Study," Journal of Interventional Cardiac Electrophysiology, Nov. 2012, 35(2): 189-96.
Spickler et al., "Totally Self-Contained Intracardiac Pacemaker," Journal of Electrocardiology, vol. 3(3&4): 324-331, 1970.
Sreeram et al., "Indications for Electrophysiology Study in children," Indian Pacing and Electrophysiology Journal, Apr.-Jun. 2008; 8(Suppl. 1):S36-S54.
Stockburger et al., "Optimization of cardiac resynchronization guided by Doppler echocardiography: haemodynamic improvement and intraindividual variability with different pacing configurations and atrioventricular delays," Europace, Oct. 2006; 8(10):881-6.
Stroobandt et al., "Prediction of Wenckebach Behavior and Block Response in DDD Pacemakers," Pacing Clin Electrophysiol., Jun. 2006; 9(6):1040-6.
Suenari et al., "Idiopathic left ventricular tachycardia with dual electrocardiogram morphologies in a single patient," Europace, Apr. 2010; 12(4):592-4.
Sweeney et al., "Analysis of Ventricular Activation Using Surface Electrocardiogramadict Left Ventricular Reverse Volumetric Remodeling During Cardiac Resynchronization Therapy," Circulation, Feb. 9, 2010, 121(5): 626-34.
Tan et al., "Electrocardiogramevidence of ventricular repolarization remodelling during atrial fibrillation," Europace, Jan. 2008; 10(1):99-104.
Taramasco et al., "Internal low-energy cardioversion: a therapeutic option for restoring sinus rhythm in chronic atrial fibrillation after failure of external cardioversion," Europace, Jul. 1999; 1(3):179-82.
Testa et al., "Rate-control or rhythm-control: where do we stand?" Indian Pacing and Electrophysiology Journal, Oct. 2005; 5(4):296-304.
Thejus et al., "N-terminal Pro-Brain Natriuretic Peptide And Atrial Fibrillation," Indian Pacing and Electrophysiology Journal, Jan. 2009; 9(1): 1-4.
Thornton et al., "Magnetic Assisted Navigation in Electrophysiology and Cardiac Resynchronisation: A Review," Indian Pacing and Electrophysiology Journal, Oct. 2006; 6(4):202-13.
Tilz et al., "In vivo left-ventricular contact force analysis: comparison of antegrade transseptal with retrograde transaortic mapping strategies and correlation of impedance and electrical amplitude with contact force," Europace, Sep. 2014; 16(9):1387-95.
Tomaske et al., "Do daily threshold trend fluctuations of epicardial leads correlate with pacing and sensing characteristics in paediatric patients?" Europace, Aug. 2007; 9(8):662-668.
Tomioka et al., "The effect of ventricular sequential contraction on helical heart during pacing: high septal pacing versus biventricular pacing," European Journal of Cardio-thoracic Surgery, Apr. 1, 2006; 29S1:S198-206.
Tournoux et al., "A 'Regularly Irregular' tachycardia: What is the diagnosis?" Europace, Dec. 2008; 10(12): 1445-6.
Traykov et al., "Electrogram analysis at the His bundle region and the proximal coronary sinus as a tool to predict left atrial origin of focal atrial tachycardias," Europace, Jul. 2011; 13(7):1022-7.
Trudel et al., "Simulation of QRST integral maps with a membrane-based computer heart model employing parallel processing," IEEE Trans Biomed Eng., Aug. 2004; 51(8): 1319-29.
Tse et al., "Cardiac dynamics: Alternans and arrhythmogenesis," Journal of Arrhythmia, Oct. 2016; 32(5):411-417.
Tse, "Mechanisms of cardiac arrhythmias," Journal of Arrhythmia, Apr. 2016; 32(2):75-81.

Ueda et al., "Outcomes of single- or dual-chamber implantable cardioverter defibrillator systems in Japanese patients," Journal of Arrhythmia, Apr. 2016; 32(2): 89-94.
Van Dam et al., "Volume conductor effects involved in the genesis of the P wave," Europace, Sep. 2005; 7 Suppl 2:30-8.
Van den Berg et al., "Depletion of atrial natriuretic peptide during longstanding atrial fibrillation," Europace, Sep. 2004; 6(5):433-7.
Van Deursen, et al., "Vectorcardiography as a Tool for Easy Optimization of Cardiac Resynchronization Therapy in Canine LBBB Hearts," Circulation Arrhythmia and Electrophysiology, Jun. 1, 2012, 5(3): 544-52.
Van Opstal et al., "Paradoxical increase of stimulus to atrium interval despite His-bundle capture during para-Hisian pacing," Europace, Dec. 2009; 11(12):1702-4.
Veenhuyzen et al., "Diagnostic pacing maneuvers for supraventricular tachycardia: part 1," Pacing Clin Electrophysiol., Jun. 2011; 34(6):767-82.
Veenhuyzen et al., "Diagnostic pacing maneuvers for supraventricular tachycardias: part 2," Pacing Clin Electrophysiol., Jun. 2012; 35(6): 757-69.
Veenhuyzen et al., "Principles of Entrainment: Diagnostic Utility for Supraventricular Tachycardia," Indian Pacing and Electrophysiology Journal, 2008; 8(1):51-65.
Verbrugge et al., "Revisiting diastolic filling time as mechanistic insight for response to cardiac resynchronization therapy," Europace, Dec. 2013; 15(12):1747-56.
Verrier et al., "Mechanisms of ranolazine's dual protection against atrial and ventricular fibrillation," Europace, Mar. 2013; 15(3):317-324.
Verrijcken et al., "Pacemaker-mediated tachycardia with varying cycle length: what is the mechanism?" Europace, Oct. 2009; 11(10): 1400-2.
Villani et al., "Reproducibility of internal atrial defibrillation threshold in paroxysmal and persistent atrial fibrillation," Europace, Jul. 2004; 6(4):267-72.
Violi et al., "Antioxidants for prevention of atrial fibrillation: a potentially useful future therapeutic approach? A review of the literature and meta-analysis," Europace, Aug. 2014; 16(8):1107-1116.
Weber et al., "Adenosine sensitive focal atrial tachycardia originating from the non-coronary aortic cusp," Europace, Jun. 2009; 11(6):823-6.
Weber et al., "Open-irrigated laser catheter ablation: relationship between the level of energy, myocardial thickness, and collateral damages in a dog model," Europace, Jan. 2014; 16(1): 142-8.
Wegmoller, "Intra-Body Communication for Biomedical Sensor Networks," Diss. ETH, No. 17323, 1-173, 2007.
Wei et al., "Comparative simulation of excitation and body surface electrocardiogram with isotropic and anisotropic computer heart models," IEEE Trans Biomed Eng., Apr. 1995; 42(4):343-57.
Weijs et al., "Clinical and echocardiographic correlates of intra-atrial conduction delay," Europace, Dec. 2011; 13(12):1681-7.
Weiss et al., "The influence of fibre orientation, extracted from different segments of the human left ventricle, on the activation and repolarization sequence: a simulation study," Europace, Nov. 2007; 9(Suppl. 6): vi96-vi104.
Wetzel et al., "A stepwise mapping approach for localization and ablation of ectopic right, left, and septal atrial foci using electroanatomic mapping," European Heart Journal, Sep. 2002; 23(17):1387-1393.
Wlodarska et al., "Thromboembolic complications in patients with arrhythmogenic right ventricular dysplasia/cardiomyopathy," Europace, Aug. 2006; 8(8):596-600.
Wong et al., "A review of mitral isthmus ablation," Indian Pacing and Electrophysiology Journal, 2012; 12(4):152-170.
Wu et al., "Acute and long-term outcome after catheter ablation of supraventricular tachycardia in patients after the Mustard or Senning operation for D-transposition of the great arteries," Europace, Jun. 2013; 15(6): 886-91.
Xia et al., "Asymmetric dimethylarginine concentration and early recurrence of atrial fibrillation after electrical cardioversion," Pacing Clin Electrophysiol., Aug. 2008; 31(8):1036-40.

(56) References Cited

OTHER PUBLICATIONS

Yamazaki et al., "Acute Regional Left Atrial Ischemia Causes Acceleration of Atrial Drivers during Atrial Fibrillation," *Heart Rhythm*, Jun. 2013; 10(6):901-9.

Yang et al., "Focal atrial tachycardia originating from the distal portion of the left atrial appendage: Characteristics and long-term outcomes of radiofrequency ablation," *Europace*, Feb. 2012; 14(2):254-60.

Yiginer et al., "Advanced Age, Female Gender and Delay in Pacemaker Implantation May Cause TdP in Patients With Complete Atrioventricular Block," *Indian Pacing and Electrophysiology Journal*, Oct. 2010; 10(10):454-63.

Yoon et al., "Measurement of thoracic current flow in pigs for the study of defibrillation and cardioversion," *IEEE Transactions on Biomedical Engineering*, Oct. 2003; 50(10):1167-1773.

Yuan et al., "Recording monophasic action potentials using a platinum-electrode ablation catheter," *Europace*, Oct. 2000; 2(4):312-9.

Yusuf et al., "5-Hydroxytryptamine and Atrial Fibrillation: How Significant is This Piece in the Puzzle?" *J Cardiovasc Electrophysiol.*, Feb. 2003; 14(2):209-14.

Zaugg et al., "Current concepts on ventricular fibrillation: a vicious circle of cardiomyocyte calcium overload in the initiation, maintenance, and termination of ventricular fibrillation," *Indian Pacing and Electrophysiology Journal*, Apr. 2004; 4(2): 85-92.

Zhang et al., "Acute atrial arrhythmogenicity and altered Ca(2+) homeostasis in murine RyR2-P2328S hearts," *Cardiovascular Research*, Mar. 2011; 89(4): 794-804.

Zoghi et al., "Electrical stunning and hibernation: suggestion of new terms for short- and long-term cardiac memory," *Europace*, Sep. 2004; 6(5):418-24.

Zografos et al., "Inhibition of the renin-angiotensin system for prevention of atrial fibrillation," *Pacing Clin Electrophysiol.*, Oct. 2010; 33(10):1270-85.

(PCT/US2014/036782) PCT Notification of Transmittal of the International Search Report and the Written Opinion of the International Searching Authority, dated Aug. 22, 2014, 11 pages.

International Search Report and Written Opinion for Application No. PCT/US2017/047378, 8 pages, dated Dec. 6, 2017.

(PCT/US2018/050988) PCT Notification of Transmittal of the International Search Report and the Written Opinion of the International Searching Authority, dated Nov. 14, 2018, 11 pages.

(PCT/US2018/050993) PCT Notification of Transmittal of the International Search Report and the Written Opinion of the International Searching Authority, dated Nov. 16, 2018, 7 pages.

(PCT/US2019/023642) PCT Notification of Transmittal of the International Search Report and the Written Opinion of the International Searching Authority, dated Jun. 28, 2019, 14 pages.

(PCT/US2019/023645) PCT Notification of Transmittal of the International Search Report and the Written Opinion of the International Searching Authority, dated Sep. 4, 2019, 14 pages.

(PCT/US2019/023646) PCT Notification of Transmittal of the International Search Report and the Written Opinion of the International Searching Authority, dated Aug. 19, 2019, 15 pages.

(PCT/1019/057352) PCT Notification of Transmittal of the International Search Report and the Written Opinion of the International Searching Authority, dated Nov. 27, 2019, 123 pages.

International Search Report and Written Opinion dated Apr. 2, 2020 from PCT Application No. PCT/2019/067858, 14 pages.

International Search Report and Written Opinion for PCT Application No. PCT/US2020/019200 dated May 29, 2020, 9 pages.

International Search Report and Written Opinion for Application No. PCT/US2020/023525, 10 pages, dated Jul. 9, 2020.

International Search Report and Written Opinion for Application No. PCT/US2020/047802, 9 pages, dated Nov. 19, 2020.

International Search Report and Written Opinion from PCT Application No. PCT/US2020/058627 dated Jan. 28, 2021, 9 pages.

International Search Report and Written Opinion from PCT Application No. PCT/US2020/062466, dated Jan. 27, 2021, 15 pages.

International Search Report and Written Opinion from PCT Application No. PCT/US2021/015226, dated Apr. 9, 2021, 14 pages.

International Search Report and Written Opinion from PCT Application No. PCT/US2021/033046, dated Aug. 9, 2021, 16 pages.

International Preliminary Report on Patentability from PCT Application No. PCT/US2019/023645, dated Oct. 8, 2020, 7 pages.

International Preliminary Report on Patentability from PCT Application No. PCT/US2019/023636, dated Oct. 8, 2020, 9 pages.

International Search Report and Written Opinion from PCT Application No. PCT/US2019/023636, dated Aug. 19, 2019, 15 pages.

International Preliminary Report on Patentability from PCT/US2019/023642, dated Oct. 8, 2020, 9 pages.

International Search Report and Written Opinion from PCT Application No. PCT/I019/058186, dated Jan. 3, 2020, 17 pages.

International Preliminary Report on Patentability from PCT/I019/058186, dated Apr. 8, 2021, 9 pages.

International Preliminary Report on Patentability from PCT/I019/057352, dated Mar. 11, 2021, 10 pages.

International Search Report and Written Opinion from PCT Application No. PCT/US2019/0567858, dated Apr. 2, 2020, 14 pages.

International Preliminary Report on Patentability from PCT/US2019/067858, dated Jul. 1, 2021, 8 pages.

International Search Report and Written Opinion from PCT Application No. PCT/US2021/012260, dated Apr. 7, 2021, 15 pages.

International Search Report and Written Opinion from PCT Application No. PCT/US2021/024652, dated Jul. 6, 2021, 18 pages.

International Search Report and Written Opinion from PCT Application No. PCT/US2021/025149, dated Jun. 30, 2021, 13 pages.

International Search Report and Written Opinion from PCT Application No. PCT/US2021/025151, dated Jun. 30, 2021, 13 pages.

International Search Report and Written Opinion from PCT Application No. PCT/US2021/040994, dated Oct. 25, 2021, 11 pages.

\* cited by examiner

VFA DELIVERY SYSTEMS AND METHODS

The present technology is generally related to devices, systems, and methods for delivering implantable medical devices.

The cardiac conduction system includes the sinus atrial (SA) node, the atrioventricular (AV) node, the bundle of His, bundle branches and Purkinje fibers. A heartbeat is initiated in the SA node, which may be described as the natural "pacemaker" of the heart. An electrical impulse arising from the SA node causes the atrial myocardium to contract. The electrical impulse, or electrical pulse or signal, is conducted to the ventricles via the AV node which inherently delays the conduction to allow the atria to stop contracting before the ventricles begin contracting thereby providing proper AV synchrony. The electrical impulse is conducted from the AV node to the ventricular myocardium via the bundle of His, bundle branches, and Purkinje fibers.

Patients with a conduction system abnormality, such as poor AV node conduction or poor SA node function, may receive an implantable medical device (IMD), such as a pacemaker, to restore a more normal heart rhythm and AV synchrony. Some types of IMDs, such as cardiac pacemakers, implantable cardioverter defibrillators (ICDs), or cardiac resynchronization therapy (CRT) devices, provide therapeutic electrical stimulation to a heart of a patient via electrodes on one or more implantable endocardial, epicardial, or coronary venous leads that are positioned in or adjacent to the heart. The therapeutic electrical stimulation may be delivered to the heart in the form of pulses or shocks for pacing, cardioversion, or defibrillation. In some cases, an IMD may sense intrinsic depolarizations of the heart, and control the delivery of therapeutic stimulation to the heart based on the sensing.

Delivery of therapeutic electrical stimulation to the heart can be useful in addressing cardiac conditions such as ventricular dyssynchrony that may occur in patients. Ventricular dyssynchrony may be described as a lack of synchrony or a difference in the timing of contractions in the right and left ventricles of the heart. Significant differences in the timing of contractions can reduce cardiac efficiency. CRT, delivered by an IMD to the heart, may enhance cardiac output by resynchronizing the electromechanical activity of the ventricles of the heart. CRT may include "triple-chamber pacing" when pacing the right atrium, right ventricle, and left ventricle.

Cardiac arrhythmias may be treated by delivering electrical shock therapy for cardioverting or defibrillating the heart in addition to cardiac pacing, for example, from an ICD, which may sense a patient's heart rhythm and classify the rhythm according to an arrhythmia detection scheme in order to detect episodes of tachycardia or fibrillation. Arrhythmias detected may include ventricular tachycardia (VT), fast ventricular tachycardia (FVT), ventricular fibrillation (VF), atrial tachycardia (AT) and atrial fibrillation (AT). Anti-tachycardia pacing (ATP) can be used to treat ventricular tachycardia (VT) to terminate substantially many monomorphic fast rhythms.

Dual chamber medical devices are available that include a transvenous atrial lead carrying electrodes that may be placed in the right atrium and a transvenous ventricular lead carrying electrodes that may be placed in the right ventricle via the right atrium. The dual chamber medical device itself is generally implanted in a subcutaneous pocket, and the transvenous leads are tunneled to the subcutaneous pocket. A dual chamber medical device may sense atrial electrical signals and ventricular electrical signals and can provide both atrial pacing and ventricular pacing as needed to promote a normal heart rhythm and AV synchrony. Some dual chamber medical devices can treat both atrial and ventricular arrhythmias.

Intracardiac medical devices, such as a leadless pacemaker, have been introduced or proposed for implantation entirely within a patient's heart, eliminating the need for transvenous leads. A leadless pacemaker may include one or more electrodes on its outer housing to deliver therapeutic electrical signals and/or sense intrinsic depolarizations of the heart. Intracardiac medical devices may provide cardiac therapy functionality, such as sensing and pacing, within a single-chamber of the patient's heart. Single-chamber intracardiac devices may also treat either atrial or ventricular arrhythmias or fibrillation. Some leadless pacemakers are not intracardiac and may be positioned outside of the heart and, in some examples, may be anchored to a wall of the heart via a fixation mechanism.

In some patients, single-chamber devices may adequately address the patient's needs. However, single-chamber devices capable of only single-chamber sensing and therapy may not fully address cardiac conduction disease or abnormalities in all patients, for example, those with some forms of AV dyssynchrony or tachycardia. Dual chamber sensing and/or pacing functions, in addition to ICD functionality in some cases, may be used to restore more normal heart rhythms.

SUMMARY

The techniques of this disclosure generally relate to devices, systems, and methods for delivering implantable medical devices for ventricular-from-atrial (VfA) cardiac therapy, such as single-chamber or multiple chamber pacing (e.g., dual- or triple-chamber pacing), atrioventricular synchronous pacing, asynchronous pacing, triggered pacing, cardiac resynchronization pacing, or tachycardia-related therapy. A VfA device may be implanted in the right atrium (RA) with an electrode extending from the right atrium into the left ventricular myocardium. In particular, the present disclosure provides a technique to deliver and implant a medical device in the triangle of Koch region in the right atrium. Various devices may be used to identify the general location of the triangle of Koch region, which may be described as a potential implantation site. A flexible leed, or another probe, may be advanced to the potential implantation site and used to identify a precise location for implantation of a medical device, such as an electrode, leadlet, lead, or intracardiac device. In some embodiments, the VfA device may include a tissue-piercing electrode or left-ventricular electrode. Advantageously, in one or more embodiments, the techniques of this disclosure may be used to precisely deliver one or more VfA devices to an implantation site for VfA cardiac therapy. In particular, the techniques of the present disclosure may be used to implant a device to provide synchronous pacing to patients with dyssynchrony, as well as provide dual chamber pacing for bradycardia patients with moderate heart failure.

In one aspect, the present disclosure provides a method for delivering a medical device. The method includes locating a potential implantation site in the triangle of Koch region in the right atrium of a patient's heart. The method also includes attaching a fixation sheath to the right-atrial endocardium in the potential implantation site. The method includes implanting the medical device over a guide wire at the potential implantation site.

In another aspect, the present disclosure provides a medical device delivery system. The system includes a fixation sheath having a fixation element attachable to a right-atrial endocardium in the triangle of Koch region in the right atrium of a patient's heart. The system also includes a steerable element configured to steer the fixation sheath. The system includes a flexible needle at least partially disposable in a lumen of the fixation sheath. The system further includes a guide wire at least partially disposable in the lumen of the fixation sheath.

In another aspect, the present disclosure provides an implantable medical device including an intracardiac housing and a leadlet coupled to the intracardiac housing. The device also includes a plurality of electrodes coupled to the intracardiac housing, the leadlet, or both. The plurality of electrodes includes a left-ventricular electrode implantable from the triangle of Koch region of the right atrium through the right-atrial endocardium and central fibrous body to deliver cardiac therapy to or sense electrical activity of the left ventricle in the basal and/or septal region of the left ventricular myocardium of a patient's heart. The plurality of electrodes also includes a right-atrial electrode positionable within the right atrium to deliver cardiac therapy to or sense electrical activity of the right atrium of the patient's heart. The system includes a therapy delivery circuit operably coupled to the plurality of electrodes to deliver cardiac therapy to the patient's heart, and a sensing circuit operably coupled to the plurality of electrodes to sense electrical activity of the patient's heart. The system further includes a controller having processing circuitry operably coupled to the therapy delivery circuit and the sensing circuit. The controller is configured to monitor electrical activity of the right atrium using the right-atrial electrode, the left ventricle using the left-ventricular electrode, or both. The controller is also configured to deliver cardiac therapy based on the monitored electrical activities using at least one of the plurality of electrodes.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

FIG. 26A shows that the lateral image is 90 degrees lateral and 25 degrees cranial. The valve plane is shown by the curve of the catheter in the CS. FIG. 26B shows a dorsal-ventral (DV) view of the heart showing an almost perpendicular view of the valve plane. The angles are 0 degrees lateral and 25 degrees cranial.

FIG. 27A shows a lateral view. FIG. 27B shows a DV view. The direction of the needle is not apical enough in the lateral and not aimed at the aorta in the DV view. The flexcath and/or helix is within the CS ostium shown by the crossing of the middle cardiac vein (MCV) sheath and CS sheaths.

FIG. 28A is a lateral view. FIG. 28B is a DV view.

FIG. 29A is a lateral view. FIG. 29B is a DV view.

FIG. 30A is a lateral view. FIG. 30B is a DV view.

FIG. 32A is a lateral view. FIG. 32B is a DV view.

FIG. 33A shows that the lateral image is 90 degrees lateral and 25 degrees cranial. The valve plane is shown by the curve of the catheter in the CS lining up with the aortic valve. FIG. 33B shows a DV view of the heart shown an almost perpendicular view of the valve plane. The angles are 0 degrees lateral and 25 degrees caudal. The aortic valve is in the middle of the LV.

FIG. 34A is a lateral view. FIG. 34B is a DV view.

FIG. 35A is a lateral view. The direction of the needle is slightly apical of the valve plane. FIG. 35B is a DV view. The direction of the needle is toward the aorta, while the tip of the flexcath is far from the CS.

FIG. 36A is a lateral view. FIG. 36B is a DV view.

FIG. 37A is a lateral view. FIG. 37B is a DV view.

FIG. 38A is a lateral view. FIG. 38B is a DV view.

FIG. 39A is a lateral view. FIG. 39B is a DV view.

FIG. 40A is a lateral view. The lead courses somewhat apical, and the wire is in the LV. FIG. 40B is a DV view. The lead courses toward the aorta.

FIG. 41A is a lateral view. FIG. 41B is a DV view.

FIG. 42A is a lateral view. FIG. 42B is a DV view.

FIG. 43A is a lateral view. FIG. 43B is a DV view.

FIG. 44A is a lateral view. FIG. 44B is a DV view.

DETAILED DESCRIPTION

Figure 1:
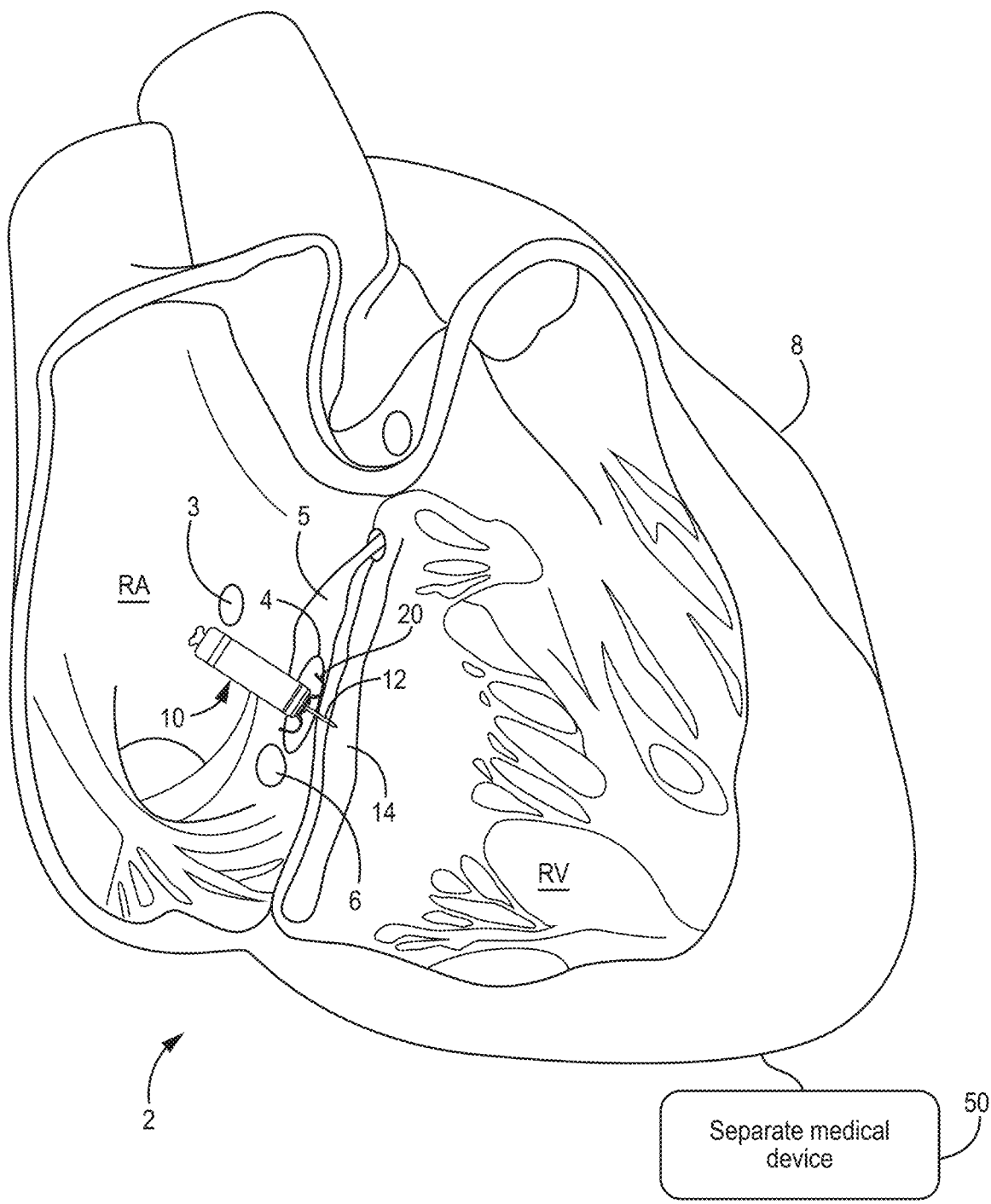
FIG. 1 is a conceptual diagram of an illustrative cardiac therapy system including an intracardiac medical device implanted in a patient's heart and a separate medical device positioned outside of the patient's heart for use with, e.g., the illustrative methods of FIGS. 16-20.

The techniques of this disclosure generally relate to devices, systems, and methods for delivering implantable medical devices for ventricular-from-atrial (VfA) cardiac therapy, such as single-chamber or multiple chamber pacing (e.g., dual- or triple-chamber pacing), atrioventricular synchronous pacing, asynchronous pacing, triggered pacing, cardiac resynchronization pacing, or tachycardia-related therapy. In some embodiments, various techniques described herein may also be applied to His bundle pacing applications. Although reference is made herein to implantable medical devices, such as a pacemaker or ICD, the methods and processes may be used with any medical devices, systems, or methods related to a patient's heart. Various other applications will become apparent to one of skill in the art having the benefit of the present disclosure.

It may be beneficial to provide an implantable medical device that is free of transvenous leads (e.g., a leadless device). It may also be beneficial to provide an implantable medical device capable of being used for various cardiac therapies, such as single or multiple chamber pacing (e.g., dual- or triple-chamber pacing), atrioventricular synchronous pacing, asynchronous pacing, triggered pacing, cardiac resynchronization pacing, or tachycardia-related therapy. Further, it may be beneficial to provide a technique for delivering a medical device to the triangle of Koch region in the right atrium in an accurate and precise manner to facilitate pacing the endocardium and/or the His bundle conduction system.

The present disclosure provides an implantable medical device including a tissue-piercing electrode and optionally a right-atrial electrode and/or a right-atrial motion detector. The implantable medical device may be a VfA device implanted from the right atrium into the left ventricular myocardium. The implantable medical device may be used in adaptive cardiac therapy, for example, that adapts pacing delays based on at least a measured heartrate. Physiological response measurements may be taken, and the VfA device may be configured to deliver cardiac therapy based on the physiological response information. In particular, the VfA device may be configured to adapt pacing therapy based on different heartrates, for example, by determining and delivering pacing therapy with an optimal atrioventricular (AV) pacing delay. Advantageously, in one or more embodiments, the techniques of this disclosure may be used to calibrate or deliver pacing therapy without using monitored electrical activity of the right ventricle of the patient's heart.

The tissue-piercing electrode may be implanted in the basal and/or septal region of the left ventricular myocardium of the patient's heart from the triangle of Koch region of the right atrium through the right-atrial endocardium and central fibrous body. In a leadless implantable medical device, the tissue-piercing electrode may leadlessly extend from a distal end region of a housing of the device, and the right-atrial electrode may be leadlessly coupled to the housing (e.g., part of or positioned on the exterior of the housing). The right-atrial motion detector may be within the implantable medical device. In a leaded implantable medical device, one or more of the electrodes may be coupled to the housing using an implantable lead. When the device is implanted, the electrodes may be used to sense electrical activity in one or more atria and/or ventricles of a patient's heart. The motion detector may be used to sense mechanical activity in one or more atria and/or ventricles of the patient's heart. In particular, the activity of the right atrium and the left ventricle may be monitored and, optionally, the activity of the right ventricle may be monitored. The electrodes may be used to deliver cardiac therapy, such as single-chamber pacing for atrial fibrillation, atrioventricular synchronous pacing for bradycardia, asynchronous pacing, triggered pacing, cardiac resynchronization pacing for ventricular dyssynchrony, anti-tachycardia pacing, or shock therapy. Shock therapy may be initiated by the implantable medical device. A separate medical device, such as an extravascular ICD, which may also be implanted, may be in operative communication with the implantable medical device and may deliver an electrical shock in response to a trigger, such as a signaling pulse (e.g., triggering, signaling, or distinctive electrical pulse) provided by the device.

The present disclosure also provides a technique to deliver and implant a medical device in the triangle of Koch region in the right atrium. Various devices may be used to identify the general location of the triangle of Koch region, which may be described as a potential implantation site. A flexible leed, or another probe, may be advanced to the potential implantation site and used to identify a precise location for implantation of a medical device, such as an electrode, leadlet, lead, or intracardiac device. In particular, the techniques of the present disclosure may be used to implant a device to provide synchronous pacing to patients with dyssynchrony, as well as provide dual chamber pacing for bradycardia patients with moderate heart failure.

FIGS. 1-4 show examples of various cardiac therapy systems that may be implanted using, for example, the methods shown in FIGS. 16-20 to deliver a medical device to an implantation site. Although the present disclosure describes leadless and leaded implantable medical devices, reference is first made to FIG. 1, which shows a conceptual diagram of a cardiac therapy system 2 including an intracardiac medical device 10 that may be configured for single or dual chamber therapy and implanted in a patient's heart 8. In some embodiments, the device 10 may be configured for single-chamber pacing and may, for example, switch between single-chamber and multiple-chamber pacing (e.g., dual- or triple-chamber pacing). As used herein, "intracardiac" refers to a device configured to be implanted entirely within a patient's heart, for example, to provide cardiac therapy. The device 10 is shown implanted in the right atrium (RA) of the patient's heart 8 in a target implant region 4. The device 10 may include one or more fixation members 20 that anchor a distal end of the device against the atrial endocardium in a target implant region 4. The target implant region 4 may lie between the His bundle 5 (or bundle of His) and the coronary sinus 3 and may be adjacent the tricuspid valve 6. The device 10 may be described as a ventricle-from-atrium (VfA) device, which may sense or provide therapy to one or both ventricles (e.g., right ventricle, left ventricle, or both ventricles, depending on the circumstances) while being generally disposed in the right atrium. In particular, the device 10 may include a tissue-piercing electrode that may be implanted in the basal and/or septal region of the left ventricular myocardium of the patient's heart from the triangle of Koch region of the right atrium through the right-atrial endocardium and central fibrous body.

The device 10 may be described as a leadless implantable medical device. As used herein, "leadless" refers to a device being free of a lead extending out of the patient's heart 8. In other words, a leadless device may have a lead that does not extend from outside of the patient's heart to the inside of the patient's heart. Some leadless devices may be introduced through a vein, but once implanted, the device is free of, or may not include, any transvenous lead and may be configured to provide cardiac therapy without using any transvenous lead. Further, a leadless VfA device, in particular, does not use a lead to operably connect to an electrode in the ventricle when a housing of the device is positioned in the atrium. Additionally, a leadless electrode may be coupled to the housing of the medical device without using a lead between the electrode and the housing.

The device 10 may include a dart electrode assembly 12 defining, or having, a straight shaft extending from the distal end region of device 10. The dart electrode assembly 12 may be placed, or at least configured to be placed, through the atrial myocardium and the central fibrous body and into the ventricular myocardium 14, or along the ventricular septum, without perforating entirely through the ventricular endocardial or epicardial surfaces. The dart electrode assembly 12 may carry, or include, an electrode at the distal end region of the shaft such that the electrode may be positioned within the ventricular myocardium for sensing ventricular signals and delivering ventricular pulses (e.g., to depolarize the left ventricle to initiate a contraction of the left ventricle). In some examples, the electrode at the distal end region of the shaft is a cathode electrode provided for use in a bipolar electrode pair for pacing and sensing. While the implant region 4 as illustrated may enable one or more electrodes of the dart electrode assembly 12 to be positioned in the ventricular myocardium, it is recognized that a device having the aspects disclosed herein may be implanted at other locations for multiple chamber pacing (e.g., dual- or triple-chamber pacing), single-chamber pacing with multiple chamber sensing, single-chamber pacing and/or sensing, or other clinical therapy and applications as appropriate.

It is to be understood that although device 10 is described herein as including a single dart electrode assembly, the device 10 may include more than one dart electrode assembly placed, or configured to be placed, through the atrial myocardium and the central fibrous body, and into the ventricular myocardium 14, or along the ventricular septum, without perforating entirely through the ventricular endocardial or epicardial surfaces. Additionally, each dart electrode assembly may carry, or include, more than a single electrode at the distal end region, or along other regions (e.g., proximal or central regions), of the shaft.

The cardiac therapy system 2 may also include a separate medical device 50 (depicted diagrammatically in FIG. 1), which may be positioned outside the patient's heart 8 (e.g., subcutaneously) and may be operably coupled to the patient's heart 8 to deliver cardiac therapy thereto. In one example, separate medical device 50 may be an extravascular ICD. In some embodiments, an extravascular ICD may include a defibrillation lead including, or carrying, a defibrillation electrode. A therapy vector may exist between the defibrillation electrode on the defibrillation lead and a housing electrode of the ICD. Further, one or more electrodes of the ICD may also be used for sensing electrical signals related to the patient's heart 8. The ICD may be configured to deliver shock therapy including one or more defibrillation or cardioversion shocks. For example, if an arrhythmia is sensed, the ICD may send a pulse via the electrical lead wires to shock the heart and restore its normal rhythm. In some examples, the ICD may deliver shock therapy without placing electrical lead wires within the heart or attaching electrical wires directly to the heart (subcutaneous ICDs). Examples of extravascular, subcutaneous ICDs that may be used with the system 2 described herein may be described in U.S. Pat. No. 9,278,229 (Reinke et al.), issued 8 Mar. 2016, which is incorporated herein by reference in its entirety.

In the case of shock therapy (e.g., defibrillation shocks provided by the defibrillation electrode of the defibrillation lead), the separate medical device 50 (e.g., extravascular ICD) may include a control circuit that uses a therapy delivery circuit to generate defibrillation shocks having any of a number of waveform properties, including leading-edge voltage, tilt, delivered energy, pulse phases, and the like. The therapy delivery circuit may, for instance, generate monophasic, biphasic, or multiphasic waveforms. Additionally, the therapy delivery circuit may generate defibrillation waveforms having different amounts of energy. For example, the therapy delivery circuit may generate defibrillation waveforms that deliver a total of between approximately 60-80 Joules (J) of energy for subcutaneous defibrillation.

The separate medical device 50 may further include a sensing circuit. The sensing circuit may be configured to obtain electrical signals sensed via one or more combinations of electrodes and to process the obtained signals. The components of the sensing circuit may include analog components, digital components, or a combination thereof. The sensing circuit may, for example, include one or more sense amplifiers, filters, rectifiers, threshold detectors, analog-to-digital converters (ADCs), or the like. The sensing circuit may convert the sensed signals to digital form and provide the digital signals to the control circuit for processing and/or analysis. For example, the sensing circuit may amplify signals from sensing electrodes and may convert the amplified signals to multi-bit digital signals by an ADC, and then provide the digital signals to the control circuit. In one or more embodiments, the sensing circuit may also compare processed signals to a threshold to detect the existence of atrial or ventricular depolarizations (e.g., P- or R-waves) and indicate the existence of the atrial depolarization (e.g., P-waves) or ventricular depolarizations (e.g., R-waves) to the control circuit.

The device 10 and the separate medical device 50 may cooperate to provide cardiac therapy to the patient's heart 8. For example, the device 10 and the separate medical device 50 may be used to detect tachycardia, monitor tachycardia, and/or provide tachycardia-related therapy. For example, the device 10 may communicate with the separate medical device 50 wirelessly to trigger shock therapy using the separate medical device 50. As used herein, "wirelessly" refers to an operative coupling or connection without using a metal conductor between the device 10 and the separate medical device 50. In one example, wireless communication may use a distinctive, signaling, or triggering electrical-pulse provided by the device 10 that conducts through the patient's tissue and is detectable by the separate medical device 50. In another example, wireless communication may use a communication interface (e.g., an antenna) of the device 10 to provide electromagnetic radiation that propagates through patient's tissue and is detectable, for example, using a communication interface (e.g., an antenna) of the separate medical device 50.

Figure 2:
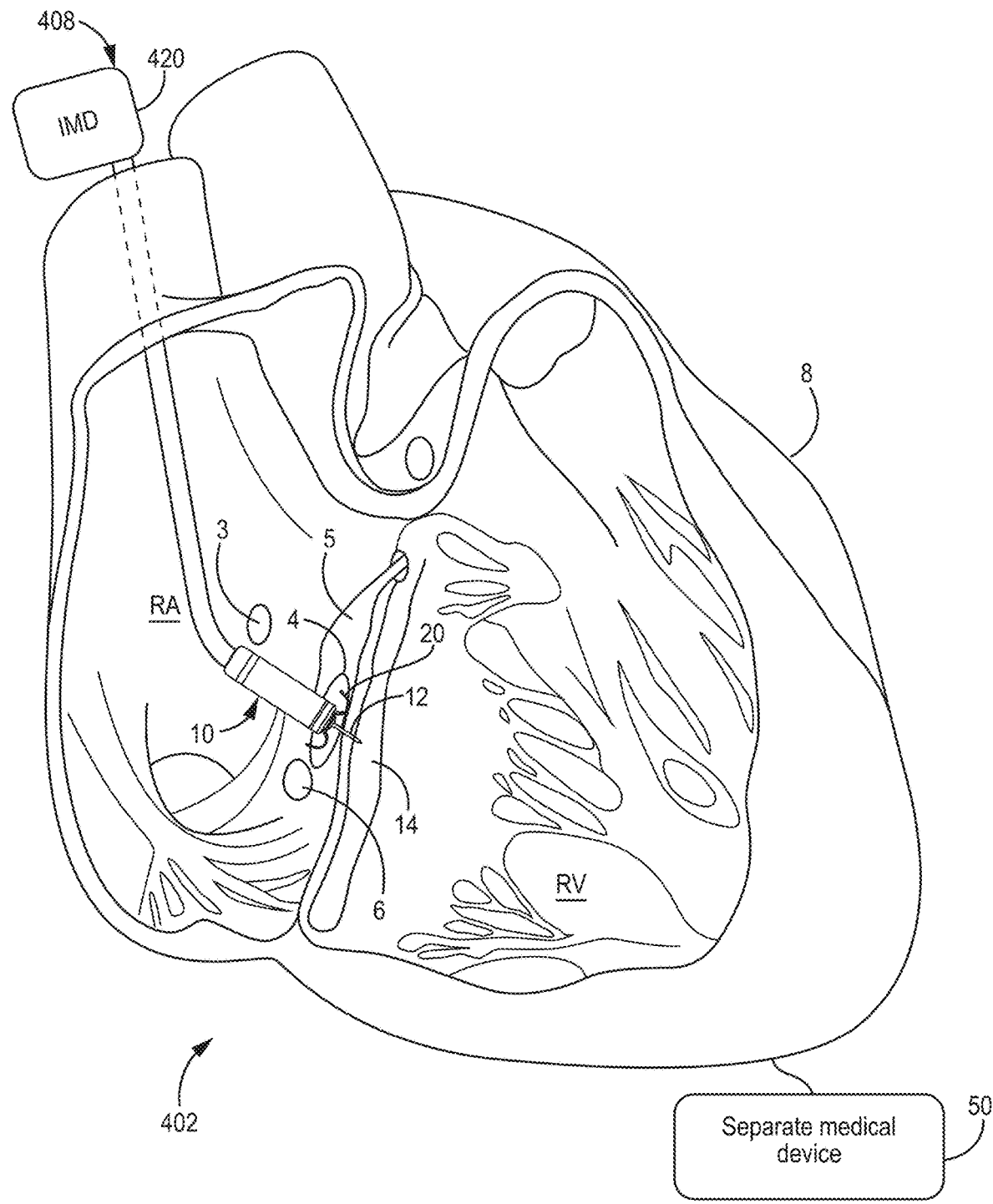
FIGS. 2-4 are conceptual diagrams of illustrative cardiac therapy systems including medical devices including leads with electrodes implanted in a patient's heart for use with, e.g., the illustrative methods of FIGS. 16-20.

With reference to FIG. 2, a leaded medical device 408 includes one, or a single, implantable lead 410 having a tissue-piercing electrode assembly 12 coupled to a distal end region of the lead and implanted inside the patient's heart 8. The housing 420 of the leaded medical device 408 may be implanted and positioned outside of the patient's heart 8 and be configured to calibrate pacing therapy and/or deliver pacing therapy, for example, based on at least a measured heartrate. The lead 410 may include a right-atrial electrode, and the device 408 may operate as a dual-channel capable device (e.g., pacing and/or sensing in both the right atrium and left ventricle). In some embodiments, the lead 410 may not include a right-atrial electrode. In other words, the leaded medical device 408 may be a single channel device, which may be used for asynchronous, triggered, or another type of single-channel pacing. The leaded medical device 408, using the lead 410, may sense activity or deliver pacing to the left ventricle (LV) when the tissue-piercing electrode assembly 12 is implanted, for example, in the same or similar manner as described with respect to FIG. 1.

Figure 3:
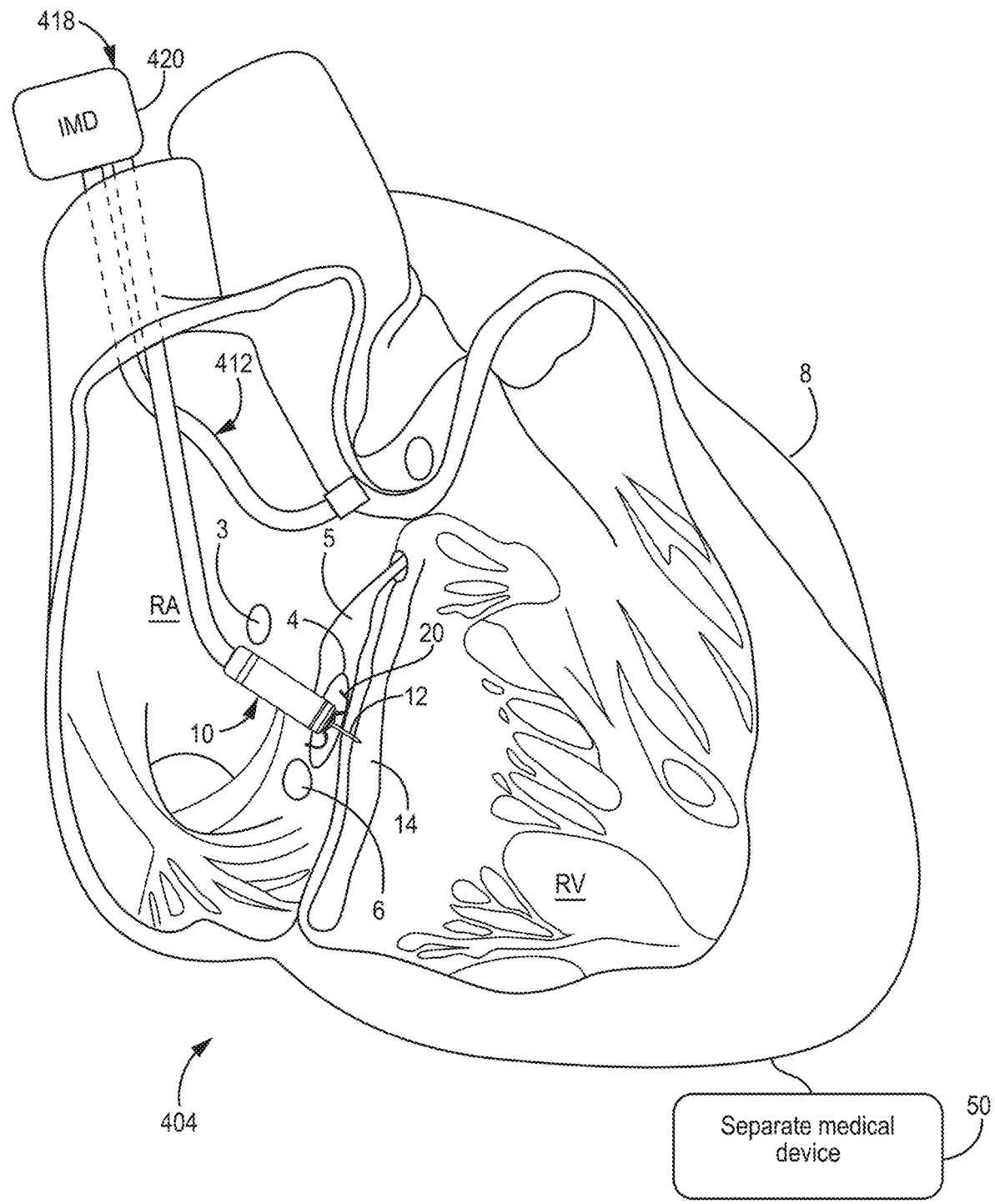

With reference to FIG. 3, leaded medical device 418 is like the leaded medical device 408 of FIG. 2, except that device 418 includes two implantable leads 410, 412. In particular, implantable lead 412 may include an electrode (e.g., a right-atrial electrode) coupled to a distal end region of the lead 412 and may be implanted in a different location than lead 410. In some embodiments, lead 412 is implanted in a different region of the right atrium. In some embodiments, each lead 410, 412 may contribute one channel of a dual-channel device 418. For example, lead 410 may sense activity or deliver pacing to the left ventricle (LV) when the tissue-piercing electrode of the tissue-piercing electrode assembly 12 is implanted, for example, in the same or similar manner as described with respect to FIG. 1, and lead 412 may sense activity or deliver pacing to the right atrium (RA).

Figure 4:
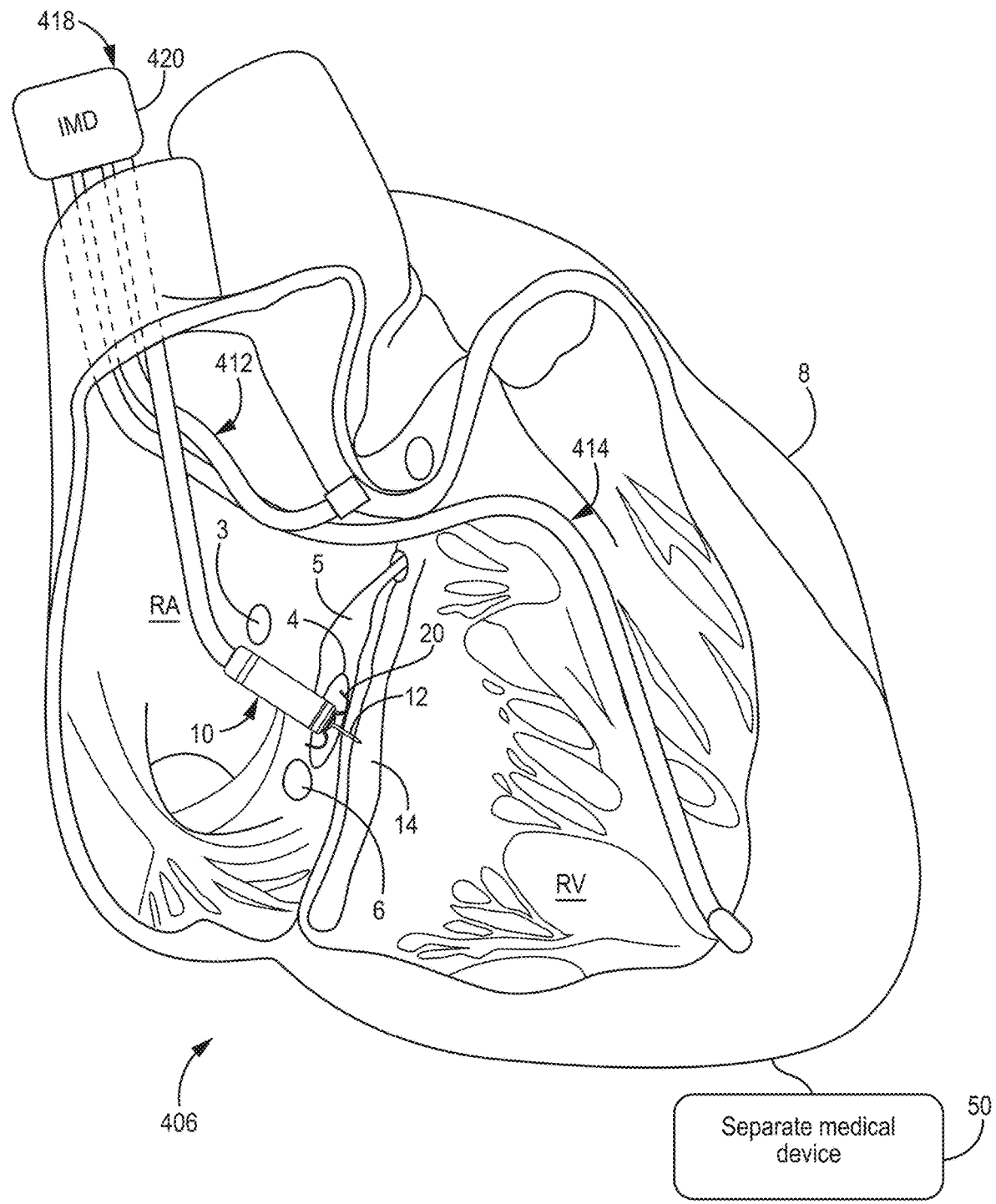

With reference to FIG. 4, leaded medical device 428 is like leaded medical device 418 of FIG. 3 except that device 428 includes three implantable leads 410, 412, 414. In particular, implantable lead 414 may include an electrode (e.g., a right ventricular electrode) coupled to a distal end region of the lead 414 and may be implanted in a different location than leads 410, 412. In some embodiments, lead 414 is implanted in a region of the right ventricle. In some embodiments, each lead 410, 412, 414 may contribute one channel to a multi-channel device 428. For example, lead 410 may sense activity or deliver pacing to the left ventricle (LV) when the tissue-piercing electrode assembly 12 is implanted, for example, in the same or similar manner as described with respect to FIG. 1, lead 412 may sense activity from the delivery of pacing to the right atrium (RA), and lead 414 may sense activity or deliver pacing to the right ventricle (RV).

In some embodiments, a pacing delay between the RV electrode on lead 414 to pace the RV and the LV electrode on lead 410 to pace the LV (e.g., RV-LV pacing delay, or more generally, VV pacing delay) may be calibrated or optimized, for example, using a separate medical device, such as an electrode apparatus (e.g., ECG belt). Various methods may be used to calibrate or optimize the VV delay. In some embodiments, the medical device 428 may be used to test pacing at a plurality of different VV delays. For example, the RV may be paced ahead of the LV by about 80, 60, 40, and 20 milliseconds (ms) and the LV may be paced ahead of the RV by about 80, 60, 40, and 20 ms, as well as simultaneous RV-LV pacing (e.g., about 0 ms VV pacing delay). The medical device 428 may then be configured, for example, automatically, to select a VV pacing delay that, when used for pacing, corresponds to a minimal electrical dyssynchrony measured using the electrode apparatus. The test pacing at different VV pacing delays may be performed using a particular AV delay, such as a nominal AV delay set by the medical device 428 or at a predetermined optimal AV delay based on patient characteristics.

Figure 5:
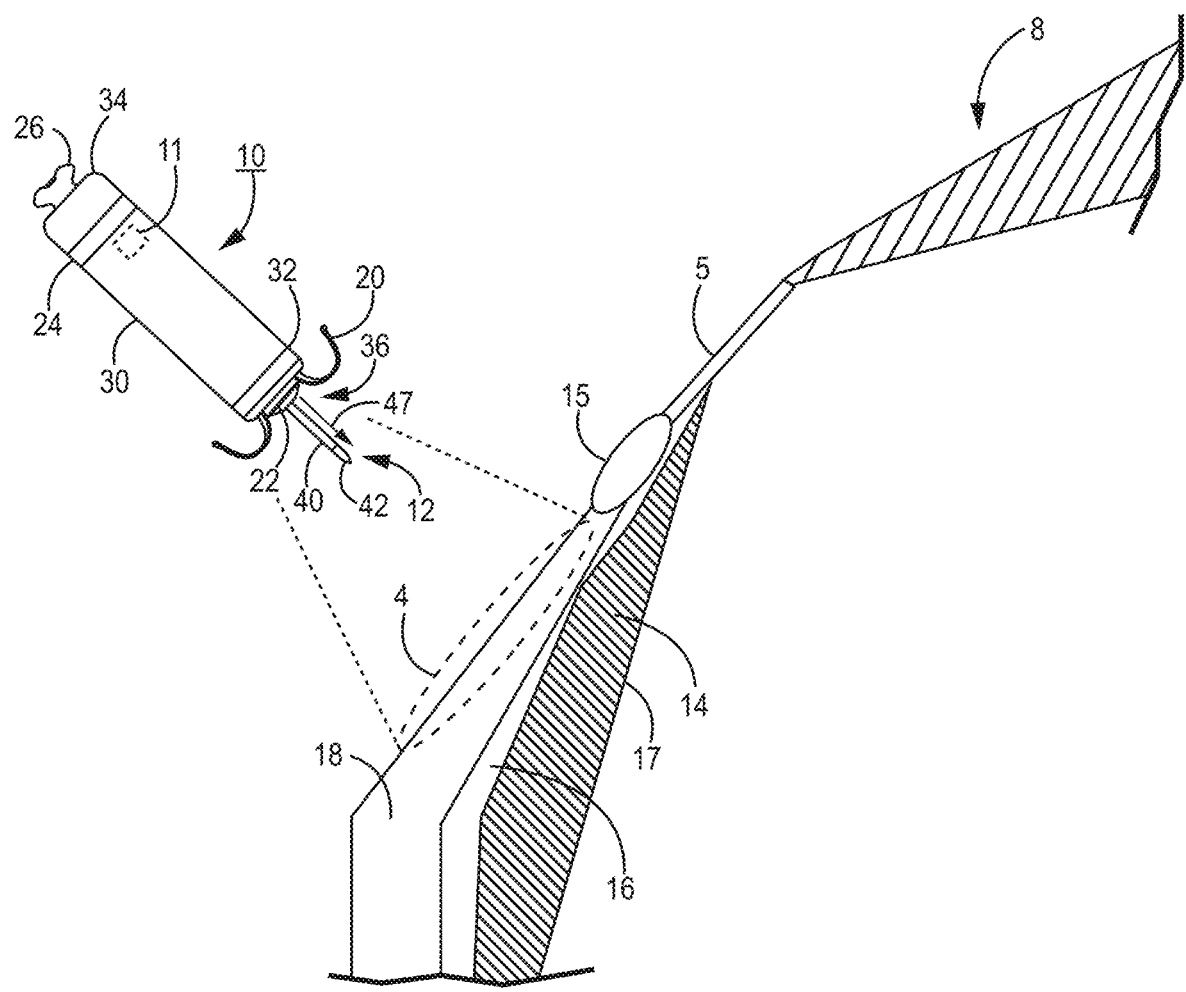
FIG. 5 is an enlarged conceptual diagram of the intracardiac medical device of FIG. 1 and anatomical structures of the patient's heart.

FIG. 5 is an enlarged conceptual diagram of the intracardiac medical device 10 of FIG. 1 and anatomical structures of the patient's heart 8. In particular, the device 10 is configured to pacing therapy and/or deliver pacing therapy, for example, based on at least a measured heartrate. The intracardiac device 10 may include a housing 30. The housing 30 may define a hermetically-sealed internal cavity in which internal components of the device 10 reside, such as a sensing circuit, therapy delivery circuit, control circuit, memory, telemetry circuit, other optional sensors, and a power source as generally described in conjunction with FIG. 8. The housing 30 may be formed from an electrically conductive material including titanium or titanium alloy, stainless steel, MP35N (a non-magnetic nickel-cobalt-chromium-molybdenum alloy), platinum alloy, or other biocompatible metal or metal alloy. In other examples, the housing 30 may be formed from a non-conductive material including ceramic, glass, sapphire, silicone, polyurethane, epoxy, acetyl co-polymer plastics, polyether ether ketone (PEEK), a liquid crystal polymer, or other biocompatible polymer.

In at least one embodiment, the housing 30 may be described as extending between a distal end region 32 and a proximal end region 34 in a generally cylindrical shape to facilitate catheter delivery. In other embodiments, the housing 30 may be prismatic or any other shape to perform the functionality and utility described herein. The housing 30 may include a delivery tool interface member 26, e.g., at the proximal end region 34, for engaging with a delivery tool during implantation of the device 10.

All or a portion of the housing 30 may function as an electrode during cardiac therapy, for example, in sensing and/or pacing. In the example shown, the housing-based electrode 24 is shown to circumscribe a proximal portion (e.g., closer to the proximal end region 34 than the distal end region 32) of the housing 30. When the housing 30 is formed from an electrically conductive material, such as a titanium alloy or other examples listed above, portions of the housing 30 may be electrically insulated by a non-conductive material, such as a coating of parylene, polyurethane, silicone, epoxy, or other biocompatible polymer, leaving one or more discrete areas of conductive material exposed to define the proximal housing-based electrode 24. When the housing 30 is formed from a non-conductive material, such as a ceramic, glass or polymer material, an electrically conductive coating or layer, such as a titanium, platinum, stainless steel, or alloys thereof, may be applied to one or more discrete areas of the housing 30 to form the proximal housing-based electrode 24. In other examples, the proximal housing-based electrode 24 may be a component, such as a ring electrode, that is mounted or assembled onto the housing 30. The proximal housing-based electrode 24 may be electrically coupled to internal circuitry of the device 10, e.g., via the electrically-conductive housing 30 or an electrical conductor when the housing 30 is a non-conductive material.

In the example shown, the proximal housing-based electrode 24 is located nearer to the housing proximal end region 34 than the housing distal end region 32 and is therefore referred to as a "proximal housing-based electrode" 24. In other examples, however, the housing-based electrode 24 may be located at other positions along the housing 30, e.g., more distal relative to the position shown.

At the distal end region 32, the device 10 may include a distal fixation and electrode assembly 36, which may include one or more fixation members 20 and one or more dart electrode assemblies 12 of equal or unequal length. In one example, a single dart electrode assembly 12 includes a shaft 40 extending distally away from the housing distal end region 32 and one or more electrode elements, such as a tip electrode 42 at or near the free, distal end region of the shaft 40. The tip electrode 42 may have a conical or hemispherical distal tip with a relatively narrow tip-diameter (e.g., less than about 1 millimeter (mm)) for penetrating into and through tissue layers without using a sharpened tip or needle-like tip having sharpened or beveled edges.

The shaft 40 of the dart electrode assembly 12 may be a normally straight member and may be rigid. In other embodiments, the shaft 40 may be described as being relatively stiff but still possessing limited flexibility in lateral directions. Further, the shaft 40 may be non-rigid to allow some lateral flexing with heart motion. However, in a relaxed state, when not subjected to any external forces, the shaft 40 may maintain a straight position as shown to hold the tip electrode 42 spaced apart from the housing distal end region 32 at least by the height 47 of the shaft 40. In other words, the dart electrode assembly 12 may be described as resilient.

The dart electrode assembly 12 may be configured to pierce through one or more tissue layers to position the tip electrode 42 within a desired tissue layer, e.g., the ventricular myocardiumn. As such, the height 47, or length, of the shaft 40 may correspond to the expected pacing site depth, and the shaft 40 may have a relatively high compressive strength along its longitudinal axis to resist bending in a lateral or radial direction when pressed against the implant region 4. If a second dart electrode assembly 12 is employed, its length may be unequal to the expected pacing site depth and may be configured to act as an indifferent electrode for delivering of pacing energy to the tissue. A longitudinal axial force may be applied against the tip electrode 42, e.g., by applying a longitudinal pushing force to the proximal end region 34 of the housing 30, to advance the dart electrode assembly 12 into the tissue within the target implant region. The shaft 40 may be described as longitudinally non-compressive and/or elastically deformable in lateral or radial directions when subjected to lateral or radial forces to allow temporary flexing, e.g., with tissue motion, but may return to its normally straight position when lateral forces diminish. When the shaft 40 is not exposed to any external force, or to only a force along its longitudinal central axis, the shaft 40 may retain a straight, linear position as shown.

The one or more fixation members 20 may be described as one or more "tines" having a normally curved position. The tines may be held in a distally extended position within a delivery tool. The distal tips of tines may penetrate the heart tissue to a limited depth before elastically curving back proximally into the normally curved position (shown) upon release from the delivery tool. Further, the fixation members 20 may include one or more aspects described in, for example, U.S. Pat. No. 9,675,579 (Grubac et al.), issued 13 Jun. 2017, and U.S. Pat. No. 9,119,959 (Rys et al.), issued 1 Sep. 2015, each of which is incorporated herein by reference in its entirety.

In some examples, the distal fixation and electrode assembly 36 includes a distal housing-based electrode 22. In the case of using the device 10 as a pacemaker for multiple chamber pacing (e.g., dual- or triple-chamber pacing) and sensing, the tip electrode 42 may be used as a cathode electrode paired with the proximal housing-based electrode 24 serving as a return anode electrode. Alternatively, the distal housing-based electrode 22 may serve as a return anode electrode paired with tip electrode 42 for sensing ventricular signals and delivering ventricular pacing pulses. In other examples, the distal housing-based electrode 22 may be a cathode electrode for sensing atrial signals and delivering pacing pulses to the atrial myocardium in the target implant region 4. When the distal housing-based electrode 22 serves as an atrial cathode electrode, the proximal housing-based electrode 24 may serve as the return anode paired with the tip electrode 42 for ventricular pacing and sensing and as the return anode paired with the distal housing-based electrode 22 for atrial pacing and sensing.

As shown in this illustration, the target implant region 4 in some pacing applications is along the atrial endocardium 18, generally inferior to the AV node 15 and the His bundle 5. The dart electrode assembly 12 may at least partially define the height 47, or length, of the shaft 40 for penetrating through the atrial endocardium 18 in the target implant region 4, through the central fibrous body 16, and into the ventricular myocardium 14 without perforating through the ventricular endocardial surface 17. When the height 47, or length, of the dart electrode assembly 12 is fully advanced into the target implant region 4, the tip electrode 42 may rest within the ventricular myocardium 14, and the distal housing-based electrode 22 may be positioned in intimate contact with or close proximity to the atrial endocardium 18. The dart electrode assembly 12 may have a total combined height 47, or length, of the tip electrode 42 and the shaft 40 from about 3 mm to about 8 mm in various examples. The diameter of the shaft 40 may be less than about 2 mm, and may be about 1 mm or less, or even about 0.6 mm or less.

Figure 8:
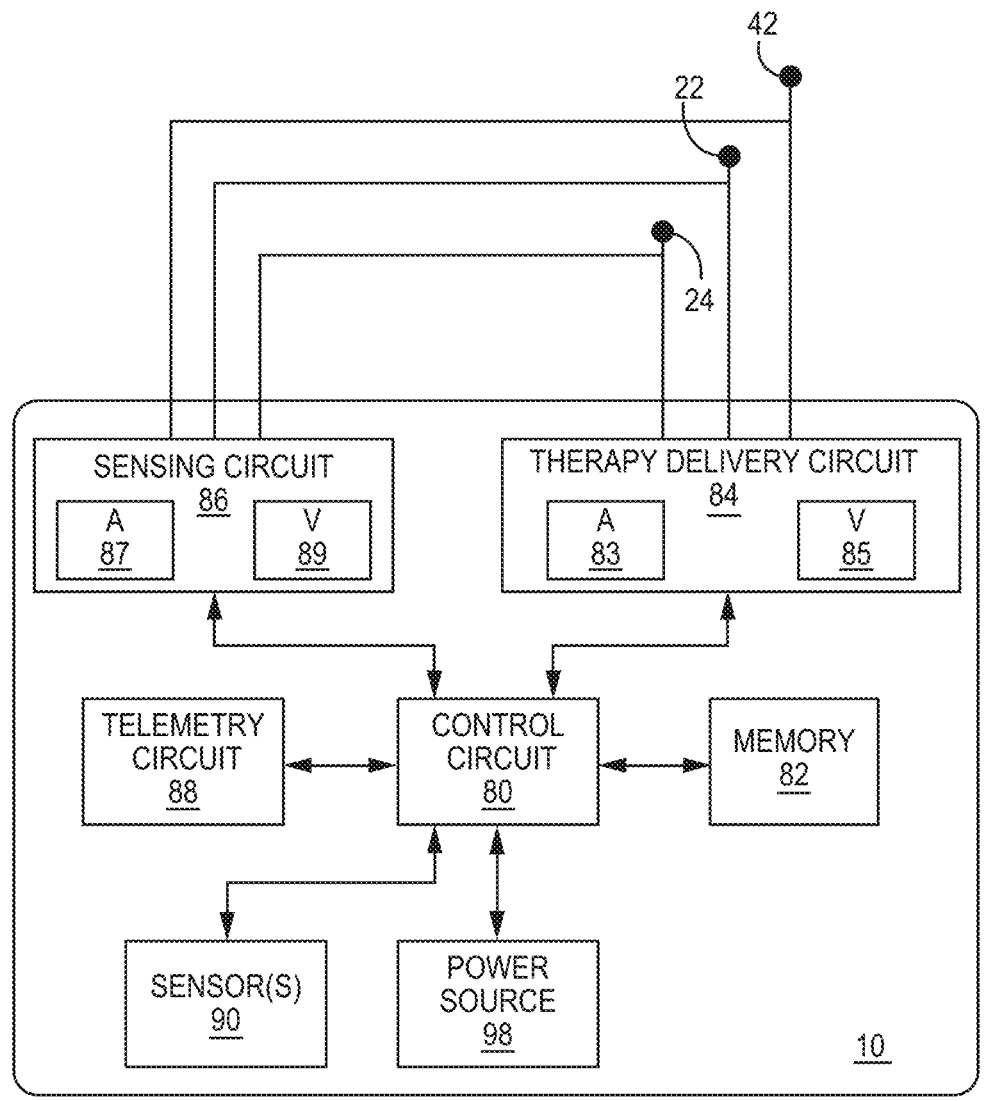
FIG. 8 is a block diagram of illustrative circuitry that may be enclosed within the housing of the medical devices of FIGS. 1-4 and FIG. 22, for example, to provide the functionality and therapy described herein.
Figure 10:
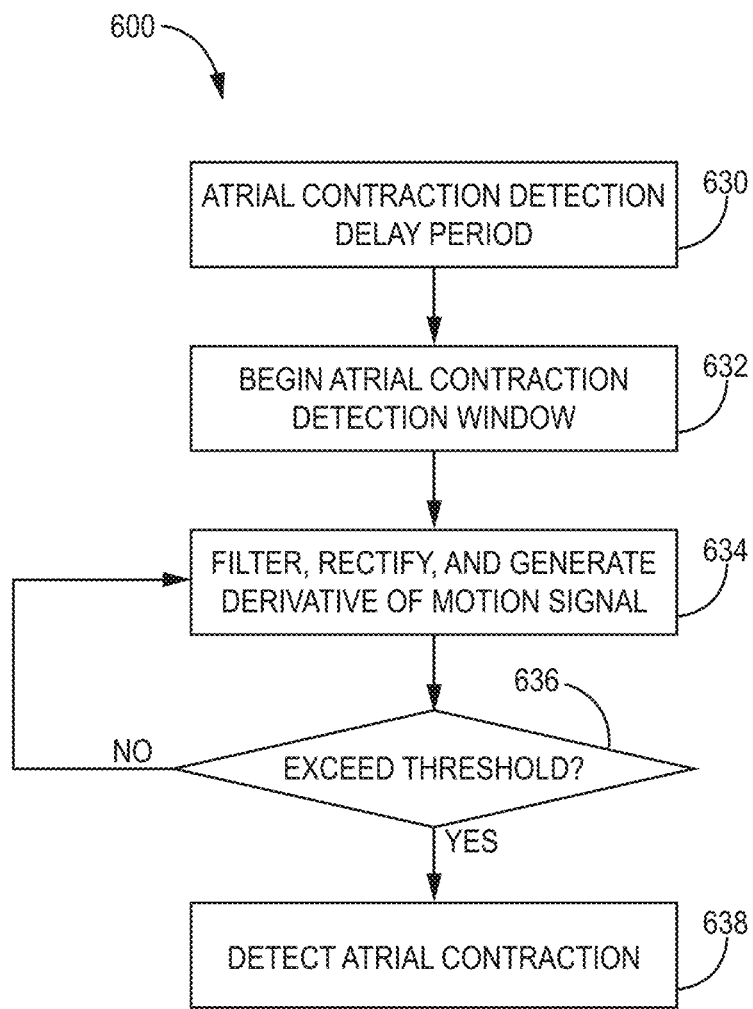
FIG. 10 is a flowchart of an illustrative method of detecting atrial activity using an atrial motion detector for use with, e.g., the illustrative systems and devices of FIGS. 1-4 and FIG. 22.
Figure 11:
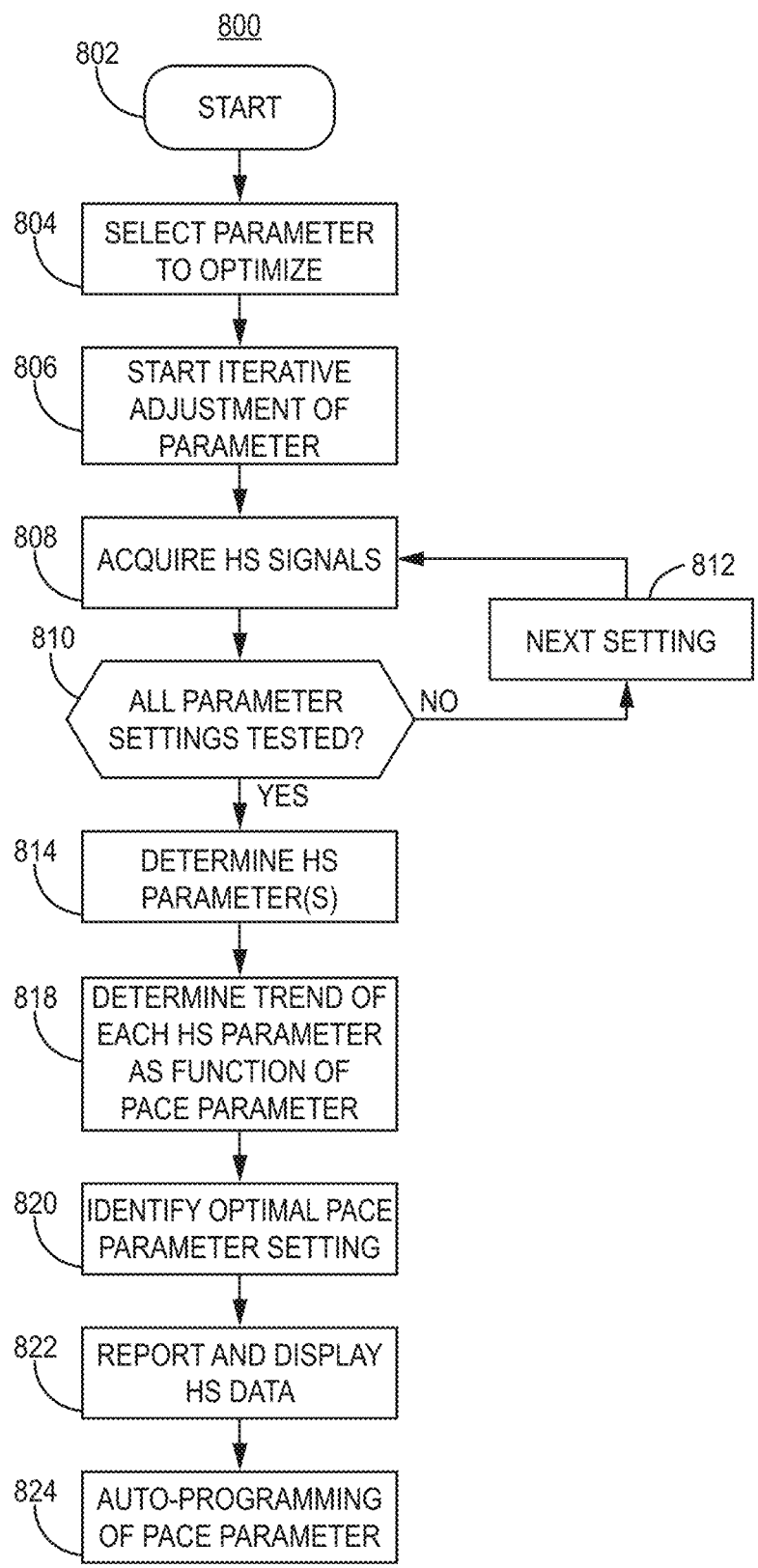
FIG. 11 is a flowchart of an illustrative method of detecting heart sounds to represent physiological response information for use with, e.g., the illustrative systems and devices of FIGS. 1-4 and FIG. 22.
Figure 12:
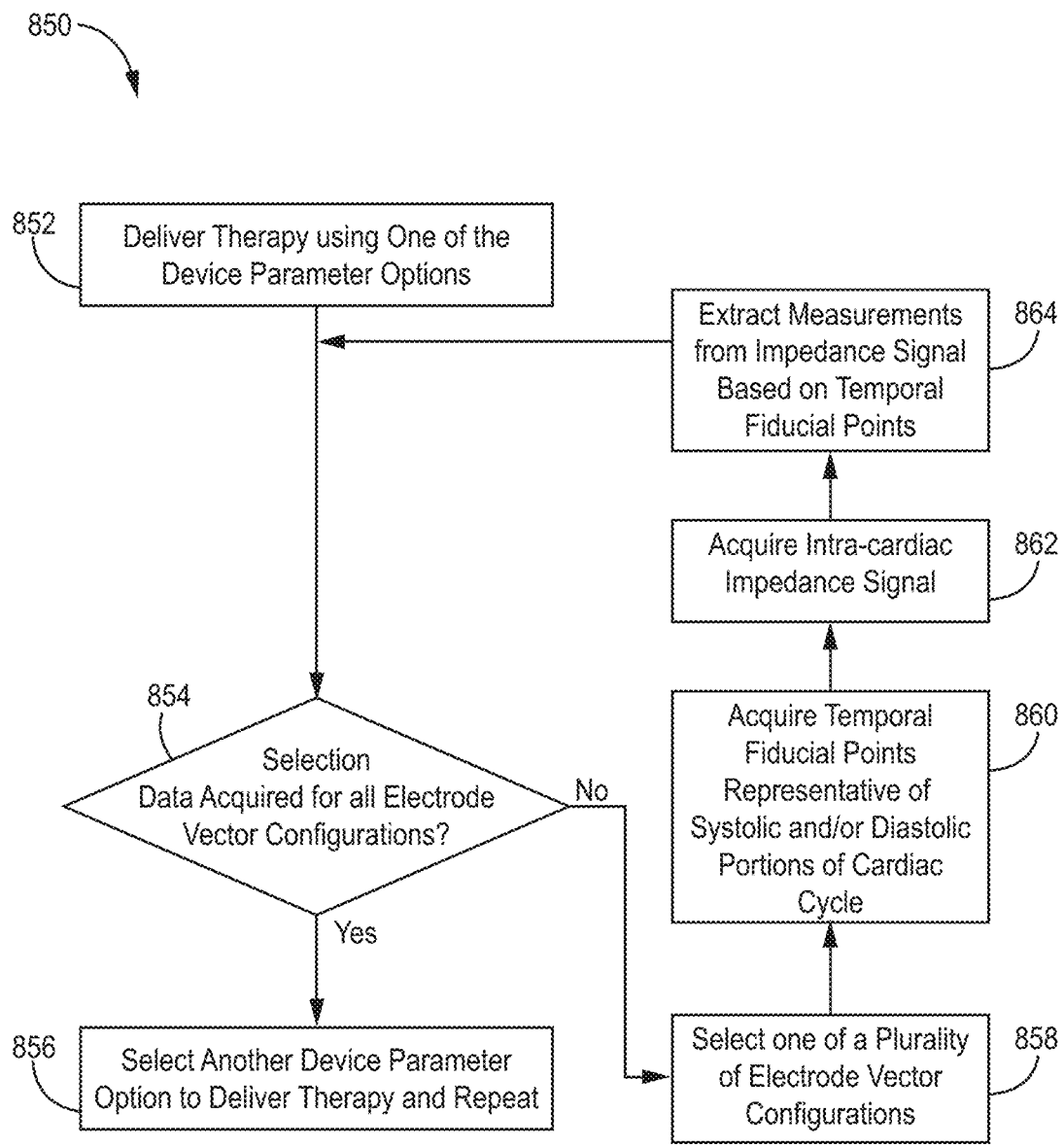
FIG. 12 is a flowchart of an illustrative method of detecting bioimpedance to represent physiological response information for use with, e.g., the illustrative systems and devices of FIGS. 1-4 and FIG. 22.

The device 10 may include an acoustic or motion detector 11 within the housing 30. The acoustic or motion detector 11 may be operably coupled to one or more a control circuit 80 (FIG. 8), a sensing circuit 86 (FIG. 8), or therapy delivery circuit 84 (FIG. 8). In some embodiments, the acoustic or motion detector 11 may be used with methods 600, 650, or 800 as shown in FIGS. 10-12. The acoustic or motion detector 11 may be used to monitor mechanical activity, such as atrial mechanical activity (e.g., an atrial contraction) and/or ventricular mechanical activity (e.g., a ventricular contraction). In some embodiments, the acoustic or motion detector 11 may be used to detect right-atrial mechanical activity. A non-limiting example of an acoustic or motion detector 11 includes an accelerometer or microphone. In some embodiments, the mechanical activity detected by the acoustic or motion detector 11 may be used to supplement or replace electrical activity detected by one or more of the electrodes of the device 10. For example, the acoustic or motion detector 11 may be used in addition to, or as an alternative to, the proximal housing-based electrode 24.

The acoustic or motion detector 11 may also be used for rate response detection or to provide a rate-responsive IMD. Various techniques related to rate response may be described in U.S. Pat. No. 5,154,170 (Bennett et al.), issued Oct. 13, 1992, entitled "Optimization for rate responsive cardiac pacemaker," and U.S. Pat. No. 5,562,711 (Yerich et al.), issued Oct. 8, 1996, entitled "Method and apparatus for rate-responsive cardiac pacing," each of which is incorporated herein by reference in its entirety.

In various embodiments, acoustic or motion detector 11 (or motion sensor) may be used as an HS sensor and may be implemented as a microphone or a 1-, 2- or 3-axis accelerometer. In one embodiment, the acoustical sensor is implemented as a piezoelectric crystal mounted within an implantable medical device housing and responsive to the mechanical motion associated with heart sounds. The piezoelectric crystal may be a dedicated HS sensor or may be used for multiple functions. In the illustrative embodiment shown, the acoustical sensor is embodied as a piezoelectric crystal that is also used to generate a patient alert signal in the form of a perceptible vibration of the IMD housing. Upon detecting an alert condition, control circuit 80 may cause patient alert control circuitry to generate an alert signal by activating the piezoelectric crystal.

The control circuit may be used to control whether the piezoelectric crystal is used in a "listening mode" to sense HS signals by HS sensing circuitry or in an "output mode" to generate a patient alert. During patient alert generation, HS sensing circuitry may be temporarily decoupled from the HS sensor by control circuitry.

Examples of other embodiments of acoustical sensors that may be adapted for implementation with the techniques of the present disclosure may be described generally in U.S. Pat. No. 4,546,777 (Groch, et al.), U.S. Pat. No. 6,869,404 (Schulhauser, et al.), U.S. Pat. No. 5,554,177 (Kieval, et al.), and U.S. Pat. No. 7,035,684 (Lee, et al.), each of which is incorporated herein by reference in its entirety.

Various types of acoustical sensors may be used. The acoustical sensor may be any implantable or external sensor responsive to one or more of the heart sounds generated as described in the foregoing and thereby produces an analog electrical signal correlated in time and amplitude to the heart sounds. The analog signal may be then be processed, which may include digital conversion, by the HS sensing module to obtain HS parameters, such as amplitudes or relative time intervals, as derived by HS sensing module or control circuit 80. The acoustical sensor and HS sensing module may be incorporated in an IMD capable of delivering CRT or another cardiac therapy being optimized or may be implemented in a separate device having wired or wireless communication with IMD or an external programmer or computer used during a pace-parameter optimization procedure as described herein.

Figure 6:
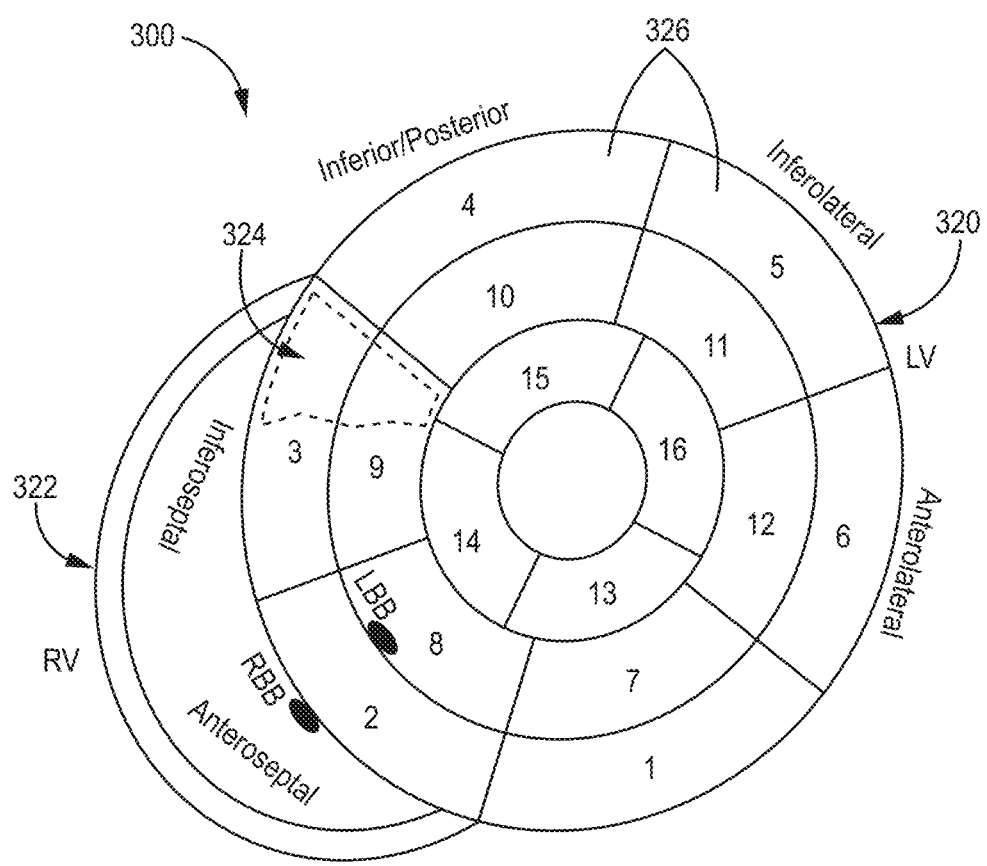
FIG. 6 is a conceptual diagram of a map of a patient's heart in a standard 17 segment view of the left ventricle showing various electrode implantation locations for use with, e.g., the illustrative systems and devices of FIGS. 1-4 and FIG. 22.

FIG. 6 is a two-dimensional (2D) ventricular map 300 of a patient's heart (e.g., a top-down view) showing the left ventricle 320 in a standard 17 segment view and the right ventricle 322. The map 300 includes a plurality of areas 326 corresponding to different regions of a human heart. As illustrated, the areas 326 are numerically labeled 1-17 (which, e.g., correspond to a standard 17 segment model of a human heart, correspond to 17 segments of the left ventricle of a human heart, etc.). Areas 326 of the map 300 may include basal anterior area 1, basal anteroseptal area 2, basal inferoseptal area 3, basal inferior area 4, basal inferolateral area 5, basal anterolateral area 6, mid-anterior area 7, mid-anteroseptal area 8, mid-inferoseptal area 9, mid-inferior area 10, mid-inferolateral area 11, mid-anterolateral area 12, apical anterior area 13, apical septal area 14, apical inferior area 15, apical lateral area 16, and apex area 17. The inferoseptal and anteroseptal areas of the right ventricle 322 are also illustrated, as well as the right bunch branch (RBB) and left bundle branch (LBB).

In some embodiments, any of the tissue-piercing electrodes of the present disclosure may be implanted in the basal and/or septal region of the left ventricular myocardium of the patient's heart. In particular, the tissue-piercing electrode may be implanted from the triangle of Koch region of the right atrium through the right-atrial endocardium and central fibrous body.

Once implanted, the tissue-piercing electrode may be positioned in the target implant region 4 (FIGS. 1-5), such as the basal and/or septal region of the left ventricular myocardium. With reference to map 300, the basal region includes one or more of the basal anterior area 1, basal anteroseptal area 2, basal inferoseptal area 3, basal inferior area 4, mid-anterior area 7, mid-anteroseptal area 8, mid-inferoseptal area 9, and mid-inferior area 10. With reference to map 300, the septal region includes one or more of the basal anteroseptal area 2, basal anteroseptal area 3, mid-anteroseptal area 8, mid-inferoseptal area 9, and apical septal area 14.

In some embodiments, the tissue-piercing electrode may be positioned in the basal septal region of the left ventricular myocardium when implanted. The basal septal region may include one or more of the basal anteroseptal area 2, basal inferoseptal area 3, mid-anteroseptal area 8, and mid-inferoseptal area 9.

In some embodiments, the tissue-piercing electrode may be positioned in the high inferior/posterior basal septal region of the left ventricular myocardium when implanted. The high inferior/posterior basal septal region of the left ventricular myocardium may include a portion of one or more of the basal inferoseptal area 3 and mid-inferoseptal area 9 (e.g., the basal inferoseptal area only, the mid-inferoseptal area only, or both the basal inferoseptal area and the mid-inferoseptal area). For example, the high inferior/posterior basal septal region may include region 324 illustrated generally as a dashed-line boundary. As shown, the dashed line boundary represents an approximation of where the high inferior/posterior basal septal region is located, which may take a somewhat different shape or size depending on the particular application.

Figure 7:
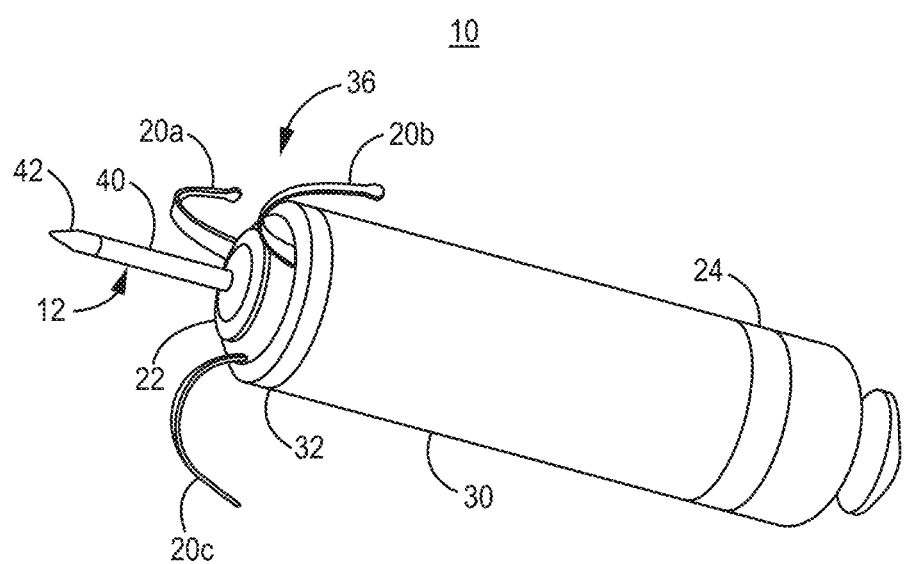
FIG. 7 is a perspective view of an intracardiac medical device having a distal fixation and electrode assembly that includes a distal housing-based electrode implemented as a ring electrode for use with, e.g., the illustrative systems and devices of FIGS. 1-4 and FIG. 22.

FIG. 7 is a three-dimensional perspective view of the device 10 capable of calibrating pacing therapy and/or delivering pacing therapy, for example, based on at least a measured heartrate. As shown, the distal fixation and electrode assembly 36 includes the distal housing-based electrode 22 implemented as a ring electrode. The distal housing-based electrode 22 may be positioned in intimate contact with or operative proximity to atrial tissue when fixation member tines 20a, 20b, and 20c of the fixation members 20, engage with the atrial tissue. The tines 20a, 20b, and 20c, which may be elastically deformable, may be extended distally during delivery of device 10 to the implant site. For example, the tines 20a, 20b, and 20c may pierce the atrial endocardial surface as the device 10 is advanced out of the delivery tool and flex back into their normally curved position (as shown) when no longer constrained within the delivery tool. As the tines 20a, 20b, and 20c curve back into their normal position, the fixation member 20 may pull the distal fixation member and electrode assembly 36 toward the atrial endocardial surface. As the distal fixation member and electrode assembly 36 is pulled toward the atrial endocardium, the tip electrode 42 may be advanced through the atrial myocardium and the central fibrous body and into the ventricular myocardium. The distal housing-based electrode 22 may then be positioned against the atrial endocardial surface.

The distal housing-based electrode 22 may include a ring formed of an electrically conductive material, such as titanium, platinum, iridium, or alloys thereof. The distal housing-based electrode 22 may be a single, continuous ring electrode. In other examples, portions of the ring may be coated with an electrically insulating coating, e.g., parylene, polyurethane, silicone, epoxy, or another insulating coating, to reduce the electrically conductive surface area of the ring electrode. For instance, one or more sectors of the ring may be coated to separate two or more electrically conductive exposed surface areas of the distal housing-based electrode 22. Reducing the electrically conductive surface area of the distal housing-based electrode 22, e.g., by covering portions of the electrically conductive ring with an insulating coating, may increase the electrical impedance of the distal housing-based electrode 22, and thereby, reduce the current delivered during a pacing pulse that captures the myocardium, e.g., the atrial myocardial tissue. A lower current drain may conserve the power source, e.g., one or more rechargeable or non-rechargeable batteries, of the device 10.

As described above, the distal housing-based electrode 22 may be configured as an atrial cathode electrode for delivering pacing pulses to the atrial tissue at the implant site in combination with the proximal housing-based electrode 24 as the return anode. The electrodes 22 and 24 may be used to sense atrial P-waves for use in controlling atrial pacing pulses (delivered in the absence of a sensed P-wave) and for controlling atrial-synchronized ventricular pacing pulses delivered using the tip electrode 42 as a cathode and the proximal housing-based electrode 24 as the return anode. In other examples, the distal housing-based electrode 22 may be used as a return anode in conjunction with the cathode tip electrode 42 for ventricular pacing and sensing.

Figure 9:
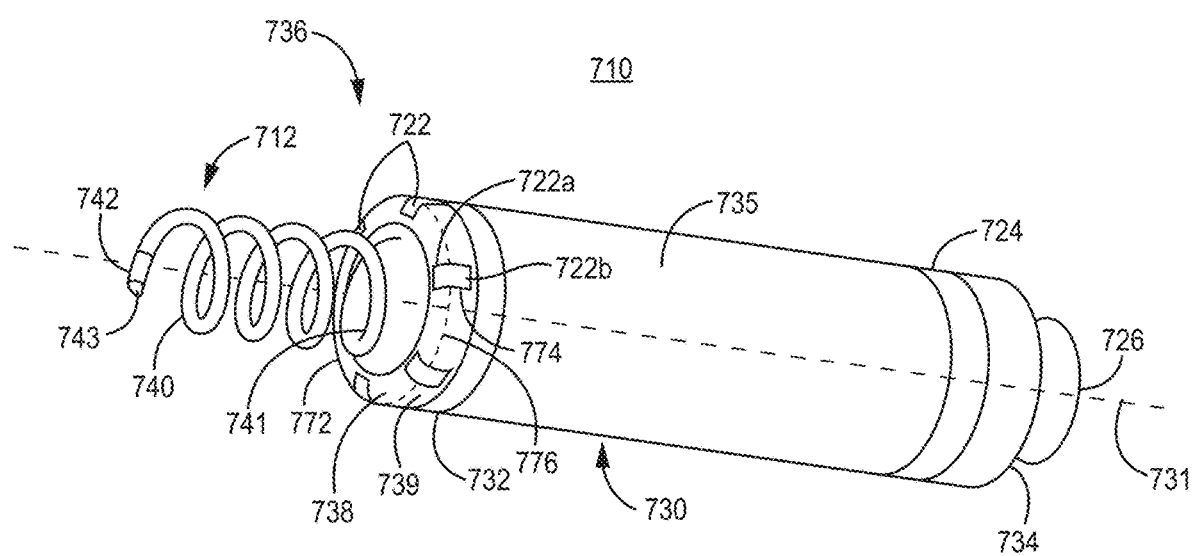
FIG. 9 is a perspective view of another illustrative intracardiac medical device for use with, e.g., the illustrative systems and devices of FIGS. 1-4 and FIG. 22.

FIG. 8 is a block diagram of circuitry that may be enclosed within the housing 30 (FIG. 7) to provide the functions of calibrating pacing therapy and/or delivering pacing therapy, for example, based on at least a measured heartrate, using the device 10 according to one example or within the housings of any other medical devices described herein (e.g., device 408 of FIG. 2, device 418 of FIG. 3, device 428 of FIG. 4, or device 710 of FIG. 9). The separate medical device 50 (FIGS. 1-4) may include some or all the same components, which may be configured in a similar manner. The electronic circuitry enclosed within housing 30 may include software, firmware, and hardware that cooperatively monitor atrial and ventricular electrical cardiac signals, determine when a cardiac therapy is necessary, and/or deliver electrical pulses to the patient's heart according to programmed therapy mode and pulse control parameters. The electronic circuitry may include a control circuit 80 (e.g., including processing circuitry), a memory 82, a therapy delivery circuit 84, a sensing circuit 86, and/or a telemetry circuit 88. In some examples, the device 10 includes one or more sensors 90 for producing a signal that is correlated to a physiological function, state, or condition of the patient, such as a patient activity sensor, for use in determining a need for pacing therapy and/or controlling a pacing rate. For example, one sensor 90 may include an inertial measurement unit (e.g., accelerometer) to measure motion.

The power source 98 may provide power to the circuitry of the device 10 including each of the components 80, 82, 84, 86, 88, 90 as needed. The power source 98 may include one or more energy storage devices, such as one or more rechargeable or non-rechargeable batteries. The connections (not shown) between the power source 98 and each of the components 80, 82, 84, 86, 88, 90 may be understood from the general block diagram illustrated to one of ordinary skill in the art. For example, the power source 98 may be coupled to one or more charging circuits included in the therapy delivery circuit 84 for providing the power used to charge holding capacitors included in the therapy delivery circuit 84 that are discharged at appropriate times under the control of the control circuit 80 for delivering pacing pulses, e.g., according to a dual chamber pacing mode such as DDI(R). The power source 98 may also be coupled to components of the sensing circuit 86, such as sense amplifiers, analog-to-digital converters, switching circuitry, etc., sensors 90, the telemetry circuit 88, and the memory 82 to provide power to the various circuits.

The functional blocks shown represent functionality included in the device 10 and may include any discrete and/or integrated electronic circuit components that implement analog, and/or digital circuits capable of producing the functions attributed to the medical device 10 herein. The various components may include processing circuitry, such as an application specific integrated circuit (ASIC), an electronic circuit, a processor (shared, dedicated, or group), and memory that execute one or more software or firmware programs, a combinational logic circuit, state machine, or other suitable components or combinations of components that provide the described functionality. The particular form of software, hardware, and/or firmware employed to implement the functionality disclosed herein will be determined primarily by the particular system architecture employed in the medical device and by the particular detection and therapy delivery methodologies employed by the medical device.

The memory 82 may include any volatile, non-volatile, magnetic, or electrical non-transitory computer-readable storage media, such as random-access memory (RAM), read-only memory (ROM), non-volatile RAM (NVRAM), electrically-erasable programmable ROM (EEPROM), flash memory, or any other memory device. Furthermore, the memory 82 may include a non-transitory computer-readable media storing instructions that, when executed by one or more processing circuits, cause the control circuit 80 and/or other processing circuitry to calibrate pacing therapy and/or perform a single, dual, or triple-chamber calibrated pacing therapy (e.g., single or multiple chamber pacing), or other cardiac therapy functions (e.g., sensing or delivering therapy), attributed to the device 10. The non-transitory computer-readable media storing the instructions may include any of the media listed above.

The control circuit 80 may communicate, e.g., via a data bus, with the therapy delivery circuit 84 and the sensing circuit 86 for sensing cardiac electrical signals and controlling delivery of cardiac electrical stimulation therapies in response to sensed cardiac events, e.g., P-waves and R-waves, or the absence thereof. The tip electrode 42, the distal housing-based electrode 22, and the proximal housing-based electrode 24 may be electrically coupled to the therapy delivery circuit 84 for delivering electrical stimulation pulses to the patient's heart and to the sensing circuit 86 and for sensing cardiac electrical signals.

The sensing circuit 86 may include an atrial (A) sensing channel 87 and a ventricular (V) sensing channel 89. The distal housing-based electrode 22 and the proximal housing-based electrode 24 may be coupled to the atrial sensing channel 87 for sensing atrial signals, e.g., P-waves attendant to the depolarization of the atrial myocardium. In examples that include two or more selectable distal housing-based electrodes, the sensing circuit 86 may include switching circuitry for selectively coupling one or more of the available distal housing-based electrodes to cardiac event detection circuitry included in the atrial sensing channel 87. Switching circuitry may include a switch array, switch matrix, multiplexer, or any other type of switching device suitable to selectively couple components of the sensing circuit 86 to selected electrodes. The tip electrode 42 and the proximal housing-based electrode 24 may be coupled to the ventricular sensing channel 89 for sensing ventricular signals, e.g., R-waves attendant to the depolarization of the ventricular myocardium.

Each of the atrial sensing channel 87 and the ventricular sensing channel 89 may include cardiac event detection circuitry for detecting P-waves and R-waves, respectively, from the cardiac electrical signals received by the respective sensing channels. The cardiac event detection circuitry included in each of the channels 87 and 89 may be configured to amplify, filter, digitize, and rectify the cardiac electrical signal received from the selected electrodes to improve the signal quality for detecting cardiac electrical events. The cardiac event detection circuitry within each channel 87 and 89 may include one or more sense amplifiers, filters, rectifiers, threshold detectors, comparators, analog-to-digital converters (ADCs), timers, or other analog or digital components. A cardiac event sensing threshold, e.g., a P-wave sensing threshold and an R-wave sensing threshold, may be automatically adjusted by each respective sensing channel 87 and 89 under the control of the control circuit 80, e.g., based on timing intervals and sensing threshold values determined by the control circuit 80, stored in the memory 82, and/or controlled by hardware, firmware, and/or software of the control circuit 80 and/or the sensing circuit 86.

Upon detecting a cardiac electrical event based on a sensing threshold crossing, the sensing circuit 86 may produce a sensed event signal that is passed to the control circuit 80. For example, the atrial sensing channel 87 may produce a P-wave sensed event signal in response to a P-wave sensing threshold crossing. The ventricular sensing channel 89 may produce an R-wave sensed event signal in response to an R-wave sensing threshold crossing. The sensed event signals may be used by the control circuit 80 for setting pacing escape interval timers that control the basic time intervals used for scheduling cardiac pacing pulses. A sensed event signal may trigger or inhibit a pacing pulse depending on the particular programmed pacing mode. For example, a P-wave sensed event signal received from the atrial sensing channel 87 may cause the control circuit 80 to inhibit a scheduled atrial pacing pulse and schedule a ventricular pacing pulse at a programmed atrioventricular (AV) pacing interval. If an R-wave is sensed before the AV pacing interval expires, the ventricular pacing pulse may be inhibited. If the AV pacing interval expires before the control circuit 80 receives an R-wave sensed event signal from the ventricular sensing channel 89, the control circuit 80 may use the therapy delivery circuit 84 to deliver the scheduled ventricular pacing pulse synchronized to the sensed P-wave.

In some examples, the device 10 may be configured to deliver a variety of pacing therapies including bradycardia pacing, cardiac resynchronization therapy, post-shock pacing, and/or tachycardia-related therapy, such as ATP, among others. For example, the device 10 may be configured to detect non-sinus tachycardia and deliver ATP. The control circuit 80 may determine cardiac event time intervals, e.g., P-P intervals between consecutive P-wave sensed event signals received from the atrial sensing channel 87, R-R intervals between consecutive R-wave sensed event signals received from the ventricular sensing channel 89, and P-R and/or R-P intervals received between P-wave sensed event signals and R-wave sensed event signals. These intervals may be compared to tachycardia detection intervals for detecting non-sinus tachycardia. Tachycardia may be detected in a given heart chamber based on a threshold number of tachycardia detection intervals being detected.

The therapy delivery circuit 84 may include atrial pacing circuit 83 and ventricular pacing circuit 85. Each pacing circuit 83, 85 may include charging circuitry, one or more charge storage devices such as one or more low voltage holding capacitors, an output capacitor, and/or switching circuitry that controls when the holding capacitor(s) are charged and discharged across the output capacitor to deliver a pacing pulse to the pacing electrode vector coupled to respective pacing circuits 83, 85. The tip electrode 42 and the proximal housing-based electrode 24 may be coupled to the ventricular pacing circuit 85 as a bipolar cathode and anode pair for delivering ventricular pacing pulses, e.g., upon expiration of an AV or VV pacing interval set by the control circuit 80 for providing atrial-synchronized ventricular pacing and a basic lower ventricular pacing rate.

The atrial pacing circuit 83 may be coupled to the distal housing-based electrode 22 and the proximal housing-based electrode 24 to deliver atrial pacing pulses. The control circuit 80 may set one or more atrial pacing intervals according to a programmed lower pacing rate or a temporary lower rate set according to a rate-responsive sensor-indicated pacing rate. Atrial pacing circuit may be controlled to deliver an atrial pacing pulse if the atrial pacing interval expires before a P-wave sensed event signal is received from the atrial sensing channel 87. The control circuit 80 starts an AV pacing interval in response to a delivered atrial pacing pulse to provide synchronized multiple chamber pacing (e.g., dual- or triple-chamber pacing).

Charging of a holding capacitor of the atrial or ventricular pacing circuit 83, 85 to a programmed pacing voltage amplitude and discharging of the capacitor for a programmed pacing pulse width may be performed by the therapy delivery circuit 84 according to control signals received from the control circuit 80. For example, a pace timing circuit included in the control circuit 80 may include programmable digital counters set by a microprocessor of the control circuit 80 for controlling the basic pacing time intervals associated with various single-chamber or multiple-chamber pacing (e.g., dual- or triple-chamber pacing) modes or anti-tachycardia pacing sequences. The microprocessor of the control circuit 80 may also set the amplitude, pulse width, polarity, or other characteristics of the cardiac pacing pulses, which may be based on programmed values stored in the memory 82.

The device 10 may include other sensors 90 for sensing signals from the patient for use in determining a need for and/or controlling electrical stimulation therapies delivered by the therapy delivery circuit 84. In some examples, a sensor indicative of a need for increased cardiac output may include a patient activity sensor, such as an accelerometer. An increase in the metabolic demand of the patient due to increased activity as indicated by the patient activity sensor may be determined by the control circuit 80 for use in determining a sensor-indicated pacing rate. The control circuit 80 may be used to calibrate and/or deliver pacing therapy based on the patient activity sensor (e.g., a measured heartrate).

Control parameters utilized by the control circuit 80 for sensing cardiac events and controlling pacing therapy delivery may be programmed into the memory 82 via the telemetry circuit 88, which may also be described as a communication interface. The telemetry circuit 88 includes a transceiver and antenna for communicating with an external device, such as a programmer or home monitor, using radio frequency communication or other communication protocols. The control circuit 80 may use the telemetry circuit 88 to receive downlink telemetry from and send uplink telemetry to the external device. In some cases, the telemetry circuit 88 may be used to transmit and receive communication signals to/from another medical device implanted in the patient.

FIG. 9 is a three-dimensional perspective view of another leadless intracardiac medical device 710 that may be configured for calibrating pacing therapy and/or delivering pacing therapy, for example, based on at least a measured heartrate, for single or multiple chamber cardiac therapy (e.g., dual- or triple-chamber cardiac therapy) according to another example. The device 710 may include a housing 730 having an outer sidewall 735, shown as a cylindrical outer sidewall, extending from a housing distal end region 732 to a housing proximal end region 734. The housing 730 may enclose electronic circuitry configured to perform single- or multiple-chamber cardiac therapy, including atrial and ventricular cardiac electrical signal sensing and pacing the atrial and ventricular chambers. The delivery tool interface member 726 is shown on the housing proximal end region 734.

A distal fixation and electrode assembly 736 may be coupled to the housing distal end region 732. The distal fixation and electrode assembly 736 may include an electrically insulative distal member 772 coupled to the housing distal end region 732. The tissue-piercing electrode assembly 712 extends away from the housing distal end region 732, and multiple non-tissue piercing electrodes 722 may be coupled directly to the insulative distal member 772. The tissue-piercing electrode assembly 712 extends in a longitudinal direction away from the housing distal end region 732 and may be coaxial with the longitudinal center axis 731 of the housing 730.

The distal tissue-piercing electrode assembly 712 may include an electrically insulated shaft 740 and a tip electrode 742 (e.g., tissue-piercing electrode). In some examples, the tissue-piercing electrode assembly 712 is an active fixation member including a helical shaft 740 and a distal cathode tip electrode 742. The helical shaft 740 may extend from a shaft distal end region 743 to a shaft proximal end region 741, which may be directly coupled to the insulative distal member 772. The helical shaft 740 may be coated with an electrically insulating material, e.g., parylene or other examples listed herein, to avoid sensing or stimulation of cardiac tissue along the shaft length. The tip electrode 742 is at the shaft distal end region 743 and may serve as a cathode electrode for delivering ventricular pacing pulses and sensing ventricular electrical signals using the proximal housing-based electrode 724 as a return anode when the tip electrode 742 is advanced into ventricular tissue. The proximal housing-based electrode 724 may be a ring electrode circumscribing the housing 730 and may be defined by an uninsulated portion of the longitudinal sidewall 735. Other portions of the housing 730 not serving as an electrode may be coated with an electrically insulating material as described above in conjunction with FIG. 7.

Using two or more tissue-piercing electrodes (e.g., of any type) penetrating into the LV myocardium may be used for more localized pacing capture and may mitigate ventricular pacing spikes affecting capturing atrial tissue. In some embodiments, multiple tissue-piercing electrodes may include two or more dart-type electrode assemblies (e.g., electrode assembly 12 of FIG. 7), a helical-type electrode (e.g., electrode assembly 712) Non-limiting examples of multiple tissue-piercing electrodes include two dart electrode assemblies, a helix electrode with a dart electrode assembly extending therethrough (e.g., through the center), or dual intertwined helixes. Multiple tissue-piercing electrodes may also be used for bipolar or multi-polar pacing.

In some embodiments, one or more tissue-piercing electrodes (e.g., of any type) that penetrate into the LV myocardium may be a multi-polar tissue-piercing electrode. A multi-polar tissue-piercing electrode may include one or more electrically active and electrically separate elements, which may enable bipolar or multi-polar pacing from one or more tissue-piercing electrodes.

Multiple non-tissue piercing electrodes 722 may be provided along a periphery of the insulative distal member 772, peripheral to the tissue-piercing electrode assembly 712. The insulative distal member 772 may define a distal-facing surface 738 of the device 710 and a circumferential surface 739 that circumscribes the device 710 adjacent to the housing longitudinal sidewall 735. Non-tissue piercing electrodes 722 may be formed of an electrically conductive material, such as titanium, platinum, iridium, or alloys thereof. In the illustrated embodiment, six non-tissue piercing electrodes 722 are spaced apart radially at equal distances along the outer periphery of insulative distal member 772. However, two or more non-tissue piercing electrodes 722 may be provided.

Non-tissue piercing electrodes 722 may be discrete components each retained within a respective recess 774 in the insulative member 772 sized and shaped to mate with the non-tissue piercing electrode 722. In other examples, the non-tissue piercing electrodes 722 may each be an uninsulated, exposed portion of a unitary member mounted within or on the insulative distal member 772. Intervening portions of the unitary member not functioning as an electrode may be insulated by the insulative distal member 772 or, if exposed to the surrounding environment, may be coated with an electrically insulating coating, e.g., parylene, polyurethane, silicone, epoxy, or another insulating coating.

When the tissue-piercing electrode assembly 712 is advanced into cardiac tissue, at least one non-tissue piercing electrode 722 may be positioned against, in intimate contact with, or in operative proximity to, a cardiac tissue surface for delivering pulses and/or sensing cardiac electrical signals produced by the patient's heart. For example, non-tissue piercing electrodes 722 may be positioned in contact with right-atrial endocardial tissue for pacing and sensing in the atrium when the tissue-piercing electrode assembly 712 is advanced into the atrial tissue and through the central fibrous body until the distal tip electrode 742 is positioned in direct contact with ventricular tissue, e.g., ventricular myocardium and/or a portion of the ventricular conduction system.

Non-tissue piercing electrodes 722 may be coupled to the therapy delivery circuit 84 and the sensing circuit 86 (see FIG. 8) enclosed by the housing 730 to function collectively as a cathode electrode for delivering atrial pacing pulses and for sensing atrial electrical signals, e.g., P-waves, in combination with the proximal housing-based electrode 724 as a return anode. Switching circuitry included in the sensing circuit 86 may be activated under the control of the control circuit 80 to couple one or more of the non-tissue piercing electrodes to the atrial sensing channel 87. Distal, non-tissue piercing electrodes 722 may be electrically isolated from each other so that each individual one of the electrodes 722 may be individually selected by switching circuitry included in the therapy delivery circuit 84 to serve alone or in a combination of two or more of the electrodes 722 as an atrial cathode electrode. Switching circuitry included in the therapy delivery circuit 84 may be activated under the control of the control circuit 80 to couple one or more of the non-tissue piercing electrodes 722 to the atrial pacing circuit 83. Two or more of the non-tissue piercing electrodes 722 may be selected at a time to operate as a multi-point atrial cathode electrode.

Certain non-tissue piercing electrodes 722 selected for atrial pacing and/or atrial sensing may be selected based on atrial capture threshold tests, electrode impedance, P-wave signal strength in the cardiac electrical signal, or other factors. For example, a single one or any combination of two or more individual non-tissue piercing electrodes 722 functioning as a cathode electrode that provides an optimal combination of a low pacing capture threshold amplitude and relatively high electrode impedance may be selected to achieve reliable atrial pacing using minimal current drain from the power source 98.

In some instances, the distal-facing surface 738 may uniformly contact the atrial endocardial surface when the tissue-piercing electrode assembly 712 anchors the housing 730 at the implant site. In that case, all the electrodes 722 may be selected together to form the atrial cathode. Alternatively, every other one of the electrodes 722 may be selected together to form a multi-point atrial cathode having a higher electrical impedance that is still uniformly distributed along the distal-facing surface 738. Alternatively, a subset of one or more electrodes 722 along one side of the insulative distal member 772 may be selected to provide pacing at a desired site that achieves the lowest pacing capture threshold due to the relative location of the electrodes 722 to the atrial tissue being paced.

In other instances, the distal-facing surface 738 may be oriented at an angle relative to the adjacent endocardial surface depending on the positioning and orientation at which the tissue-piercing electrode assembly 712 enters the cardiac tissue. In this situation, one or more of the non-tissue piercing electrodes 722 may be positioned in contact with the adjacent endocardial tissue closer than other non-tissue piercing electrodes 722, which may be angled away from the endocardial surface. By providing multiple non-tissue piercing electrodes along the periphery of the insulative distal member 772, the angle of the tissue-piercing electrode assembly 712 and the housing distal end region 732 relative to the cardiac surface, e.g., the right-atrial endocardial surface, may not be required to be substantially parallel. Anatomical and positional differences may cause the distal-facing surface 738 to be angled or oblique to the endocardial surface, however, multiple non-tissue piercing electrodes 722 distributed along the periphery of the insulative distal member 772 increase the likelihood of good contact between one or more electrodes 722 and the adjacent cardiac tissue to promote acceptable pacing thresholds and reliable cardiac event sensing using at least a subset of multiple electrodes 722. Contact or fixation circumferentially along the entire periphery of the insulative distal member 772 may not be required.

The non-tissue piercing electrodes 722 are shown to each include a first portion 722a extending along the distal-facing surface 738 and a second portion 722b extending along the circumferential surface 739. The first portion 722a and the second portion 722b may be continuous, exposed surfaces such that the active electrode surface wraps around a peripheral edge 776 of the insulative distal member 772 that joins the distal facing surface 738 and the circumferential surface 739. The non-tissue piercing electrodes 722 may include one or more of the electrodes 722 along the distal-facing surface 738, one or more electrodes along the circumferential surface 739, one or more electrodes each extending along both of the distal-facing surface 738 and the circumferential surface 739, or any combination thereof. The exposed surface of each of the non-tissue piercing electrodes 722 may be flush with respective distal-facing surfaces 738 and/or circumferential surfaces. In other examples, each of the non-tissue piercing electrodes 722 may have a raised surface that protrudes from the insulative distal member 772. Any raised surface of the electrodes 722, however, may define a smooth or rounded, non-tissue piercing surface.

The distal fixation and electrode assembly 736 may seal the distal end region of the housing 730 and may provide a foundation on which the electrodes 722 are mounted. The electrodes 722 may be referred to as housing-based electrodes. The electrodes 722 may not be carried by a shaft or other extension that extends the active electrode portion away from the housing 730, like the distal tip electrode 742 residing at the distal tip of the helical shaft 740 extending away from the housing 730. Other examples of non-tissue piercing electrodes presented herein that are coupled to a distal-facing surface and/or a circumferential surface of an insulative distal member include the distal housing-based ring electrode 22 (FIG. 7), the distal housing-based ring electrode extending circumferentially around the assembly 36 (FIG. 7), button electrodes, other housing-based electrodes, and other circumferential ring electrodes. Any non-tissue piercing electrodes directly coupled to a distal insulative member, peripherally to a central tissue-piercing electrode, may be provided to function individually, collectively, or in any combination as a cathode electrode for delivering pacing pulses to adjacent cardiac tissue. When a ring electrode, such as the distal ring electrode 22 and/or a circumferential ring electrode, is provided, portions of the ring electrode may be electrically insulated by a coating to provide multiple distributed non-tissue piercing electrodes along the distal-facing surface and/or the circumferential surface of the insulative distal member.

The non-tissue piercing electrodes 722 and other examples listed above are expected to provide more reliable and effective atrial pacing and sensing than a tissue-piercing electrode provided along the distal fixation and electrode assembly 736. The atrial chamber walls are relatively thin compared to ventricular chamber walls. A tissue-piercing atrial cathode electrode may extend too deep within the atrial tissue leading to inadvertent sustained or intermittent capture of ventricular tissue. A tissue-piercing atrial cathode electrode may lead to interference with sensing atrial signals due to ventricular signals having a larger signal strength in the cardiac electrical signal received via tissue-piercing atrial cathode electrodes that are closer in physical proximity to the ventricular tissue. The tissue-piercing electrode assembly 712 may be securely anchored into ventricular tissue for stabilizing the implant position of the device 710 and providing reasonable certainty that the tip electrode 742 is sensing and pacing in ventricular tissue while the non-tissue piercing electrodes 722 are reliably pacing and sensing in the atrium. When the device 710 is implanted in the target implant region 4, e.g., as shown in FIG. 1 the ventricular septum, the tip electrode 742 may reach left ventricular tissue for pacing of the left ventricle while the non-tissue piercing electrodes 722 provide pacing and sensing in the right atrium. The tissue-piercing electrode assembly 712 may be in the range of about 4 to about 8 mm in length from the distal-facing surface 738 to reach left ventricular tissue. In some instances, the device 710 may achieve four-chamber pacing by delivering atrial pacing pulses from the atrial pacing circuit 83 via the non-tissue piercing electrodes 722 in the target implant region 4 to achieve bi-atrial (right and left atrial) capture and by delivering ventricular pacing pulses from the ventricular pacing circuit 85 via the tip electrode 742 advanced into ventricular tissue from the target implant region 4 to achieve biventricular (right and left ventricular) capture.

FIG. 10 shows an illustrative method 600 of detecting atrial activity, for example, using the acoustic or motion detector 11 of FIG. 5, which may be used to represent physiological response information. In particular, method 600 may include detecting an atrial contraction based on analysis of a motion signal (e.g., provided by the motion detector 11) that may be performed by an IMD implanted in the patient's heart. In some embodiments, the motion signal may be provided by an IMD implanted within a ventricle, such as the right ventricle, of the patient's heart. The method 600 may include beginning an atrial contraction detection delay period upon identification of a ventricular activation event 630. The method 600 may include beginning an atrial contraction detection window upon expiration of the atrial contraction delay period 632. The method 600 may include analyzing the motion signal within the atrial contraction detection window.

The method 600 may include filtering the motion signal within the atrial contraction detection window, rectifying the filtered signal, and generating a derivative signal of the filtered and rectified motion signal 634 within the atrial contraction detection window. The method 600 may include determining whether an amplitude of the derivative signal within the atrial contraction detection window exceeds a threshold 636. In response to determining that the amplitude of the derivative signal within the atrial contraction detection window exceeds the threshold (YES of 636), the method 600 may proceed to detecting atrial contraction 638. Otherwise (NO of 636), the method 600 may return to filtering, rectifying, and generating a derivative signal 634. Various techniques for using a motion detector that provides a motion signal may be described in U.S. Pat. No. 9,399,140 (Cho et al.), issued Jul. 26, 2016, entitled "Atrial contraction detection by a ventricular leadless pacing device for atrio-synchronous ventricular pacing," which is incorporated herein by reference in its entirety.

As will be described with respect to FIG. 11, heart sounds (HS) may be detected and used to represent physiological response information. described herein, the amplitudes and/or relative time intervals of one or more of the S1 through S4 heart sounds can be useful in optimizing a patient's hemodynamic response to CRT or other cardiac therapies that include cardiac pacing and/or neural stimulation for achieving hemodynamic benefit. The first heart sound, S1, corresponds to the start of ventricular systole. Ventricular systole begins when an action potential conducts through the atrioventricular node (AV node) and quickly depolarizes the ventricular myocardium. This event is distinguished by the QRS complex on the ECG. As the ventricles contract, the pressure in the ventricles begins to rise, causing abrupt closure of the mitral and tricuspid valves between the ventricles and atria as ventricular pressure exceeds atrial pressure. This valve closure may generate S1. S1 generally has a duration of about 150 ms and a frequency on the order of about 20 to 250 Hz. The amplitude of S1 may provide a surrogate measurement of LV contractility. Thus, an increase in S1 amplitude positively may correlate with an improvement in LV contractility. Other measures, like the pre-ejection period measured from the onset of QRS to S1, may also be used as a surrogate of myocardial contractility index.

Separation of the closure of the mitral and tricuspid valves due to ventricular dyssynchrony can be observed as separate M1 and T1 peaks in the S1 signal. Merging of the M1 (mitral valve closure sound) and the T1 (tricuspid valve closure sound) can be used as an indication of improved ventricular synchrony.

Generally, left ventricular pressure (LVP) rises dramatically following the QRS complex of the ECG and closure of the mitral valve and continues to build during ventricular systole until the aortic and pulmonary valves open, ejecting blood into the aorta and pulmonary artery. Ventricular contraction typically continues to cause blood pressure to rise in the ventricles and the aorta and pulmonary artery during the ejection phase. As the contraction diminishes, blood pressure decreases until the aortic and pulmonary valves close.

The second heart sound, S2, may be generated by the closure of the aortic and pulmonary valves, near the end of ventricular systole and start of ventricular diastole. S2 may, therefore, be correlated to diastolic pressure in the aorta and the pulmonary artery. S2 generally has a duration of about 120 ms and a frequency on the order of 25 to 350 Hz. The time interval between S1 and S2, i.e., S1-S2 time interval may represent the systolic time interval (STI) corresponding to the ventricular isovolumic contraction (pre-ejection) and ejection phase of the cardiac cycle. This S1-S2 time interval may provide a surrogate measurement for stroke volume. Furthermore, the ratio of the pre-ejection period (Q-S1) to S1-S2 time may be used as an index of myocardial contractility.

The third heart sound, S3, is associated with early, passive diastolic filling of the ventricles, and the fourth heart sound, S4, may be associated with late, active filling of the ventricles due to atrial contraction. The third sound is generally difficult to hear in a normal patient using a stethoscope, and the fourth sound is generally not heard in a normal patient. Presence of the third and fourth heart sounds during an examination using a stethoscope may indicate a pathological condition. The S3 and S4 heart sounds may be used in optimizing pace parameters as they relate to the diastolic function of the heart. Generally, these sounds would be minimized or disappear when an optimal pace parameter is identified. Other aspects of the S1 through S4 heart sounds and timing thereof that may be useful in cardiac pace-parameter optimization as known to one having ordinary skill in the art.

FIG. 11 is a flowchart 800 of a method for using heart sounds to optimize pace control parameters according to one embodiment. Methods of the present disclosure may include one or more blocks shown in flowchart 800. Other examples of using heart sounds to optimize cardiac therapy are described generally in U.S. Pat. No. 96,430,134, granted May 9, 2017, entitled "System and method for pacing parameter optimization using heart sounds," which is incorporated herein by reference in its entirety.

A pace-parameter optimization method may be initiated at block 802. The optimization process may be initiated in response to a user command received via an external programmer. At a time of initial IMD implantation or during office follow-up visits, or during a remote patient monitoring session, a user may initiate an HS-base optimization procedure using an external programmer or networked computer. Additionally, or alternatively, the process shown by flowchart 800 may be an automated process started periodically or in response to sensing a need for therapy delivery or therapy adjustment based on a sensed physiological signal, which may include sensed HS signals.

At block 804 a pace control parameter to be optimized is selected. A control parameter may be a timing-related parameter, such as an AV interval or VV interval. Pacing vector is another control parameter that may be selected at block 804 for optimization. For example, when a multi-polar lead is used, such as a coronary sinus lead, multiple bipolar or unipolar pacing vectors may be selected for pacing in a given heart chamber. The pacing site associated with a particular pacing vector may have a significant effect on the hemodynamic benefit of pacing therapy. As such, pacing vector is one pace control parameter that may be optimized using methods described herein.

A pacing sequence is initiated at block 806 using an initial parameter setting for the test parameter selected at block 804. In one embodiment, the AV interval is being optimized, and ventricular pacing is delivered at an initial AV interval setting. It is understood that an initial AV interval setting may be selected at block 806 by first measuring an intrinsic AV interval in a patient having intact AV conduction, i.e., no AV block. An initial AV interval may be a default pacing interval, the last programmed AV interval, or a minimum or maximum AV interval to be tested. Alternatively, if the VV interval is selected for optimization, an intrinsic inter-ventricular conduction time may be measured first and paced VV intervals may be iteratively adjusted beginning at a VV interval longer, shorter or approximately equal to the intrinsic VV conduction time.

An iterative process for adjusting the selected test parameter to at least two different settings is performed. The parameter may be adjusted to different settings in any desired order, e.g., increasing, decreasing, random, etc. For example, during adjustment of AV interval, an initial AV interval may be set to just longer than or approximately equal to a measured intrinsic AV conduction time then iteratively decreased down to a minimum AV interval test setting. During pacing using each pace parameter setting, HS signals are acquired at block 808. The iterative process advances to the next test parameter setting at block 812 until all test parameter settings have been applied, as determined at block 810, and HS signals have been recorded for each setting.

HS signals may be acquired for multiple cardiac cycles to enable ensemble averaging or averaging of HS parameter measurements taken from individual cardiac cycles. It is understood that amplification, filtering, rectification, noise cancellation techniques or other signal processing steps may be used for improving the signal-to-noise ratio of the HS signals and these steps may be different for each of the heart sounds being acquired, which may include any or all types of heart sounds.

At least one HS parameter measurement is determined from the recorded HS signals for each test parameter setting at block 814. The IMD processor or an external processor, e.g., included in a programmer, or a combination of both may perform the HS signal analysis described herein. In one embodiment, S1 and S2 are recorded and HS parameters are measured using the S1 and S2 signals at block 814. For example, the amplitude of S1, the V-S2 interval (where the V event may be a V pace or a sensed R-wave), and the S1-S2 interval are measured. The presence of S3 and/or S4 may additionally be noted, or measurements of these signals may be made for determining related parameters. HS signal parameters are determined for at least two different test parameter settings, e.g., at least two different AV intervals, two or more different VV intervals, or two or more different pacing vectors.

At block 818, a trend for each HS parameter determined at block 810 as a function of the pace parameter test settings is determined. In one embodiment, a trend for each of the V-S2 interval, S1 amplitude, and S1-S2 interval is determined. Other embodiments may include determining separation of the M1 and T1 sounds during the S1 signal. Based on the trends of the HS parameter(s) with respect to the varied pace control parameter, an optimal pace parameter setting may be identified automatically by the processor at block 820. Additionally, or alternatively, the HS trends are reported and displayed at block 822 on an external device such as a programmer or at a remote networked computer.

If the pace parameter being tested is, for example, pacing site or pacing vector when a multipolar electrode is positioned along a heart chamber, such as a quadripolar lead along LV, a pacing site or vector may be selected based on maximizing an HS-based surrogate for ventricular contractility. In one embodiment, the amplitude of S1 is used as a surrogate for ventricular contractility, and a pacing site or vector associated with a maximum S1 is identified at block 820 as the optimal pacing vector setting.

Determining the trend of each HS parameter at block 818 may include determining whether the V-S2 interval trend presents a sudden slope change, e.g., from a substantially flat trend to a decreasing trend. An AV interval associated with a sudden change in the V-S2 interval trend may be identified as an optimal AV interval setting. The optimal AV interval may be further identified based on other HS trends, for example, a maximum S1 amplitude and/or a maximum S1-S2 interval.

In some embodiments, an automatically-identified optimal pace parameter setting may also be automatically programmed in the IMD at block 824. In other embodiments, the clinician or user reviews the reported HS data and recommended pace parameter setting(s) and may accept a recommended setting or select another setting based on the HS data.

HS sensing module, or circuitry, may be operably coupled to the control circuit 80 (FIG. 8) and be configured to receive analog signals from an HS sensor for sensing one or more of these heart sounds. For example, the HS sensing module may include one or more "channels" configured to particularly sense a specific heart sound based on frequency, duration, and timing of the heart sounds. For example, ECG/EGM sensing circuitry may be used by the control circuit 80 to set HS sensing windows used by HS sensing module for sensing the heart sounds. HS sensing module may include one or more sense amplifiers, filters, and rectifiers for optimizing a signal to noise ratio of heart sound signals. Separate and unique amplification and filtering properties may be provided for sensing each of the S1 through S4 sounds to improve signal quality as needed.

Bioimpedance, or intracardiac impedance, may be measured and used to represent physiological response information. For example, any of the IMDs described herein may measure an intracardiac impedance signal by injecting a current and measuring a voltage between electrodes of an electrode vector configuration (e.g., selected electrodes). For example, the IMD may measure an impedance signal by injecting a current (e.g., a non-pacing threshold current) between a first electrode (e.g., RV electrode) and an electrode located in the RV proximate the tricuspid valve and measuring a voltage between the first and second electrodes. Another vector that may be used is from the LV electrode to the RV electrode. One will recognize that other vector pair configurations may be used for stimulation and measurement. Impedance can be measured between any set of electrodes that encompass the tissue or cardiac chamber of interest. Thus, one can inject current and measure voltage to calculate the impedance on the same two electrodes (a bipolar configuration) or inject current and measure the voltage on two separate pairs of electrodes (e.g., one pair for current injection and one pair for voltage sense), hence, a quadripolar configuration. For a quadripolar electrode configuration, the current injection and voltage sense electrodes may be in line with each other (or closely parallel to) and the voltage sense electrodes may be within the current sense field. For example, if one injected current between the SVC coil electrode and the RV tip electrode, voltage sensing may be between the RV coil electrode and RV ring electrode. In such embodiments, a VfA lead may be used for the LV cardiac therapy or sensing. The impedance vectors can be configured to encompass a particular anatomical area of interest, such as the atrium or ventricles.

The illustrative methods and/or devices described herein may monitor one or more electrode vector configurations. Further, multiple impedance vectors may be measured concurrently and/or periodically relative to another. In at least one embodiment, the illustrative methods and/or devices may use impedance waveforms to acquire selection data (e.g., to find applicable fiducial points, to allow extraction of measurements from such waveforms, etc.) for optimizing CRT.

As used herein, the term "impedance signal" is not limited to a raw impedance signal. It should be implied that raw impedance signals may be processed, normalized, and/or filtered (e.g., to remove artifacts, noise, static, electromagnetic interference (EMI), and/or extraneous signals) to provide the impedance signal. Further, the term "impedance signal" may include various mathematical derivatives thereof including real and imaginary portions of the impedance signal, a conductance signal based on the impedance (i.e., the reciprocal or inverse of impedance), etc. In other words, the term "impedance signal" may be understood to include conductance signals, i.e., signals that are the reciprocal of the impedance signal.

In one or more embodiments of the methods and/or devices described herein, various patient physiological parameters (e.g., intracardiac impedance, heart sounds, cardiac cycle intervals such as R-R interval, etc.) may be monitored for use in acquiring selection data to optimize CRT (e.g., set AV and/or VV delay, optimize cardiac contractility, for example, by using and/or measuring impedance first derivative dZ/dt, select pacing site, select pacing vector, lead placement, or assess pacing capture from both the electrical and mechanical points of view (e.g., electrical capture may not mean mechanical capture, and the heart sounds and impedance may assist in assessing whether the electrical stimulus captures the heart or not by looking at the mechanical information from the heart sounds and impedance), select an effective electrode vector configuration for pacing, etc.). For example, intracardiac impedance signals between two or more electrodes may be monitored for use in providing such optimization.

FIG. 12 shows one example of a method 850 for acquiring selection data for one of the device parameter options (e.g., one of the selectable device parameters that may be used to optimize CRT, such as a potential AV delay that may be an optimal parameter). Other examples of using heart sounds to optimize cardiac therapy are described generally in U.S. Pat. No. 9,707,399, granted Jul. 18, 2017, entitled "Cardiac resynchronization therapy optimization based on intracardiac impedance and heart sounds," which is incorporated herein by reference in its entirety.

As shown, pacing therapy is delivered using one of the plurality of device options (block 852) (e.g., the plurality of device parameter options may be selected, determined and/or calculated AV delays, such as percentages of intrinsic AV delay, for example, 40% of intrinsic AV delay, 50% of intrinsic AV delay, 60% of intrinsic AV delay, 70% of intrinsic AV delay, 80% of intrinsic AV delay, etc.). For the device parameter option used to pace (block 852), selection data is acquired at each of a plurality of electrode vector configurations (e.g., intracardiac impedance is monitored over a plurality of cardiac cycles, and selection data is extracted using such impedance signal). As indicated by the decision block 854, if selection data has not been acquired from all desired electrode vector configurations, then the loop of acquiring selection data (e.g., the loop illustrated by blocks 858, 860, 862, and 864) is repeated. If selection data has been acquired from all desired electrode vector configurations, then another different device parameter option is used to deliver therapy (block 856) and the method 850 of FIG. 12 is repeated (e.g., for the different device parameter option) until selection data has been acquired for all the different device parameter options (e.g., selection data being collected at each of a plurality of electrode vector configurations for each of the different device parameter options).

As shown in the repeated loop of acquiring selection data for each of the desired electrode vector configurations (e.g., blocks 858, 860, 862, and 864), one of the plurality of electrode vector configurations is selected for use in acquiring selection data (block 858). Temporal fiducial points associated with at least a part of a systolic portion of at least one cardiac cycle and/or temporal fiducial points associated with at least a part of a diastolic portion of at least one cardiac cycle for the selected electrode vector configuration are acquired (block 860) (e.g., such as with use of heart sounds, analysis of impedance signal minimum and maximums, application of algorithms based on physiological parameters such as R-R intervals, etc.). For example, temporal fiducial points associated with the systolic and/or diastolic portions of the cardiac cycle may be acquired, temporal fiducial points associated with one or more defined segments within systolic and/or diastolic portions of the cardiac cycle may be acquired, and/or temporal fiducial points within or associated with one or more points and/or portions of a systolic and/or diastolic portion of the cardiac cycle may be acquired. Yet further, for example, temporal fiducial points associated with just the systolic portion or just the diastolic portion of the cardiac cycle may be acquired, temporal fiducial points associated with one or more defined segments within just the systolic portion or just the diastolic portion of the cardiac cycle may be acquired, and/or temporal fiducial points within or associated with one or more points and/or portions of just the systolic portion or just the diastolic portion of the cardiac cycle may be acquired. In other words, fiducial points may be acquired that are associated with either both the systolic and diastolic portions of the cardiac cycle or associated with just one of such portions of the cardiac cycle. Further, for example, such fiducial points may be representative or indicative of a measurement window and/or time period (e.g., interval, point, etc.) at or during which intracardiac impedance may be measured for use in an analysis as described herein.

In about the same timeframe (e.g., about simultaneously with the acquired fiducial points), an intracardiac impedance signal is acquired at the selected electrode vector configuration (block 862). With the acquired fiducial points and the acquired intracardiac impedance signal, measurements from the impedance signal are extracted based on the temporal fiducial points (block 864) (e.g., integral of the impedance signal in a measurement window defined between fiducial points, maximum slope of impedance signal in a measurement window defined between fiducial points, time between the fiducial points, maximum impedance at a fiducial point, etc.). One or more of such measurements may be comparable to desired values for such measurements allowing for a determination of whether the measurement may indicate that the device parameter option may be an effective device parameter for optimizing therapy (e.g., a scoring algorithm may be used to determine if a device parameter option may be an optimal parameter based on whether a plurality of such measurements meet certain criteria or thresholds).

The measurement data for each of the device parameter options (e.g., obtained such as described in FIG. 12) is determined for at least one cardiac cycle. In one or more embodiments, such measurement data is acquired for a plurality of cardiac cycles. The cardiac cycles during which measurement data is acquired may be any suitable cardiac cycle. In one or more embodiments, the selected cardiac cycles during which measurement data is acquired is based on the respiratory cycle. In at least one embodiment, the measurement data is acquired during cardiac cycles occurring at the end of a respiratory cycle (e.g., proximate the end of expiration).

Figure 13:
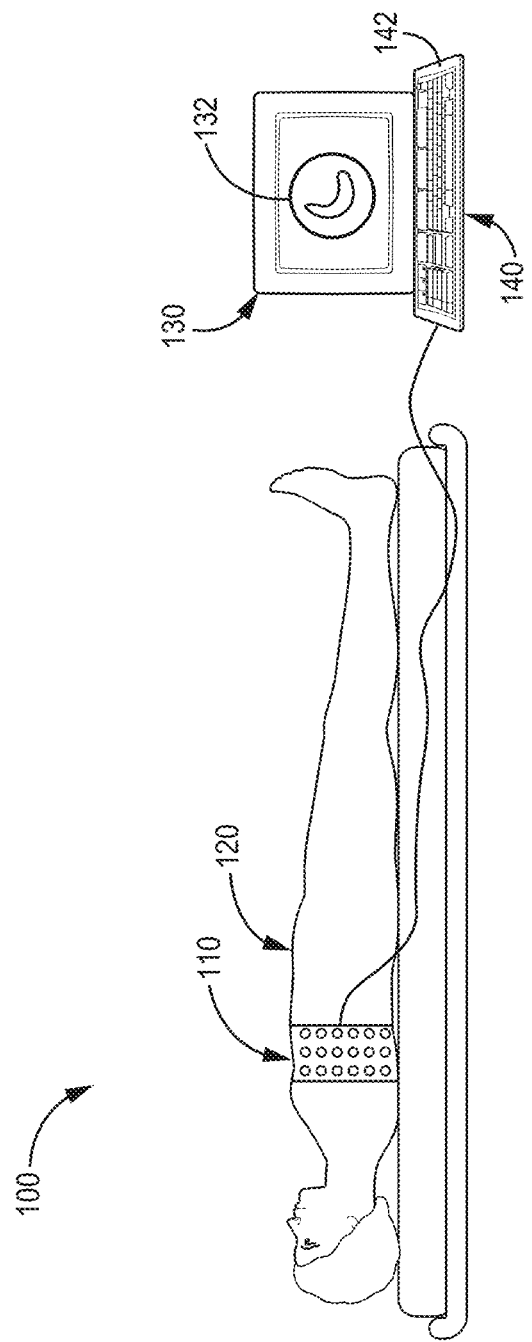
FIG. 13 is a diagram of an illustrative system including electrode apparatus, display apparatus, and computing apparatus for use with, e.g., the illustrative systems and devices of FIGS. 1-4 and FIG. 22.

FIG. 13 depicts an illustrative system 100 including electrode apparatus 110, display apparatus 130, and computing apparatus 140. The electrode apparatus 110 as shown includes a plurality of electrodes incorporated, or included, within a band wrapped around the chest, or torso, of a patient 120. The electrode apparatus 110 is operatively coupled to the computing apparatus 140 (e.g., through one or wired electrical connections, wirelessly, etc.) to provide electrical signals from each of the electrodes to the computing apparatus 140 for analysis, evaluation, etc. Illustrative electrode apparatus may be described in U.S. Pat. No. 9,320,446 entitled "Bioelectric Sensor Device and Methods" and issued on Apr. 26, 2016, which is incorporated herein by reference in its entirety. Further, illustrative electrode apparatus 110 will be described in more detail in reference to FIGS. 14-15.

Although not described herein, the illustrative system 100 may further include imaging apparatus. The imaging apparatus may be any type of imaging apparatus configured to image, or provide images of, at least a portion of the patient in a noninvasive manner. For example, the imaging apparatus may not use any components or parts that may be located within the patient to provide images of the patient except noninvasive tools such as contrast solution. It is to be understood that the illustrative systems, methods, and interfaces described herein may further use imaging apparatus to provide noninvasive assistance to a user (e.g., a physician) to calibrate and/or deliver a VfA pacing therapy, to locate and position a device to deliver VfA cardiac pacing therapy, and/or to locate or select a pacing electrode or pacing vector proximate the patient's heart for ventricle from atrium pacing therapy in conjunction with the evaluation of ventricle from atrium pacing therapy.

For example, the illustrative systems, methods, and interfaces may provide image-guided navigation that may be used to navigate leads including leadless devices, electrodes, leadless electrodes, wireless electrodes, catheters, etc., within the patient's body while also providing noninvasive cardiac therapy evaluation including determining whether a ventricle from atrium (VfA) paced setting is optimal or determining whether one or more selected parameters are optimal, such as selected location information (e.g., location information for the electrodes to target a particular location in the left ventricle). Illustrative systems and methods that use imaging apparatus and/or electrode apparatus may be described in U.S. Patent Publication No. 2014/0371832 filed on Jun. 12, 2013, and entitled "Implantable Electrode Location Selection," U.S. Patent Publication No. 2014/0371833 filed on Jun. 12, 2013, and entitled "Implantable Electrode Location Selection," U.S. Patent Publication No. 2014/0323892 filed on Mar. 27, 2014 and entitled "Systems, Methods, and Interfaces for Identifying Effective Electrodes," U.S. Patent Publication No. 2014/0323882 filed on Mar. 27, 2014 and entitled "Systems, Methods, and Interfaces for Identifying Optical-Electrical Vectors," each of which is incorporated herein by reference in its entirety.

Illustrative imaging apparatus may be configured to capture x-ray images and/or any other alternative imaging modality. For example, the imaging apparatus may be configured to capture images, or image data, using isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intravascular ultrasound (IVUS), two-dimensional (2D) ultrasound, three dimensional (3D) ultrasound, four-dimensional (4D) ultrasound, intraoperative CT, intraoperative MRI, etc. Further, it is to be understood that the imaging apparatus may be configured to capture a plurality of consecutive images (e.g., continuously) to provide video frame data. In other words, a plurality of images taken over time using the imaging apparatus may provide video frame, or motion picture, data. Additionally, the images may also be obtained and displayed in two, three, or four dimensions. In more advanced forms, four-dimensional surface rendering of the heart or other regions of the body may also be achieved by incorporating heart data or other soft tissue data from a map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data, e.g., to be used to navigate treatment apparatus proximate target locations (e.g., such as locations within the left ventricle, including a selected location within the high posterior basal and/or septal area of the left ventricular cavity) within the heart or other areas of interest.

Systems and/or imaging apparatus that may be used in conjunction with the illustrative systems and method described herein are described in U.S. Pat. App. Pub. No. 2005/0008210 to Evron et al. published on Jan. 13, 2005, U.S. Pat. App. Pub. No. 2006/0074285 to Zarkh et al. published on Apr. 6, 2006, U.S. Pat. App. Pub. No. 2011/0112398 to Zarkh et al. published on May 12, 2011, U.S. Pat. App. Pub. No. 2013/0116739 to Brada et al. published on May 9, 2013, U.S. Pat. No. 6,980,675 to Evron et al. issued on Dec. 27, 2005, U.S. Pat. No. 7,286,866 to Okerlund et al. issued on Oct. 23, 2007, U.S. Pat. No. 7,308,297 to Reddy et al. issued on Dec. 11, 2011, U.S. Pat. No. 7,308,299 to Burrell et al. issued on Dec. 11, 2011, U.S. Pat. No. 7,321,677 to Evron et al. issued on Jan. 22, 2008, U.S. Pat. No. 7,346,381 to Okerlund et al. issued on Mar. 18, 2008, U.S. Pat. No. 7,454,248 to Burrell et al. issued on Nov. 18, 2008, U.S. Pat. No. 7,499,743 to Vass et al. issued on Mar. 3, 2009, U.S. Pat. No. 7,565,190 to Okerlund et al. issued on Jul. 21, 2009, U.S. Pat. No. 7,587,074 to Zarkh et al. issued on Sep. 8, 2009, U.S. Pat. No. 7,599,730 to Hunter et al. issued on Oct. 6, 2009, U.S. Pat. No. 7,613,500 to Vass et al. issued on Nov. 3, 2009, U.S. Pat. No. 7,742,629 to Zarkh et al. issued on Jun. 22, 2010, U.S. Pat. No. 7,747,047 to Okerlund et al. issued on Jun. 29, 2010, U.S. Pat. No. 7,778,685 to Evron et al. issued on Aug. 17, 2010, U.S. Pat. No. 7,778,686 to Vass et al. issued on Aug. 17, 2010, U.S. Pat. No. 7,813,785 to Okerlund et al. issued on Oct. 12, 2010, U.S. Pat. No. 7,996,063 to Vass et al. issued on Aug. 9, 2011, U.S. Pat. No. 8,060,185 to Hunter et al. issued on Nov. 15, 2011, and U.S. Pat. No. 8,401,616 to Verard et al. issued on Mar. 19, 2013, each of which is incorporated herein by reference in its entirety.

The display apparatus 130 and the computing apparatus 140 may be configured to display and analyze data such as, e.g., electrical signals (e.g., electrocardiogram data), cardiac information representative of one or more of mechanical cardiac functionality and electrical cardiac functionality (e.g., mechanical cardiac functionality only, electrical cardiac functionality only, or both mechanical cardiac functionality and electrical cardiac functionality), etc. Cardiac information may include, e.g., electrical heterogeneity information or electrical dyssynchrony information, surrogate electrical activation information or data, etc. that is generated using electrical signals gathered, monitored, or collected, using the electrode apparatus 110. In at least one embodiment, the computing apparatus 140 may be a server, a personal computer, or a tablet computer. The computing apparatus 140 may be configured to receive input from input apparatus 142 and transmit output to the display apparatus 130. Further, the computing apparatus 140 may include data storage that may allow for access to processing programs or routines and/or one or more other types of data, e.g., for calibrating and/or delivering pacing therapy, e.g., based on at least a heartrate, for driving a graphical user interface configured to noninvasively assist a user in targeting placement of a pacing device, and/or for evaluating pacing therapy at that location (e.g., the location of an implantable electrode used for pacing, the location of pacing therapy delivered by a particular pacing vector, etc.).

The computing apparatus 140 may be operatively coupled to the input apparatus 142 and the display apparatus 130 to, e.g., transmit data to and from each of the input apparatus 142 and the display apparatus 130. For example, the computing apparatus 140 may be electrically coupled to each of the input apparatus 142 and the display apparatus 130 using, e.g., analog electrical connections, digital electrical connections, wireless connections, bus-based connections, network-based connections, internet-based connections, etc. As described further herein, a user may provide input to the input apparatus 142 to manipulate, or modify, one or more graphical depictions displayed on the display apparatus 130 and to view and/or select one or more pieces of information related to the cardiac therapy.

Although as depicted the input apparatus 142 is a keyboard, it is to be understood that the input apparatus 142 may include any apparatus capable of providing input to the computing apparatus 140 for performing the functionality, methods, and/or logic described herein. For example, the input apparatus 142 may include a mouse, a trackball, a touchscreen (e.g., capacitive touchscreen, a resistive touchscreen, a multi-touch touchscreen, etc.), etc. Likewise, the display apparatus 130 may include any apparatus capable of displaying information to a user, such as a graphical user interface 132 including cardiac information, textual instructions, graphical depictions of electrical activation information, graphical depictions of anatomy of a human heart, images or graphical depictions of the patient's heart, graphical depictions of a leadless pacing device used to calibrate and/or deliver pacing therapy, e.g., based on at least a measured heartrate, graphical depictions of a leadless pacing device being positioned or placed to provide VfA pacing therapy, graphical depictions of locations of one or more electrodes, graphical depictions of a human torso, images or graphical depictions of the patient's torso, graphical depictions or actual images of implanted electrodes and/or leads, etc. Further, the display apparatus 130 may include a liquid crystal display, an organic light-emitting diode screen, a touchscreen, a cathode ray tube display, etc.

The processing programs or routines stored and/or executed by the computing apparatus 140 may include programs or routines for computational mathematics, matrix mathematics, dispersion determinations (e.g., standard deviations, variances, ranges, interquartile ranges, mean absolute differences, average absolute deviations, etc.), filtering algorithms, maximum value determinations, minimum value determinations, threshold determinations, moving windowing algorithms, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, comparison algorithms, vector mathematics, or any other processing required to implement one or more illustrative methods and/or processes described herein. Data stored and/or used by the computing apparatus 140 may include, for example, electrical signal/waveform data from the electrode apparatus 110, dispersions signals, windowed dispersions signals, parts or portions of various signals, electrical activation times from the electrode apparatus 110, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, cardiac information, etc.), or any other data that may be necessary for carrying out the one and/or more processes or methods described herein.

In one or more embodiments, the illustrative systems, methods, and interfaces may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform the functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high-level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the illustrative systems, methods, and/or interfaces may be implemented using a computer readable storage medium, configured with a computer program, where the storage medium so configured causes the computer to operate in a specific and predefined manner to perform functions described herein. Further, in at least one embodiment, the illustrative systems, methods, and/or interfaces may be described as being implemented by logic (e.g., object code) encoded in one or more non-transitory media that includes code for execution and, when executed by a processor, is operable to perform operations such as the methods, processes, and/or functionality described herein.

The computing apparatus 140 may be, for example, any fixed or mobile computer system (e.g., a controller, a microcontroller, a personal computer, minicomputer, tablet computer, etc.) and may be generally described as including processing circuitry. The exact configuration of the computing apparatus 140 is not limiting, and essentially any device capable of providing suitable computing capabilities and control capabilities (e.g., graphics processing, etc.) may be used. As described herein, a digital file may be any medium (e.g., volatile or non-volatile memory, a CD-ROM, a punch card, magnetic recordable medium such as a disk or tape, etc.) containing digital bits (e.g., encoded in binary, trinary, etc.) that may be readable and/or writeable by computing apparatus 140 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

Figure 14:
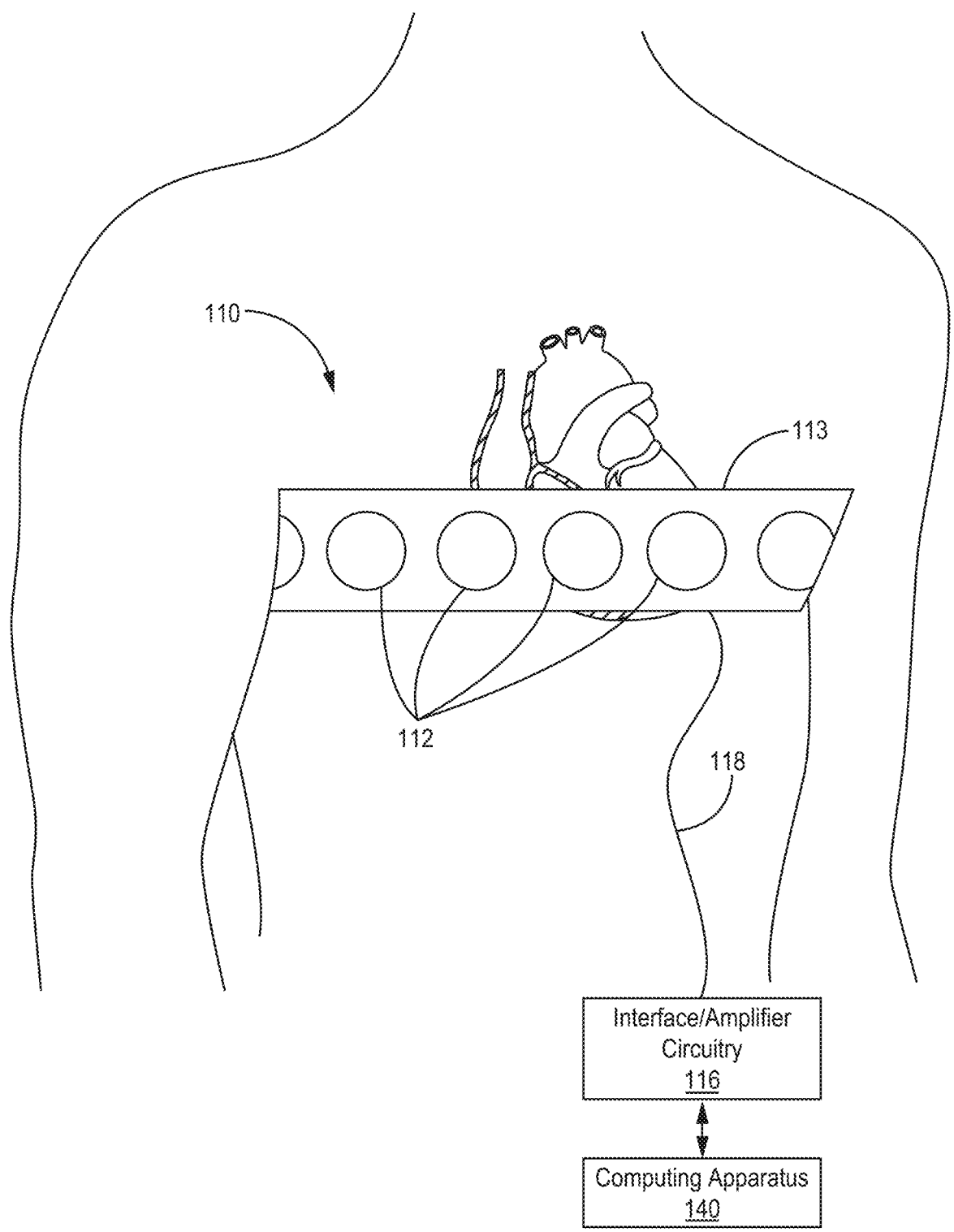
FIGS. 14-15 are diagrams of illustrative external electrode apparatus for measuring torso-surface potentials for use with, e.g., the illustrative systems and devices of FIGS. 1-4 and FIG. 22.
Figure 15:
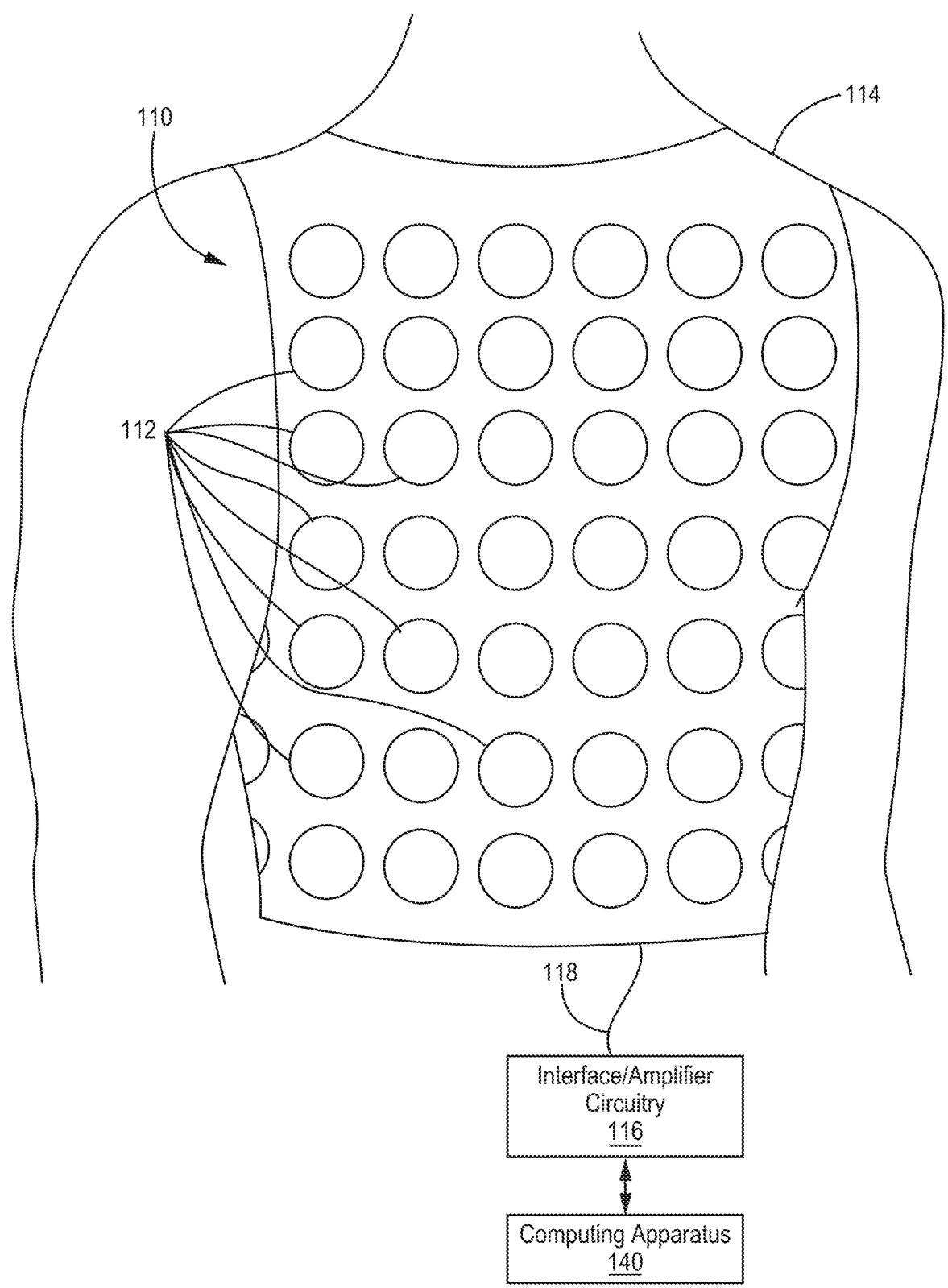

Electrical activation times of the patient's heart may be useful to evaluate a patient's cardiac condition and/or to calibrate, deliver, or evaluate ventricle from atrium (VfA) cardiac therapy to be or being delivered to a patient. Surrogate electrical activation information or data of one or more regions of a patient's heart may be monitored, or determined, using electrode apparatus 110 as shown in FIGS. 13-15. The illustrative electrode apparatus 110 may be configured to measure body-surface potentials of a patient 120 and, more particularly, torso-surface potentials of a patient 120.

As shown in FIG. 14, the illustrative electrode apparatus 110 may include a set, or array, of electrodes 112, a strap 113, and interface/amplifier circuitry 116. In at least one embodiment, a portion of the set of electrodes may be used wherein the portion corresponds to a particular location on the patient's heart. The electrodes 112 may be attached, or coupled, to the strap 113, and the strap 113 may be configured to be wrapped around the torso of a patient 120 such that the electrodes 112 surround the patient's heart. As further illustrated, the electrodes 112 may be positioned around the circumference of a patient 120, including the posterior, lateral, posterolateral, anterolateral, and anterior locations of the torso of a patient 120.

Further, the electrodes 112 may be electrically connected to interface/amplifier circuitry 116 via wired connection 118. The interface/amplifier circuitry 116 may be configured to amplify the signals from the electrodes 112 and provide the signals to the computing apparatus 140. Other illustrative systems may use a wireless connection to transmit the signals sensed by electrodes 112 to the interface/amplifier circuitry 116 and, in turn, the computing apparatus 140, e.g., as channels of data. For example, the interface/amplifier circuitry 116 may be electrically coupled to each of the computing apparatus 140 and the display apparatus 130 using, e.g., analog electrical connections, digital electrical connections, wireless connections, bus-based connections, network-based connections, internet-based connections, etc.

Although in the example of FIG. 14 the electrode apparatus 110 includes a strap 113, in other examples any of a variety of mechanisms, e.g., tape or adhesives, may be employed to aid in the spacing and placement of electrodes 112. In some examples, the strap 113 may include an elastic band, strip of tape, or cloth. In other examples, the electrodes 112 may be placed individually on the torso of a patient 120. Further, in other examples, electrodes 112 (e.g., arranged in an array) may be part of, or located within, patches, vests, and/or other manners of securing the electrodes 112 to the torso of the patient 120.

The electrodes 112 may be configured to surround the heart of the patient 120 and record, or monitor, the electrical signals associated with the depolarization and repolarization of the heart after the signals have propagated through the torso of a patient 120. Each of the electrodes 112 may be used in a unipolar configuration to sense the torso-surface potentials that reflect the cardiac signals. The interface/amplifier circuitry 116 may also be coupled to a return or indifferent electrode (not shown) that may be used in combination with each electrode 112 for unipolar sensing. In some examples, there may be about 12 to about 50 electrodes 112 spatially distributed around the torso of the patient. Other configurations may have more or fewer electrodes 112.

The computing apparatus 140 may record and analyze the electrical activity (e.g., torso-surface potential signals) sensed by electrodes 112 and amplified/conditioned by the interface/amplifier circuitry 116. The computing apparatus 140 may be configured to analyze the signals from the electrodes 112 to provide as anterior and posterior electrode signals and surrogate cardiac electrical activation times, e.g., representative of actual, or local, electrical activation times of one or more regions of the patient's heart as will be further described herein. The computing apparatus 140 may be configured to analyze the signals from the electrodes 112 to provide as anterior-septal electrode signals and surrogate cardiac electrical activation times, e.g., representative of actual, or local, electrical activation times of one or more anterior-septal regions of the patient's heart, as will be further described herein, e.g., for use in calibrating, delivering, and/or evaluating VfA pacing therapy. Further, the electrical signals measured at the left anterior surface location of a patient's torso may be representative, or surrogates, of electrical signals of the left anterior left ventricle region of the patient's heart, electrical signals measured at the left lateral surface location of a patient's torso may be representative, or surrogates, of electrical signals of the left lateral left ventricle region of the patient's heart, electrical signals measured at the left posterolateral surface location of a patient's torso may be representative, or surrogates, of electrical signals of the posterolateral left ventricle region of the patient's heart, and electrical signals measured at the posterior surface location of a patient's torso may be representative, or surrogates, of electrical signals of the posterior left ventricle region of the patient's heart. In one or more embodiments, measurement of activation times can be performed by measuring the period of time between an onset of cardiac depolarization (e.g., onset of QRS complex) and an appropriate fiducial point such as, e.g., a peak value, a minimum value, a minimum slope, a maximum slope, a zero crossing, a threshold crossing, etc.

Additionally, the computing apparatus 140 may be configured to provide graphical user interfaces depicting the surrogate electrical activation times obtained using the electrode apparatus 110. Illustrative systems, methods, and/or interfaces may noninvasively use the electrical information collected using the electrode apparatus 110 to evaluate a patient's cardiac condition and/or to calibrate, deliver, or evaluate VfA pacing therapy to be or being delivered to the patient.

FIG. 15 illustrates another illustrative electrode apparatus 110 that includes a plurality of electrodes 112 configured to surround the heart of the patient 120 and record, or monitor, the electrical signals associated with the depolarization and repolarization of the heart after the signals have propagated through the torso of the patient 120. The electrode apparatus 110 may include a vest 114 upon which the plurality of electrodes 112 may be attached, or to which the electrodes 112 may be coupled. In at least one embodiment, the plurality, or array, of electrodes 112 may be used to collect electrical information such as, e.g., surrogate electrical activation times.

Similar to the electrode apparatus 110 of FIG. 14, the electrode apparatus 110 of FIG. 13 may include interface/amplifier circuitry 116 electrically coupled to each of the electrodes 112 through a wired connection 118 and be configured to transmit signals from the electrodes 112 to computing apparatus 140. As illustrated, the electrodes 112 may be distributed over the torso of a patient 120, including, for example, the anterior, lateral, posterolateral, anterolateral, and posterior surfaces of the torso of the patient 120.

The vest 114 may be formed of fabric with the electrodes 112 attached to the fabric. The vest 114 may be configured to maintain the position and spacing of electrodes 112 on the torso of the patient 120. Further, the vest 114 may be marked to assist in determining the location of the electrodes 112 on the surface of the torso of the patient 120. In one or more embodiments, the vest 114 may include about 17 or more anterior electrodes positionable proximate the anterior torso of the patient, and about 39 or more posterior electrodes positionable proximate the anterior torso of the patient. In some examples, there may be about 25 electrodes 112 to about 256 electrodes 112 distributed around the torso of the patient 120, though other configurations may have more or fewer electrodes 112.

As described herein, the electrode apparatus 110 may be configured to measure electrical information (e.g., electrical signals) representing different regions of a patient's heart. For example, activation times of different regions of a patient's heart can be approximated from surface electrocardiogram (ECG) activation times measured using surface electrodes in proximity to surface areas corresponding to the different regions of the patient's heart. In at least one example, activation times of the anterior-septal region of a patient's heart can be approximated from surface ECG activation times measured using surface electrodes in proximity to surface areas corresponding to the anterior-septal region of the patient's heart. That is, a portion of the set of electrodes 112, and not the entire set, can be used to generate activation times corresponding to a particular location of the patient's heart that the portion of the set of electrodes corresponds to.

The illustrative systems, methods, and interfaces may be used to provide noninvasive assistance to a user in the evaluation of a patient's cardiac health or status, and/or the evaluation of cardiac therapy such as ventricle from atrium (VfA) pacing therapy by use of the electrode apparatus 110 (e.g., cardiac therapy being presently-delivered to a patient during implantation or after implantation). Further, the illustrative systems, methods, and interfaces may be used to assist a user in the configuration, or calibration, of the cardiac therapy, such as VfA pacing therapy, to be or being delivered to a patient (e.g., based on a measured heartrate).

VfA pacing can be described as providing a synchronized homogeneous activation of ventricles of the heart. As an example, patients with atrial-ventricular (AV) block or prolonged AV timings that can lead to heart failure who have otherwise intact (e.g., normal) QRS can benefit from VfA pacing therapy. In addition, as an example, VfA pacing may provide beneficial activation for heart failure patients with intrinsic ventricular conduction disorders. Further, proper placement of VfA pacing can provide optimal activation of the ventricles for such patients. Further, left ventricular (LV) resynchronization for heart failure patients with left bundle branch block (LBBB) may find that VfA pacing enables easier access to left ventricular endocardium without exposing the leadless device or lead to the endocardial blood pool. At the same time, in that example, this can help engage part of the conduction system to potentially correct LBBB and effectively resynchronize the patient.

Electrical activity may be monitored using a plurality of external electrodes, such as electrodes 112 of FIGS. 13-15. The electrical activity can be monitored by a plurality of electrodes during VfA pacing therapy or in the absence of VfA pacing therapy. The monitored electrical activity can be used to evaluate VfA pacing therapy to a patient. The electrical activity monitored using the ECG belt described can be used to evaluate at least one paced setting of the VfA pacing therapy on the heart. As an example, a paced setting can be any one parameter or a combination of parameters including, but not limited to, electrode position, pacing polarity, pacing output, pacing pulse width, timing at which VfA pacing is delivered relative to atrial (A) timing, pacing rate, etc. Further, as an example, the location of the leadless device or a pacing lead can include a location in the left ventricle, accessed through the right atrium within, or in close proximity to, the high posterior basal and/or septal (HPBS) area of the left ventricular cavity. Moreover, pacing in, or in close proximity to, the HPBS area can be selective (e.g., involving stimulation of a particular area of the HPBS alone) or non-selective (e.g., combined pacing at the location of the HPBS and other atrial and/or ventricular septum areas).

Further, body-surface isochronal maps of ventricular activation can be constructed using the monitored electrical activity during VfA pacing therapy or in the absence of VfA pacing therapy. The monitored electrical activity and/or the map of ventricular activation can be used to generate electrical heterogeneity information (EHI). The electrical heterogeneity information can include determining metrics of electrical heterogeneity. The metrics of electrical heterogeneity can include a metric of standard deviation of activation times (SDAT) of electrodes on a left side of a torso of the patient and/or a metric of mean left ventricular activation time (LVAT) of electrodes on the left side of the torso of the patient. A metric of LVAT may be determined from electrodes on both the anterior and posterior surfaces, which are more proximal to the left ventricle. The metrics of electrical heterogeneity information can include a metric of mean right ventricular activation time (RVAT) of electrodes on the right side of the torso of the patient. A metric of RVAT may be determined from electrodes on both the anterior and posterior surfaces which are more proximal to the right ventricle. The metrics of electrical heterogeneity can include a metric of mean total activation time (mTAT) taken from a plurality of electrode signals from both sides of the torso of the patient, or it may include other metrics (e.g., standard deviation, interquartile deviations, a difference between a latest activation time and earliest activation time) reflecting a range or dispersion of activation times on a plurality of electrodes located on the right side of the patient torso or left side of the patient torso, or combining both right and left sides of the patient torso. The metrics of electrical heterogeneity information can include a metric of anterior-septal activation times (ASAT) of electrodes on the torso in close proximity to the anterior-septal portion of the heart.

Electrical heterogeneity information (EHI) may be generated during delivery of VfA pacing therapy at one or more VfA paced settings. The electrical heterogeneity information can be generated using metrics of electrical heterogeneity. As an example, the metrics of electrical heterogeneity can include one or more of an SDAT, an LVAT, an RVAT, an mTAT, and an ASAT. In at least one embodiment, only ASAT may be determined and further used, and/or ASAT may be more heavily weighted than other values.

One or more paced settings associated with the VfA pacing therapy may be evaluated. A paced setting can include a plurality of pacing parameters. The plurality of pacing parameters can be optimal if the patient's cardiac condition improves, if the VfA pacing therapy is effectively capturing a desired portion of the left ventricle (e.g., the high posterior basal and/or septal area), and/or if a metric of electrical heterogeneity improves by a certain threshold compared to a baseline rhythm or therapy. In at least one embodiment, the determination of whether the paced setting is optimal can be based on at least one metric of electrical heterogeneity generated from electrical activity during VfA pacing (and also, in some embodiments, during native conduction, or in the absence of VfA pacing). The at least one metric can include one or more of an SDAT, an LVAT, an RVAT, an mTAT, and an ASAT.

Further, the plurality of pacing parameters can be optimal if a metric of electrical heterogeneity is greater than or less than a particular threshold, and/or if the location of the pacing therapy to excite the left ventricle causes a particular pattern of excitation of the muscle fibers in the heart. In addition, the plurality of pacing parameters can be optimal if a metric of electrical heterogeneity indicates a correction of a left bundle branch block (LBBB), and/or if a metric of electrical heterogeneity indicates a complete engagement of a Purkinje system, etc. As an example, a metric of electrical heterogeneity of an ASAT less than or equal to a threshold (e.g., a threshold of 30 ms) and an LVAT less than or equal to a threshold (e.g., a threshold of 30 ms) can indicate a correction of an LBBB, and thus, the paced setting is optimal. As an example, a metric of electrical heterogeneity of an RVAT less than or equal to a threshold (e.g., a threshold of 30 ms), an ASAT less than or equal to a threshold (e.g., a threshold of 30 ms), and an LVAT less than or equal to a threshold (e.g., a threshold of 30 ms) can indicate a complete engagement of the Purkinje system, and thus the paced setting is may be optimal.

The paced setting can be determined to be optimal in response to the VfA pacing therapy using the paced setting being acceptable, being beneficial, being indicative of complete engagement of patient's native cardiac conduction system, being indicative of correction of a ventricular conduction disorder (e.g., left bundle branch block), etc. A paced setting can include one or more of a pacing electrode position (including one or more of a depth, an angle, an amount of turn for a screw-based fixation mechanism, etc.), a voltage, a pulse width, an intensity, a pacing polarity, a pacing vector, a pacing waveform, a timing of the pacing delivered relative to an intrinsic or paced atrial event or relative to the intrinsic His bundle potential, and/or a pacing location, etc. A pacing vector can include any two or more pacing electrodes such as, e.g., a tip electrode to a can electrode, a tip electrode to a ring electrode etc., that are used to deliver the VfA pacing therapy, etc. The pacing location can refer to the location of any of the one or more pacing electrodes that are positioned using a lead, a leadless device, and/or any device or apparatus configured to deliver VfA.

A paced setting for VfA pacing therapy may be adjusted. In at least one embodiment, the paced setting can be adjusted in response to the paced setting being not optimal. In at least one embodiment, the paced setting can be adjusted in response to the paced setting being within an optimal range but in order to determine whether the paced setting can be at a position within the optimal range that is more beneficial, more useful, more functional, etc., for the VfA pacing therapy. The paced setting could be adjusted to find the most optimal metric of electrical heterogeneity.

In one or more embodiments, a determination of whether the paced setting is optimal can be based on a particular metric of electrical heterogeneity using an ECG belt. In at least one example, the paced setting can be adjusted at intervals that correlate with a change in the metric of electrical heterogeneity until the metric of electrical heterogeneity is at or proximate a particular metric value. For instance, the adjusting of the paced setting can cause the metric of electrical heterogeneity to approach a particular threshold metric of electrical heterogeneity and, as the metric approaches the particular threshold, the rate at which the paced setting is adjusted can be slowed down. Put another way, as the metric of electrical heterogeneity is further from the particular threshold metric, the paced setting can be adjusted more quickly and as the metric of electrical heterogeneity gets closer to the particular threshold metric, the paced setting can be adjusted more slowly until the metric of electrical heterogeneity is at the particular threshold metric.

Various techniques for utilizing an electrode apparatus having a plurality of external electrodes to monitor electrical activity from tissue of a patient that may be used with the devices, systems, and methods described herein are disclosed in U.S. patent application Ser. No. 15/934,517, filed 23 Mar. 2018, entitled "Evaluation of Ventricle from Atrium Pacing Therapy," which is incorporated herein by reference in its entirety.

Figure 16:
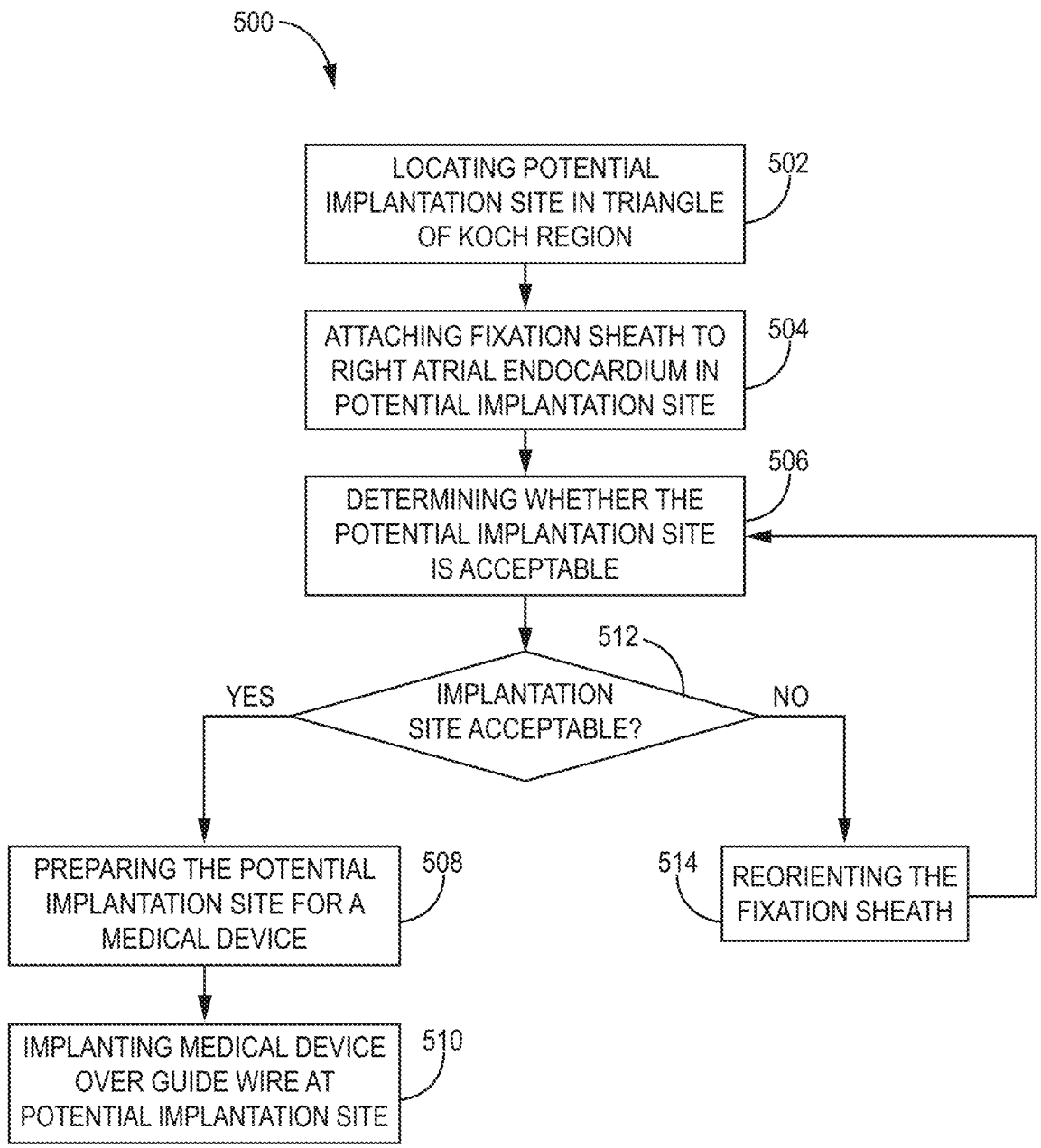
FIG. 16 is a conceptual diagram of an illustrative method for delivering a VfA medical device for use with, e.g., the illustrative systems and devices of FIGS. 1-4, 13-15, and 22.

FIG. 16 shows an illustrative method 500 for delivering a VfA medical device. The method 500 may begin with locating a potential implantation site in the triangle of Koch region in the right atrium of a patient's heart 502. In response to locating the potential implantation site, the method 500 may include attaching a fixation sheath to the right atrial endocardium in the potential implantation site 504. The fixation sheath may include a fixation element, such as a helix, that may be attachable to the right-atrial endocardium. The fixation sheath may provide a robust anchor for implanting a medical device after finding an optimal orientation using an electrical probe, such as a flexible needle. The method 500 may further include implanting the medical device over a guide wire at the potential implantation site 510.

The method 500 may include determining whether the potential implantation site is acceptable 506. If the potential implantation site is acceptable 512, the method 500 may include preparing the potential implantation site for a medical device 508 in response to determining that the potential implantation site is acceptable. In some embodiments, the medical device may be implanted 510 after preparing the potential implantation site 508.

If the potential implantation site is not acceptable 512, the method 500 may include reorienting the fixation sheath 514, for example, in an attempt to find an optimal orientation for implanting a medical device used for cardiac therapy. For example, the fixation sheath may be re-aimed by pushing, pulling, or twisting the sheath to create a new trajectory of the needle out of the sheath.

Implanting the device 510 may include implanting one or more of a right-atrial electrode, a left-ventricular electrode, and an intracardiac medical device. The intracardiac medical device may include one or more electronic components described with respect to the leadless medical devices described hereinabove (see FIG. 1). In some embodiments, the left-ventricular electrode may be coupled to a leadlet. The leadlet may be coupled to an intracardiac medical device. Both the leadlet and the intracardiac medical device may be implanted concurrently. For example, the same guide wire may be used to guide both the leadlet and the intracardiac medical device. In some embodiments, the intracardiac housing may be attached to a receptacle that may be used to push the intracardiac housing toward the implantation site. A guide wire may be coupled to the receptacle, for example, using a side sheath. The guide wire may be used to guide the leadlet, for example, in front of the intracardiac housing toward the implantation site.

The left-ventricular electrode of the medical device may be implanted from the triangle of Koch region of the right atrium through the right atrial endocardium and central fibrous body to deliver cardiac therapy to or sense electrical activity of the left ventricle in the basal and/or septal region of the left ventricular myocardium of a patient's heart. In some embodiments, the left-ventricular electrode may be disposed on a flexible or semi-rigid lead or leadlet. In other embodiments, the left-ventricular electrode may be the same as the tissue-piercing electrode.

The right-atrial electrode of the medical device may be positioned to deliver cardiac therapy to or sense electrical activity of the right atrium of the patient's heart. For example, the right-atrial electrode may contact the surface of the septal wall in the right atrium. The left-ventricular electrode may extend into, or past, the septal wall toward the left ventricle or even into the left ventricle.

Figure 17:
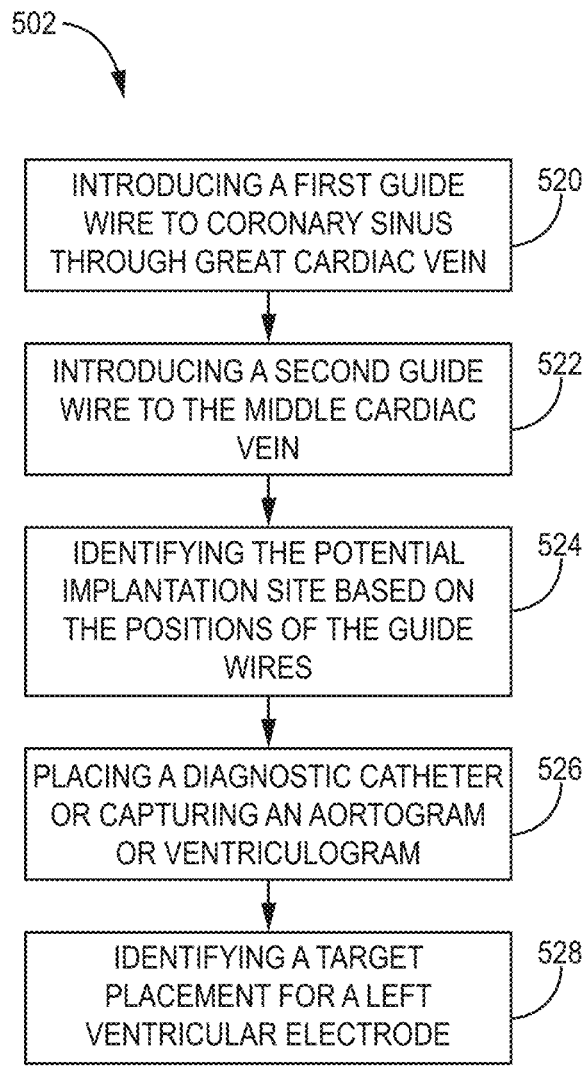
FIG. 17 is a conceptual diagram of an illustrative method for locating a potential implantation site in the triangle of Koch region for use in, e.g., the method of FIG. 16.

FIG. 17 shows an illustrative method 502 for locating a potential implantation site in the triangle of Koch region. The method 502 may include introducing a first guide wire to the coronary sinus of the patient's heart through great cardiac vein 520 (e.g., to the apex). The method 502 may also include introducing a second guide wire to the middle cardiac vein of the patient's heart 522. In some embodiments, the intersection of the first and second guide wires may provide a general vicinity for locating the triangle of Koch region. The method 500 may further include identifying the potential implantation site based on a position of the first guide wire relative to the position of the second guide wire 524. Although guide wires are described, other elongate elements may be used to traverse to the coronary sinus of the patient's heart or through the middle cardiac vein, such as a sheath or a lead.

Once the general vicinity of the triangle of Koch region is identified, the method 502 may include placing a diagnostic catheter retrograde aortic to the non-coronary cusp of the aortic valve of the patient's heart or capturing an aortogram of ventriculogram 526. In some embodiments, a cranial-caudal angle may be identified that provides the most, or close to the most, perpendicular view of a valve plane in a DV view and a most, or close to the most, parallel view in a lateral view. The method 502 may also include identifying a target placement for a left-ventricular electrode based on, or relative to, the position of the diagnostic catheter or the position of the aortic valve identified in the aortogram or the ventriculogram using the cranial-caudal angle 528.

In some embodiments, the tip of the diagnostic catheter may be used as a target reference in both parallel and perpendicular views of a valve plane. The target reference may be used for inserting a pacing electrode of a medical device at the potential implantation site. For example, the pacing electrode may be aimed about 1-2 cm below the tip of the diagnostic catheter during implantation.

In some embodiments, a target placement may be identified relative to the position of the aortic valve based on capturing an aortogram or ventriculogram using parallel and perpendicular views of the valve plane. For example, an aortogram or LV ventriculogram may be captured from both the DV view and the lateral view using the determined cranial-caudal angle.

Figure 18:
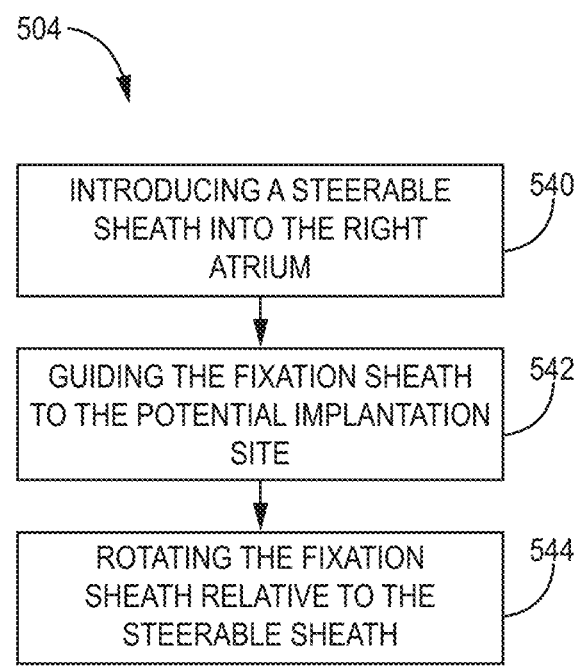
FIG. 18 is a conceptual diagram of an illustrative method for attaching a fixation sheath to the right-atrial endocardium in a potential implantation site for use in, e.g., the method of FIG. 16.

FIG. 18 shows an illustrative method 504 for attaching the fixation sheath to the right-atrial endocardium in a potential implantation site. The method 504 may include introducing a steerable sheath, which may be described as a flexcath, into the right atrium of the patient's heart 540. Although a steerable sheath is described, any suitable steerable element may be used to direct the fixation sheath to the potential implantation site. The method 504 may include guiding the fixation sheath to the potential implantation site 542, for example, when the fixation sheath is at least partially disposed in the steerable sheath. In some embodiments, once the steerable sheath is in the right atrium, a curve of the steerable sheath may be pulled, so a distal end of the steerable sheath is positioned near the coronary sinus (CS) ostium. A distal end portion (e.g., the last inch) may be pointing more apical in the lateral view and at the aorta in the DV view. Both the lateral view and the DV view may be used to ensure proper directionality of the fixation sheath.

The method 504 may also include rotating the fixation sheath relative to the steerable sheath, for example, when the fixation sheath includes a helical fixation element 544. The fixation sheath may be coupled to the steerable sheath in a manner such that the fixation sheath is freely rotatable relative to the steerable sheath.

Before rotating the fixation sheath, the fixation sheath may be advanced distally out of the steerable sheath to engage the tissue of the right-atrial endocardium. In some embodiments, contrast may be used to facilitate engagement between the fixation sheath and the tissue.

Figure 19:
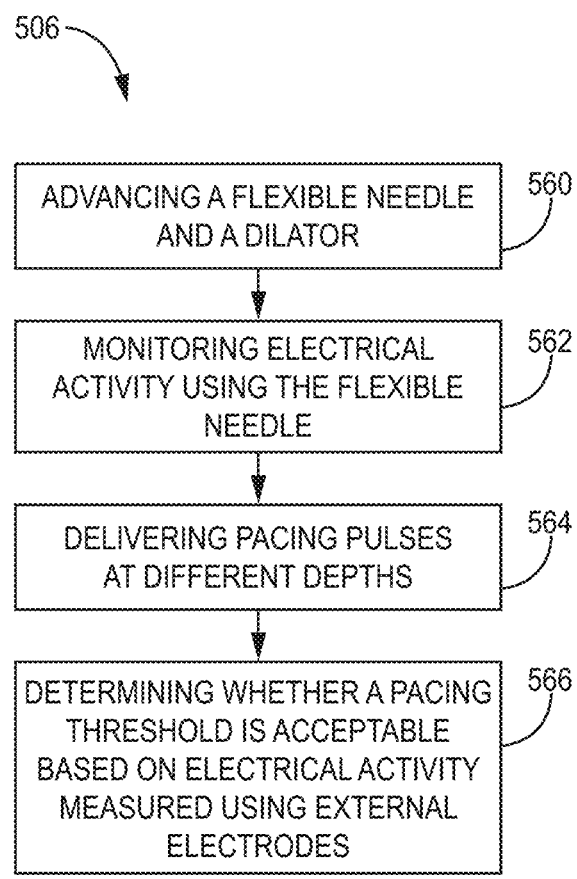
FIG. 19 is a conceptual diagram of an illustrative method for determining whether a potential implantation site is acceptable for use in, e.g., the method of FIG. 16.

FIG. 19 shows an illustrative method 506 for determining whether the potential implantation site is acceptable. The method 506 may include advancing a flexible needle and a dilator relative to the fixation sheath to engage tissue in the potential implantation site 560. In general, the flexible needle and the dilator may be disposed at least partially in the fixation sheath. In some embodiments, the flexible needle may be advanced to extend a few millimeters beyond the end of the dilator. In some embodiments, a torquer tool used on the needle proximal end portion and lock the tool, so the dilator is at a point where the needle is about 2-3 mm distal to the end of the dilator. The dilator and flexible needle assembly may be advanced until the needle touches the tissue.

The method 506 may include monitoring electrical activity using the flexible needle 562. In some embodiments, an electrogram (EGM) may be recorded using the needle. The method 506 may also include delivering pacing pulses at different depths between the right atrium and the left ventricle 564. In some embodiments, the flexible needle may be used to deliver pacing pulses, and the electrical activity may be monitored using a plurality of external electrodes, such as a 12-lead electrocardiogram (ECG).

The method 506 may also include determining whether a pacing threshold is acceptable based on electrical activity measured using a plurality of external electrodes (e.g., using an ECG belt or vest) in response to delivering pacing pulses 566. For example, activation patterns may be checked using measurements of electrical activity made with an ECG belt or vest. In some embodiments, the flexible needle and dilator may be advanced until the flexible needle reaches the LV chamber. The flexible needle may be pulled back until the flexible needle begins to pace the tissue. A pacing threshold may be recorded at this point. If the threshold is poor, the flexible needle may be pulled back. The diagnostic catheter, if present, may be moved. The steerable sheath may be re-aimed toward the target placement for the left ventricular electrode (e.g., toward the diagnostic catheter). The method 506 may return to blocks 560, 562, 564, and 566. If the threshold is acceptable, the method 506 may end, and a method to prepare the potential implantation site 508 for a medical device may begin.

Figure 20:
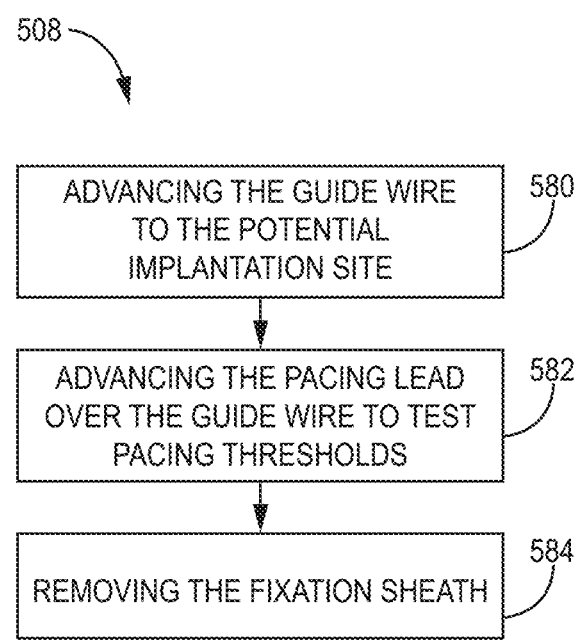
FIG. 20 is a conceptual diagram of an illustrative method for preparing a potential implantation site for a medical device for use in, e.g., the method of FIG. 16.

FIG. 20 shows an illustrative method 508 for preparing the potential implantation site for a medical device for use. The method 508 may include advancing the guide wire into the potential implantation site 580. In some embodiments, the guide wire may be advanced further into the LV tissue and/or chamber. In some embodiments, the flexible needle and steerable sheath may be removed before, during, or after advancing the guide wire. The method 508 may include advancing a pacing lead over the guide wire to test pacing thresholds 582. The pacing lead may be used to test pacing thresholds. The method 508 may include removing the fixation sheath before, during, or after advancing the pacing lead over the guide wire 584. In some embodiments, the fixation sheath may be removed after testing the pacing thresholds. In some embodiments, before a medical device is advanced for implantation over or along the guide wire, all sheaths may be removed, leaving only the guide wire in the implantation site.

In some embodiments, the fixation sheath may be removed before a pacing lead is attached to the guide wire. This may facilitate the ease of getting the sheath off the lead after the lead is implanted.

In one embodiment, a medical device delivery method of the present disclosure may follow this general procedure, which uses a diagnostic catheter:
1. Place a guide wire deep in the CS and down the great cardiac vein to the apex. This wire provides guidance as to the location of the CS ostium and shows the valve plane.
2. Place another wire in the middle cardiac vein.
3. The crossing of these two wires is the approximate place to attach the helix sheath.
4. Place a diagnostic catheter retrograde aortic to the non-coronary cusp of the aortic valve. The tip of this catheter is a target for the pacing electrode. The aim should be one or two centimeters below the tip of this catheter.
5. Place a flexcath catheter in the atrium and pull the curve, so the tip of the catheter is near the CS ostium, and the last inch of the catheter is pointing at the diagnostic tip in the LV endocardium. Use both lateral and DV to assure proper directionality of the sheath.
6. Guide the inner sheath with the attached helix to the tip of the flexcath. Engage the helix into the tissue adjacent the tip of the flexcath. Use contrast as necessary.
7. Advance the flexible needle a few millimeters outside of the dilator. Put a torquer tool on the needle proximal end and lock it at a point at which the needle is about 2-3 mm distal to the end of the dilator.
8. Advance the dilator/needle combination until the needle touches the tissue. Record the EGM from the needle.
9. Pace through the needle and record the 12-lead ECG on the Pruka.
10. Advance the dilator/needle a few mm at a time and record paced and intrinsic beats on the 12-lead ECG.
11. When the dilator needle reaches the LV chamber, pull back the dilator/needle until it just begins to pace the tissue. Record the pacing threshold at this point.
12. If there is a poor threshold, pull back needle and wire, move diagnostic catheter, re-aim the flexcath toward the diagnostic catheter, and go back to step 8.
13. If there is a good threshold, then push wire deeper into LV, remove needle, and sheath.
14. Place pacing lead over the wire and run down to LV.
15. Test pacing thresholds.
16. Unscrew sheath with helix and remove all sheaths, leaving the wire in LV.
17. Add RV and LV lead and device.

In another embodiment, a medical device delivery method of the present disclosure may follow this general procedure, which uses a cranial-caudal angle and an aortogram and/or LV ventriculogram:
1. Place a guide wire or sheath or lead deep in the CS and down the great cardiac vein to the apex. This wire provides guidance as to the location of the CS ostium and shows the valve plane.
2. Place another wire in the middle cardiac vein.
3. The crossing of these two wires is the approximate place to attach the helix sheath.
4. Find the cranial-caudal angle that provides the most perpendicular view to the valve plane in a DV view and the most parallel view in a lateral view.
5. Take an aortic angiogram and LV ventriculogram. Take these from both the DV view and the lateral view with the cranial/caudal angle determined in 4 above.
6. Place a flexcath catheter in the atrium and pull the curve, so the tip of the catheter is near the CS ostium, and the last inch of the catheter is pointing more apical in the lateral view and at the aorta in the DV view.
7. Guide the inner sheath with the attached helix to the tip of the flexcath. Engage the helix into the tissue adjacent the tip of the flexcath, using contrast as necessary.
8. Advance the flexible needle a few millimeters outside of the dilator. The easiest way to do this is to put a torquer tool on the needle proximal end and lock it at a point at which the needle is about 2-3 mm distal to the end of the dilator.
9. Advance the dilator/needle combination until the needle touches the tissue. Record the EGM from the needle.
10. Pace through the needle and record the 12-lead ECG on the Pruka.
11. Advance the dilator/needle a few millimeters at a time and record paced and intrinsic beats on the 12-lead ECG.
12. When the dilator needle reaches the LV chamber, pull back the dilator/needle until it just begins to pace the tissue. Record the pacing threshold at this point.
13. If there is a poor threshold, pull back needle and wire, re-aim the flexcath (e.g. more lateral or apical, etc), and go back to step 9.
14. If there is a good threshold, then push wire deeper into LV, remove needle, and sheath.
15. Place pacing lead over the wire and run down to LV.
16. Test pacing thresholds.
17. Unscrew sheath with helix and remove all sheaths, leaving the wire in LV.
18. Add RV and LV lead and device.

Figure 21:
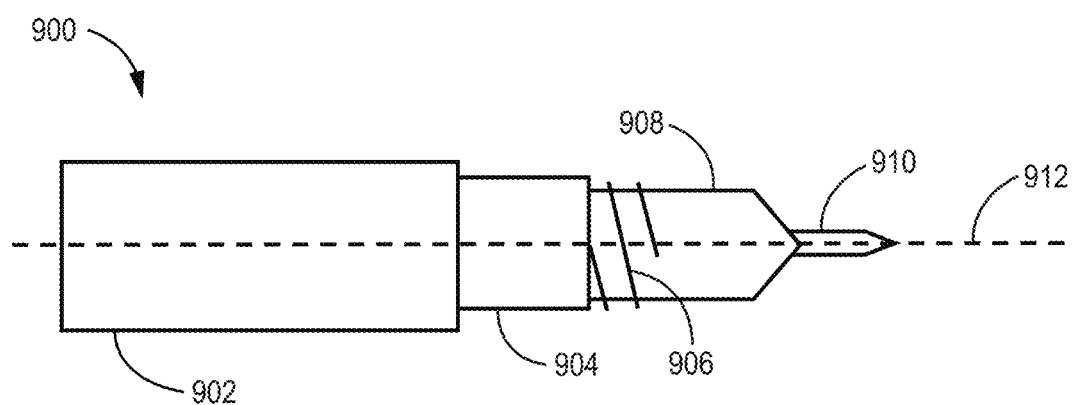
FIG. 21 is a diagram of a medical device delivery system for use with, e.g., the methods of FIGS. 16-20 and/or the illustrative systems and devices of FIGS. 1-4, 13-15, and 22.

FIG. 21 shows a medical device delivery system 900, which may include one or more of a steerable element 902, a fixation sheath 904 with a fixation element 906, a dilator 908, a flexible needle 910, and a guide wire 912. The fixation element 906 of the fixation sheath 904 may be attachable to the right-atrial endocardium in the triangle of Koch region in the right atrium of the patient's heart. The flexible needle 910 may be freely translatable in a longitudinal direction relative to the fixation sheath 904. The steerable element 902 may be configured to steer the fixation sheath 904.

When assembled for introduction into the patient's heart, the flexible needle 910 may be at least partially disposed in a lumen of the fixation sheath 904. The dilator 908 may be at least partially disposed in the lumen of the fixation sheath 904, and the flexible needle 910 may be disposed at least partially in a lumen of the dilator 908. The guide wire 912 may be at least partially disposed in the lumen of the fixation sheath 904 and/or the flexible needle 910.

In some embodiments, the fixation element 906 is a helical attachment element, and the fixation sheath 904 is freely rotatable relative to the steerable element 902. In some embodiments, the steerable element 902 may be a steerable sheath. The fixation sheath 904 may be at least partially disposable in a lumen of the steerable sheath.

Various implantable medical devices may be configured for use in conjunction with the delivery system 900. In some embodiments, a medical device may be configured to run over or along the guide wire 912 for implantation in the right atrial endocardium in the triangle of Koch region in the right atrium of the patient's heart. For example, the implantable medical device may include one or more of a right-atrial electrode, a left-ventricular electrode, an intracardiac pacing device, a leadlet, and a lead. The left-ventricular electrode may be implantable from the triangle of Koch region of the right atrium through the right atrial endocardium and central fibrous body and configured to deliver cardiac therapy to or sense electrical activity of the left ventricle in the basal and/or septal region of the left ventricular myocardium of a patient's heart. The right-atrial electrode may be configured to deliver cardiac therapy to or sense electrical activity of the right atrium of the patient's heart.

Figure 22:
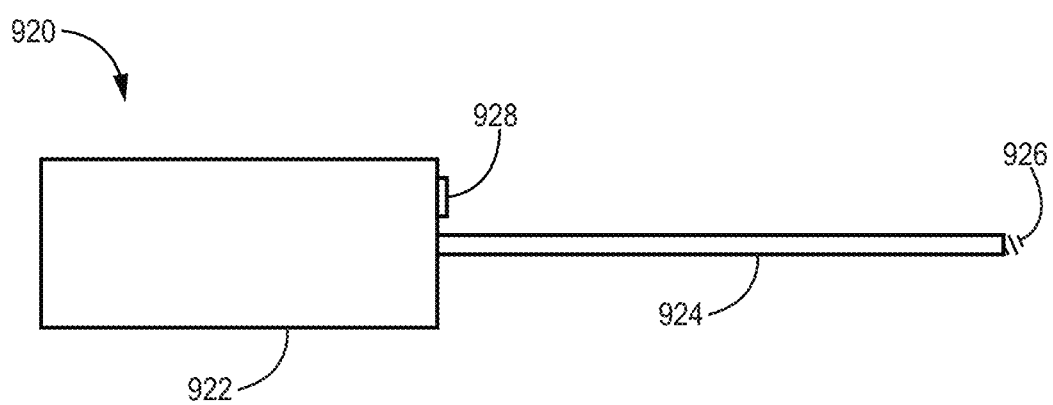
FIG. 22 is a diagram of an implantable medical device that may be implanted with, e.g., the methods of FIGS. 16-20 and/or using the medical device delivery system of FIG. 21.

FIG. 22 shows an implantable medical device 920 that may be implanted with various methods described herein and/or using medical device delivery systems described herein. The device 920 may include one or more of an intracardiac housing 922 and a leadlet 924. The device 920 may include a plurality of electrodes coupled to the intracardiac housing 922, the leadlet 924, or both.

In some embodiments, the plurality of electrodes includes a left-ventricular electrode 926 implantable from the triangle of Koch region of the right atrium through the right atrial endocardium and central fibrous body to deliver cardiac therapy to or sense electrical activity of the left ventricle in the basal and/or septal region of the left ventricular myocardium of a patient's heart. As illustrated, the left-ventricular electrode 926 is coupled to a distal end portion of the leadlet 924. In some embodiments, the plurality of electrodes includes a right-atrial electrode 928 positionable within the right atrium to deliver cardiac therapy to or sense electrical activity of the right atrium of the patient's heart. As shown, the right-atrial electrode 928 is coupled to a distal end portion of the intracardiac housing 922.

The intracardiac housing 922 may include various components similar to the leadless pacing devices described herein, which are not shown again here. In particular, the intracardiac housing may at least partially contain a therapy delivery circuit operably coupled to the plurality of electrodes to deliver cardiac therapy to the patient's heart, a sensing circuit operably coupled to the plurality of electrodes to sense electrical activity of the patient's heart, and a controller having processing circuitry operably coupled to the therapy delivery circuit and the sensing circuit. The controller may be configured to monitor electrical activity of the right atrium using the right-atrial electrode, the left ventricle using the left-ventricular electrode, or both. The controller may also be configured to deliver cardiac therapy based on the monitored electrical activities using at least one of the plurality of electrodes.

Figure 23:
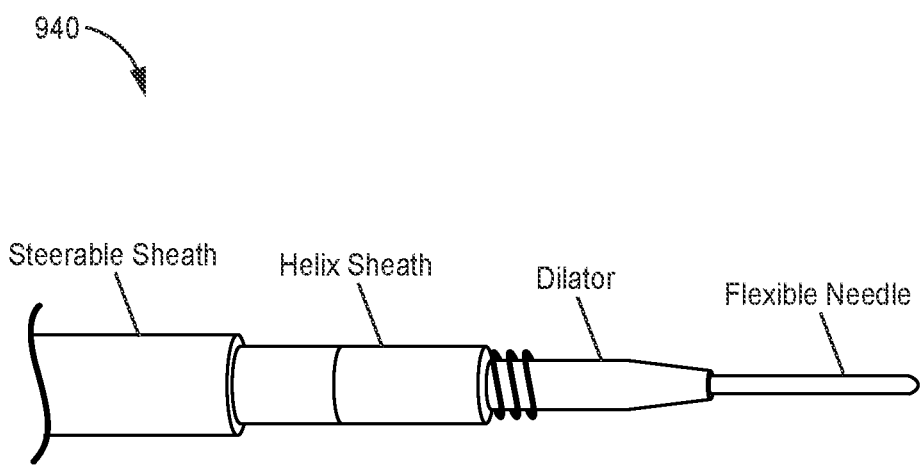
FIG. 23 is an illustration of one example of the medical device delivery system of FIG. 21.

FIG. 23 shows one illustrative system 940 of the medical device delivery system 900 (FIG. 21). In the illustrated embodiment, the flexible needle, dilator, and helix sheath with a helix (e.g., fixation sheath) are all at least partially disposed inside of the steerable sheath. The distal end of the steerable sheath can be held against the tissue, and the helix can be attached to the tissue of the heart. The needle and dilator can be tunneled to the LV.

In some embodiments, the illustrative system 940 may be assembled by first fitting the helix sheath inside the steerable sheath. This may allow the helix sheath to be turned independently of the steerable sheath to fix the helix into the desired location in the heart. Once the helix sheath is fixed to the tissue, the helix sheath may provide a very stable platform to inject the needle or wires or lead into the heart.

Next, the dilator, which may be described as another coaxial sheath with the steerable sheath and the helix sheath, may contain the flexible needle. The dilator may be used to bring the needle safely down the helix sheath.

The needle may be loaded into the dilator, and the tip of the needle may be placed just proximal to the exit, or distal end, of the dilator. Once the helix is attached to the tissue, the needle may be extended a few millimeters beyond the end of the dilator.

Pacing pulses may then be applied to the needle, and the response may be recorded on a 12-lead ECG on an electrophysiological recording system, such as a Pruka. The needle and dilator may be pushed a few mm at a time, and the 12-lead ECG may be recorded with and without pacing. When the threshold increases significantly, this may indicate that the needle is in the LV chamber.

If the threshold or activation pattern is not acceptable, repositioning may be desirable. The needle and dilator may be retracted, and the steerable sheath may be simply "re-aimed" by pushing in, pulling out, or rotating the steerable sheath. When a new direction is found, the needle may be re-inserted to the LV, and the thresholds and activation may be tested again.

If the pacing threshold and ventricular activation pattern are acceptable, then a 0.014" guide wire may be extended into the LV through the flexible needle.

Figure 24:
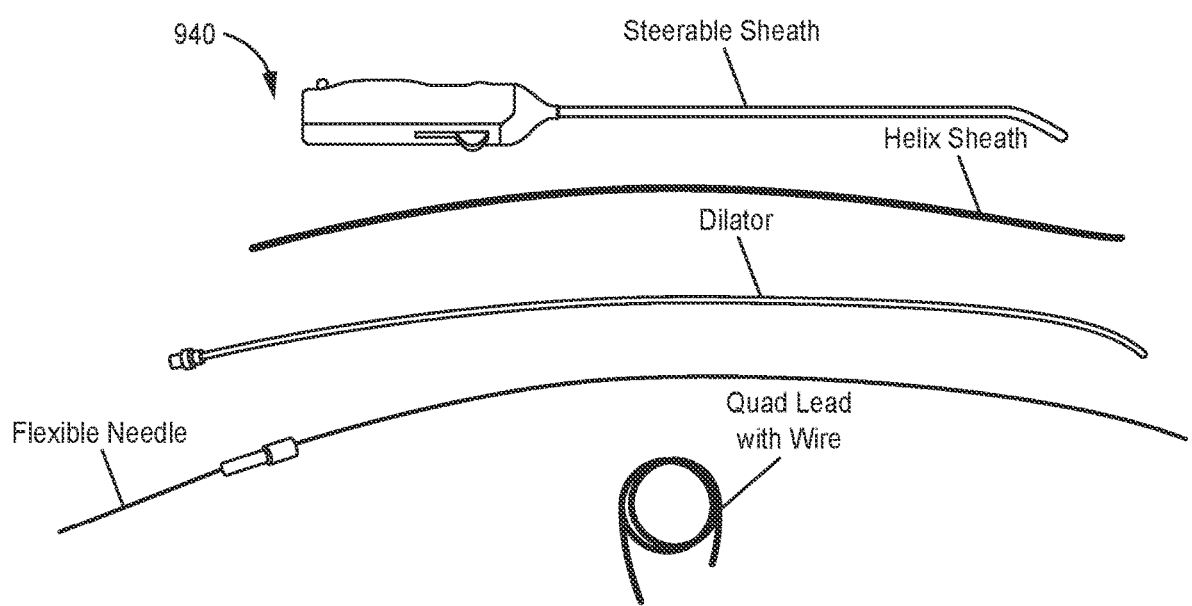
FIG. 24 is an illustration of components of the medical device delivery system of FIG. 23 as a kit.

FIG. 24 shows various components of the illustrative system 940 as a kit. The illustrative system 940 may include: a sheath with a helix that is screwed into the triangle of Koch, a "needle" or tunneling tool that can pace, and a guide wire would be left in the tunnel to allow easy placement of the leadlet. A leadlet may be delivered over the guide wire as part of the leadless pacer system. Such a system may facilitate easy retrieval as the leadlet would provide a convenient connection.

In some embodiments, the illustrative system 940 may more particularly include: a steerable sheath, a straight sheath with a soft distal section and a stiff helix attached to the end (which may fit within the steerable sheath), a flexible hypotube with a tip sharpened like a needle, a dilator with an internal diameter that accepts the flexible hypotube, a 0.014" or 0.018" guide wire over which the lead can be delivered, and a bipolar LV lead. The internal diameter of the hypotube/needle may be sized to accept the 0.014" or 0.018" guide wire. The distal end of the hypotube/needle may be insulated except for the last about 2 mm, which may facilitate pacing and sensing from the flexible needle.

Figure 25:
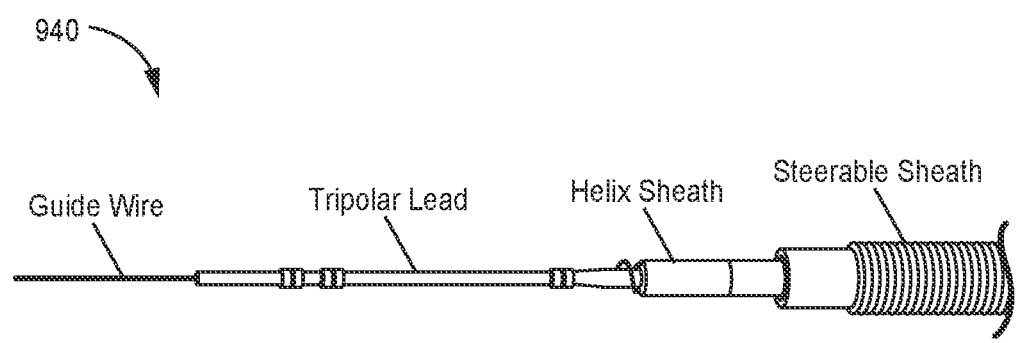
FIG. 25 is an illustration of the medical device delivery system of FIG. 23 in use with a lead.

FIG. 25 shows the illustrative system 940 in use with a lead. For example, the needle and dilator may be removed and replaced by the lead. As illustrated, the illustrative system 940 may be configured for use with a steerable sheath, a helix sheath, a tripolar lead shown exiting the helix sheath, and a guide wire exiting the tripolar lead.

While the present disclosure is not so limited, an appreciation of various aspects of the disclosure will be gained through a discussion of the specific examples provided below. Various modifications of the examples, as well as additional embodiments of the disclosure, will become apparent herein.

EXAMPLES

A concept for delivering a lead over the wire from the atrium to the left ventricle was tested on pigs. The goal of the experiments was to be able to pace the right atrium and the left ventricle from a single device in the right atrium. In addition, the goal was to provide pacing the ventricles with a short QRS in an attempt to provide "resynchronization" of the heart. One theory is that pacing high on the septal LV may engage both the endocardial fibers, which are believed to have rapid conduction, and left bundle branch fibers, which are known to have rapid conduction. In particular, the concept tested was the delivery of an over the wire pacing lead from the right atrium near the coronary sinus (CS) ostium to the basal left ventricular (LV) septum.

Example 1

Figures 26A, 26B:
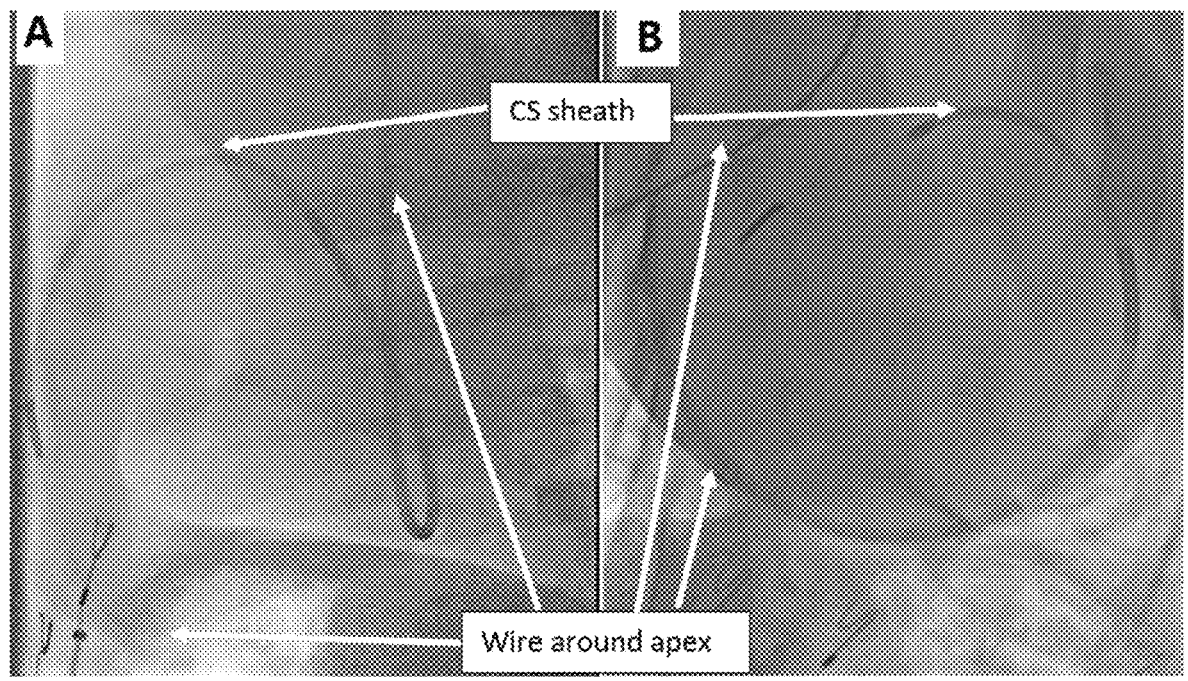
FIGS. 26A-B are X-ray images of catheters in the coronary sinus (CS) and a guide wire in the middle cardiac vein.

We used a pig that weighed 94 kg. The pig was in dorsal recumbency. A jugular cut down was performed, and a Sentrant 20 Fr sheath was placed in the jugular vein. A guide wire was placed in the coronary sinus and directed down the anterior interventricular vein and back up the middle cardiac vein. This outlined the septum. A lead was placed in the middle cardiac vein. The point at which the middle cardiac vein lead and the CS lead crossed created a target for the triangle of Koch. The fluoroscope was moved to find the angles that showed a view parallel to the valve plane and a view that was perpendicular to the valve plane. These two images are shown in FIGS. 26A-B.

Figures 27A, 27B:
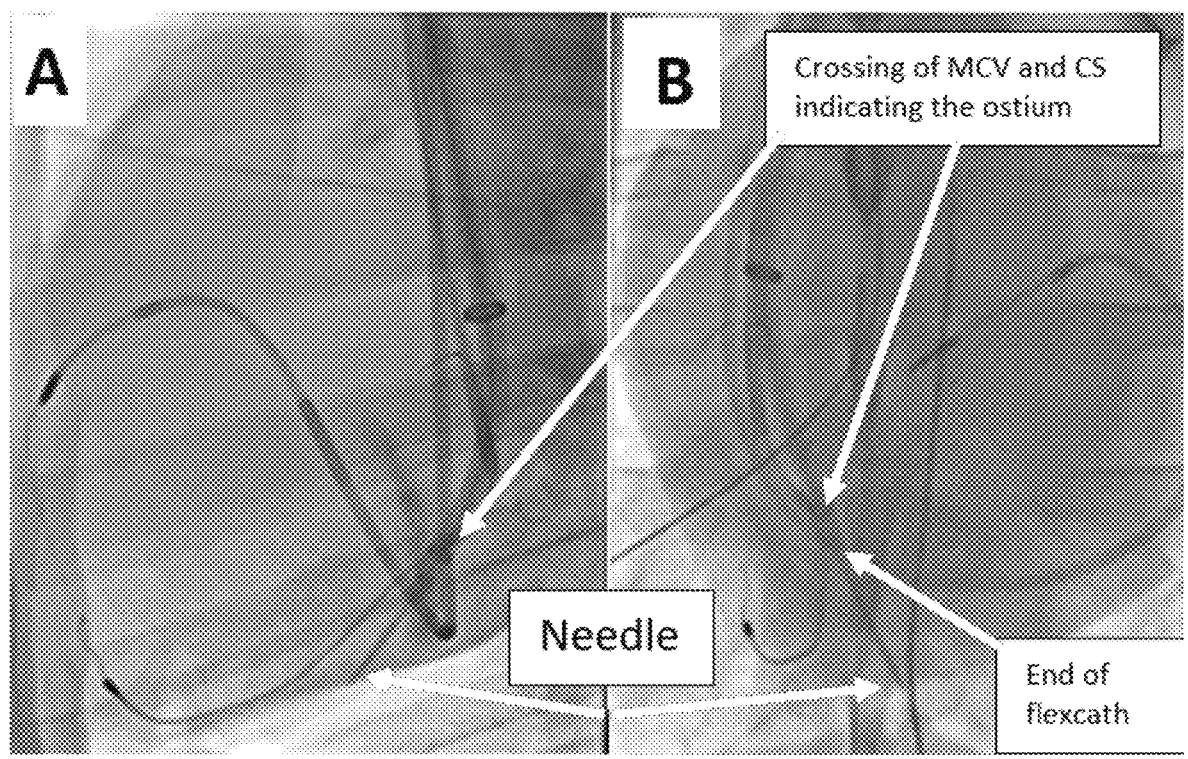
FIGS. 27A-B are X-ray images showing the orientation of a flexcath (e.g., steerable sheath) and a needle for first penetration.
Figures 28A, 28B:
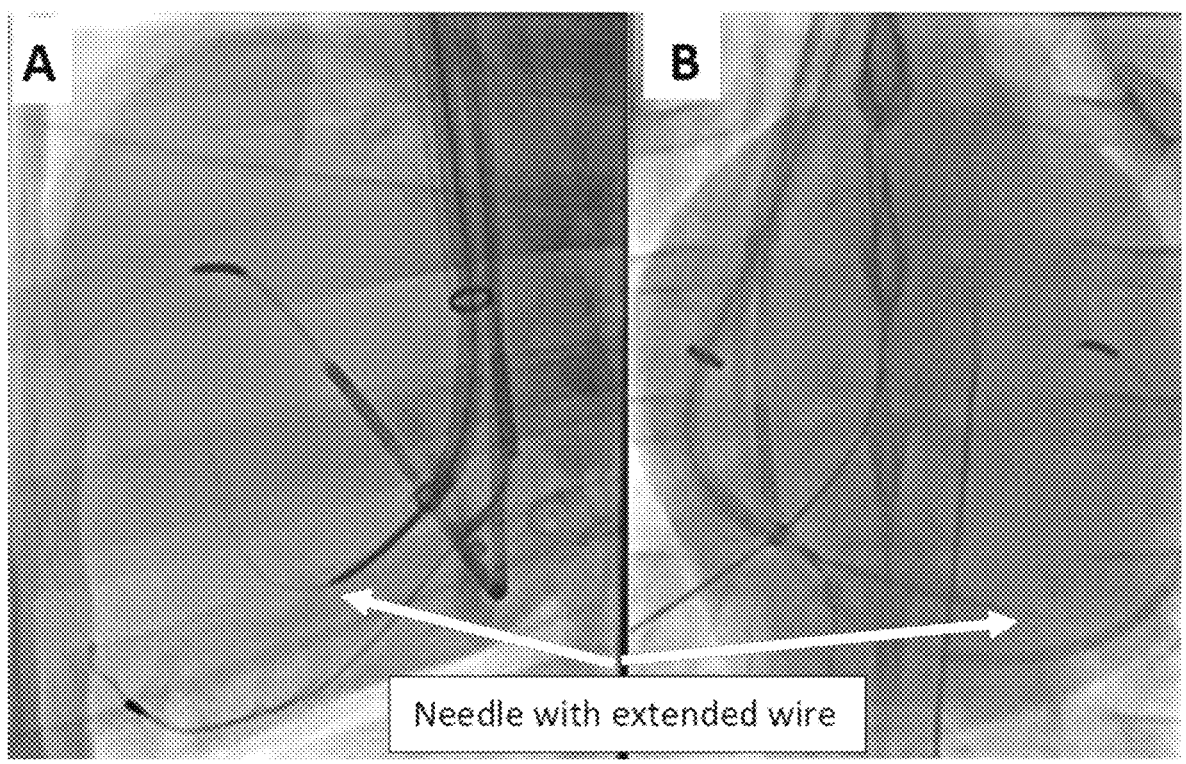
FIGS. 28A-B are X-ray images showing a second implant location and the needle with dilator over the top. In addition, the 0.014" wire is extended into the left ventricle (LV).

Then, a modified flexcath was inserted into the coronary sinus, and a curve was pulled to attempt to aim the shaft toward the left ventricle. The crossing of the MCV and CS wires was used as a starting point for the tip of the flexcath after it was curved. The angle was reverted back to the 0 degrees cranial images. The images shown in FIGS. 27A-B may have provided more accurate aiming. The helix on the inner sheath was then attached to the adjacent tissue by rotating the sheath. The before and after images are shown in FIGS. 28A-B.

The catheter was redirected, and another needle injection was attempted. The final needle position can be seen in FIGS. 28A-B. The angle of the needle in the DV image is closer to the aorta.

Figures 29A, 29B:
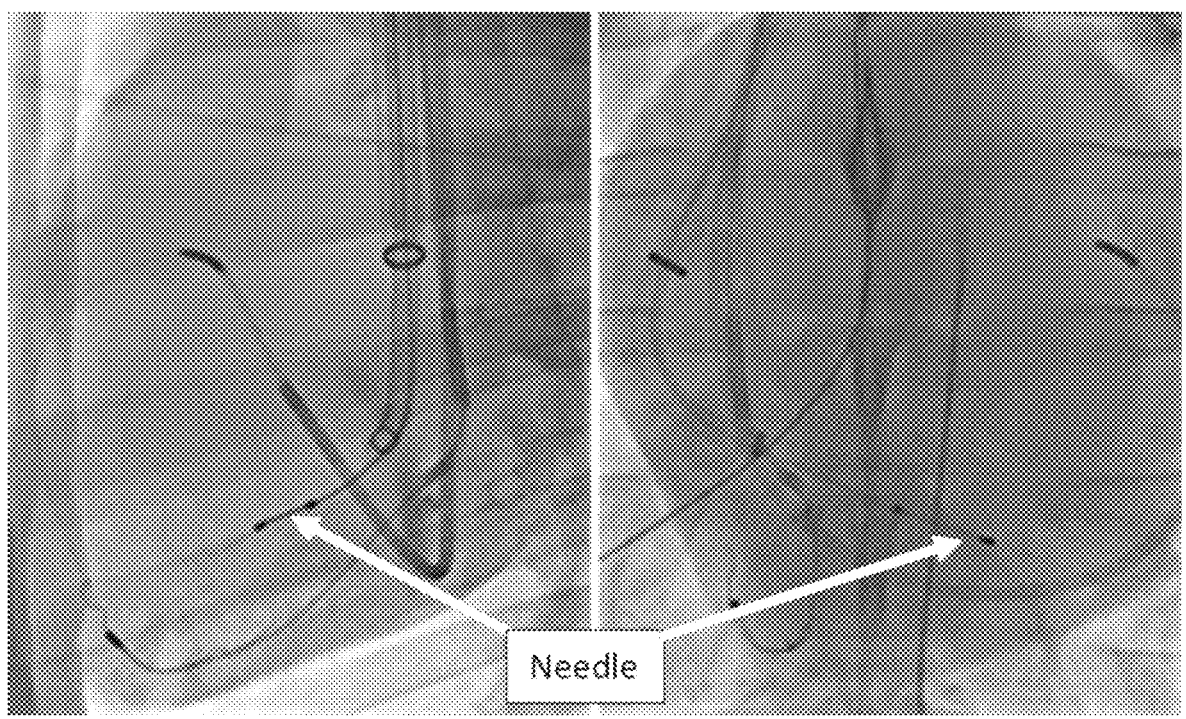
FIGS. 29A-B are X-ray images showing a final position for lead placed over a guide wire crossing from the right atrium (RA) to the LV. Electrodes are shown on the lead.

The needle and dilator were removed, and the lead was run over the wire into the LV. The lead position is shown in FIGS. 29A-B. The lead is in a very similar location to the needle and wire from FIGS. 28A-B.

Figures 30A, 30B:
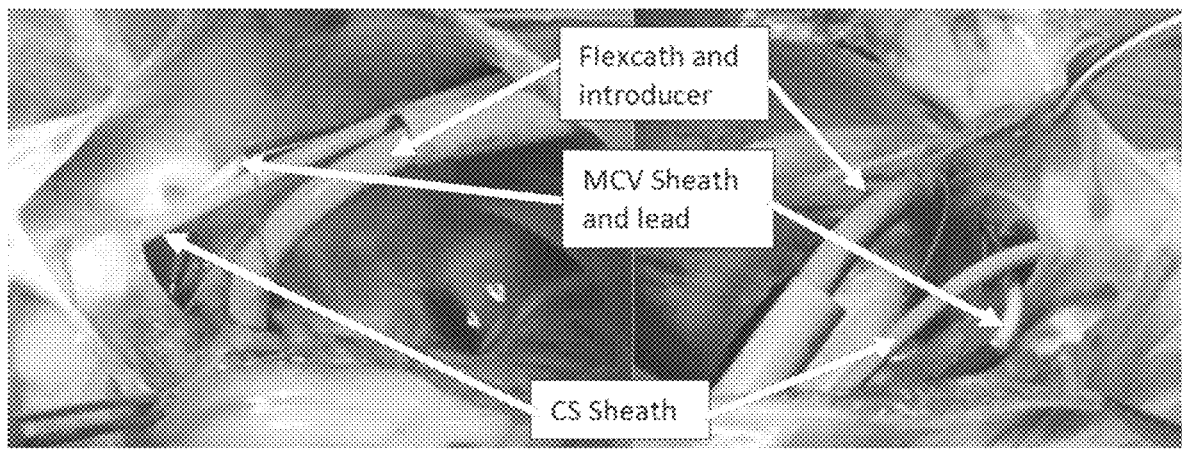
FIGS. 30A-B are images showing a second passage of needle and wire into tissue showing the flexcath, the MCV lead catheter, and the CS catheter. The MCV and CS sheaths cross very near the CS ostium.

The animal was then transferred to necropsy, and the heart was opened to view the course of the catheters and leads. As can be seen in FIGS. 30A-B, the CS catheter and MCV catheter meet near the CS ostium (which is actually the azygos vein ostium). The flexcath, helix sheath, and lead enter the tissue near the tricuspid annulus, or very near the base of the triangle of Koch (TOK).

Figure 31:
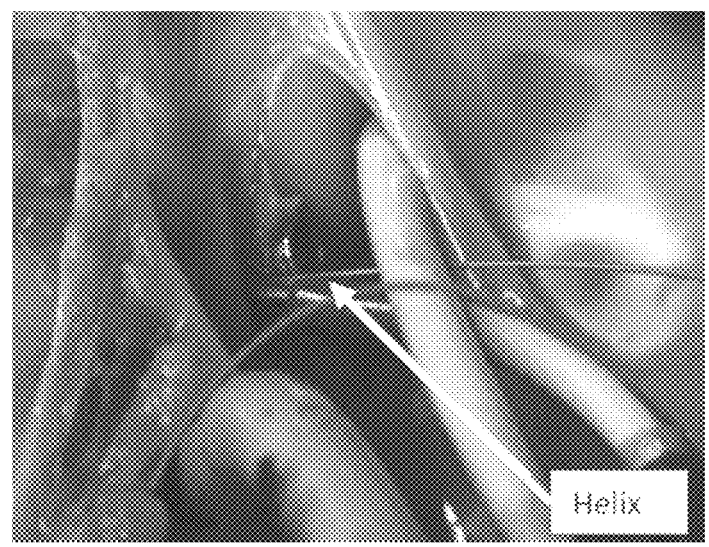
FIG. 31 is an image of the helix that indicates the position of the first needle and wire passage. The entry for this attempt was inside the CS but still near the tricuspid valve.

During the first attempt at passing the needle and dilator into the LV, the trajectory was determined to be incorrect. However, during manipulations, the helix came off the sheath. The helix was found inside the CS. A comparison of this location in FIG. 31 with the fluoro image shown in FIGS. 27A-B reveals that by using the crossing of the MCV and CS sheaths to indicate the CS ostium, one can estimate a distance to this structure with attempting to attach the helix.

Figure 32A:
FIGS. 32A-B are images of the lead exit into LV chamber. The lead coursed from the CS ostium very low near the tricuspid annulus to the posterior papillary muscle in the LV.
Figure 32B:

The lead was found in the LV. The lead had exited the endocardium into the chamber near the posterior papillary muscle, and the tip was behind the posterior papillary muscle. The tip was quite basal near the mitral valve as can be seen in FIGS. 32A-B.

Example 2

Figures 33A, 33B:
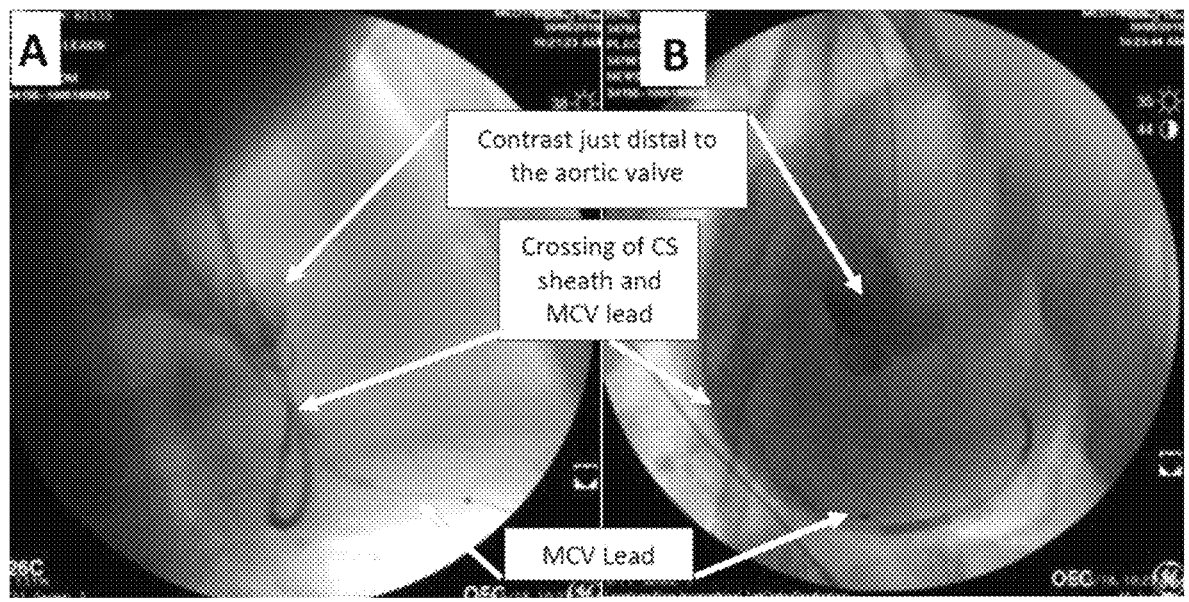
FIGS. 33A-B are X-ray images of the catheters in the CS and the wire in the MCB.

A pig was used that was in dorsal recumbency. A jugular cut down was performed, and a shortened 24 Fr Micra-like introducer was placed in the jugular vein. A wire was attempted to be placed deep in the CS, but the great cardiac vein divided into nothing before it dove for the apex. A guide catheter was placed as distal as possible. The middle cardiac vein was a challenge to cannulate. A lead was placed in the middle cardiac vein. The point at which the middle cardiac vein lead and the CS lead crossed created a target for the triangle of Koch. The fluoroscope was moved to find the angles that showed a view parallel to the valve plane and a view that was perpendicular to the valve plane. The best angle was 25 degrees caudal for both the lateral and DV images. These two images are shown in FIGS. 33A-B.

Figures 34A, 34B:
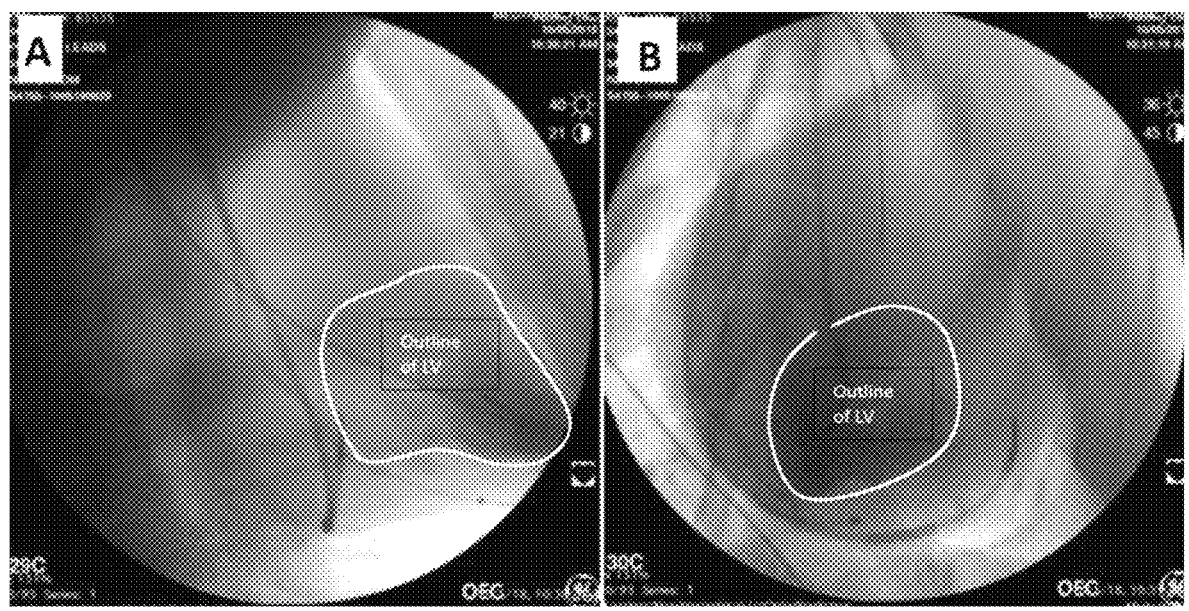
FIGS. 34A-B are X-ray images of contrast injection into the LV.

A ventriculogram was performed from both lateral and DV in order to understand where the LV endocardium was. These are shown in FIGS. 34A-B.

With these images, a good definition of the cardiac anatomy and landmarks to use for navigation was established. The MCV lead pulled out during manipulations of the flexcath and was not re-implanted. Navigated was performed without the MCV lead. The flexcath would be directed toward the crossing of the MCV lead and the CS sheath in both views. The helix sheath would be attached to the heart near this point. Then, the flexcath would be curved and rotated such that in the lateral view it was pointed just apical of the aortic valve in the lateral view and toward the aorta in the DV view. The first attempt in this direction is shown in FIGS. 35A-B.

Figures 35A, 35B:
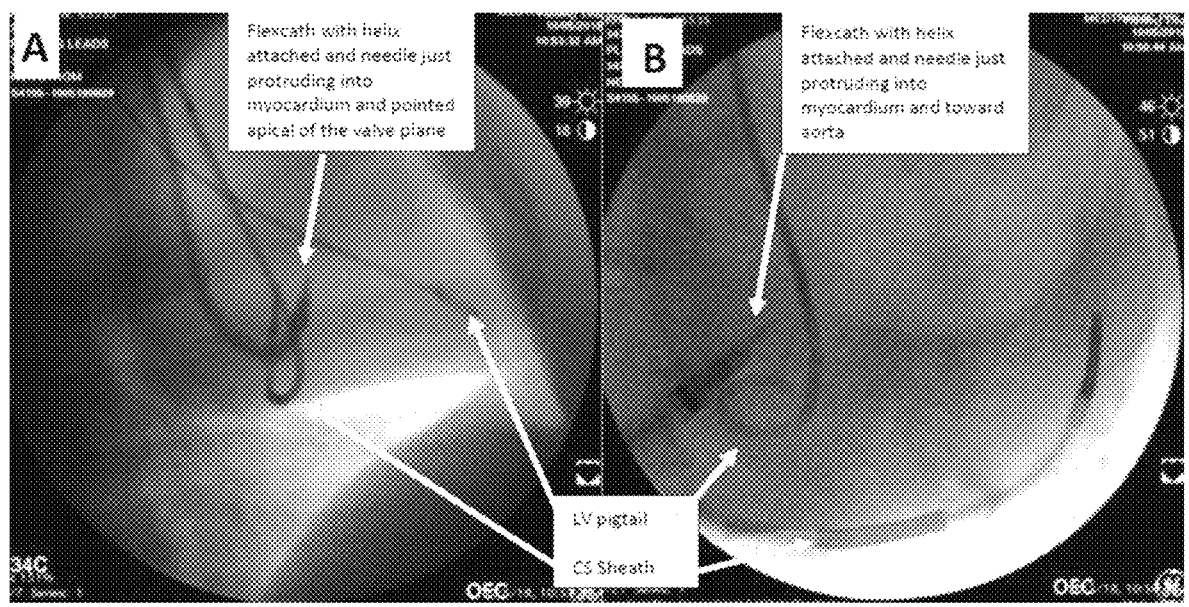
FIGS. 35A-B are X-ray images showing an orientation of flexcath and needle for first penetration.

The flexcath appeared far from the CS toward the aorta in the DV view in FIGS. 35A-B, possibly due to distortion of the heart by the stiff flexcath. The needle and guidewire were extended into the LV. These images can be seen in FIGS. 36A-B.

Figure 36A:
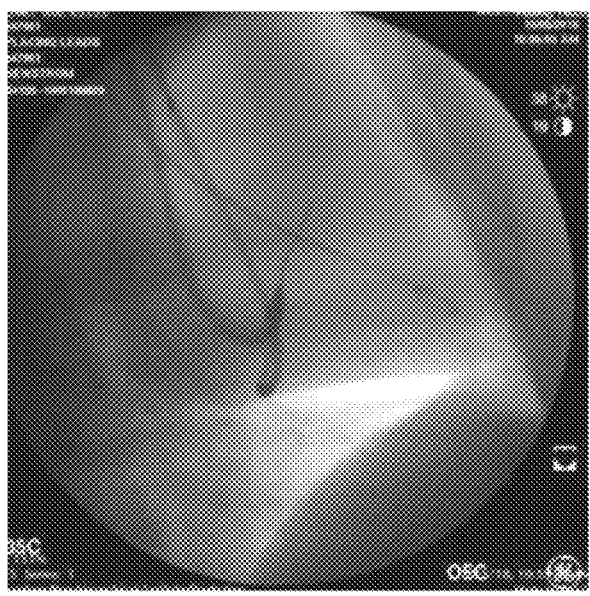
FIGS. 36A-B are X-ray images showing a first implant location and the needle with dilator extended into the LV.
Figure 36B:
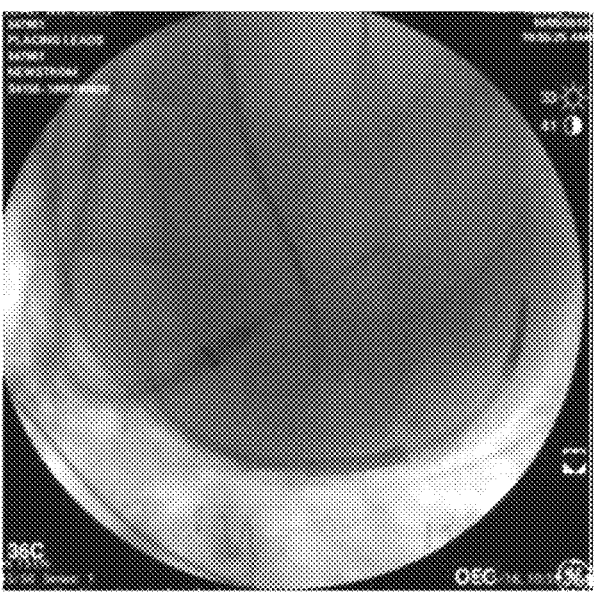
Figures 37A, 37B:
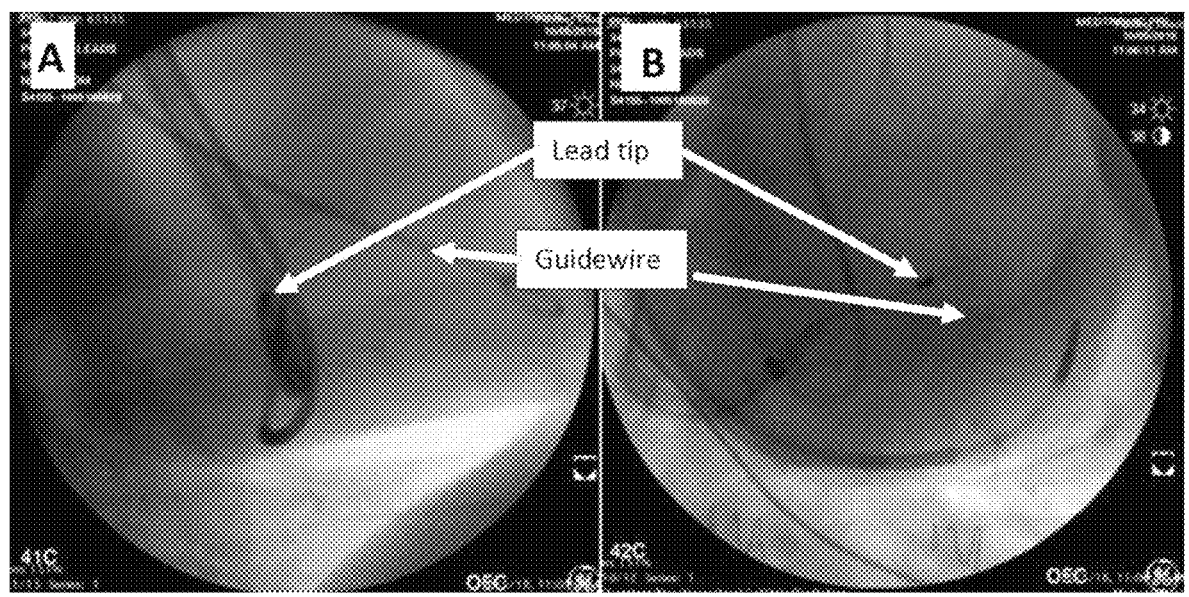
FIGS. 37A-B are X-ray images showing a final position for lead crossing from the RA to the LV. The lateral view shows the lead at the helix while the DV view shows the lead tip in the LV chamber. The course of the lead in the lateral view is shown by the guidewire.
Figures 38A, 38B:
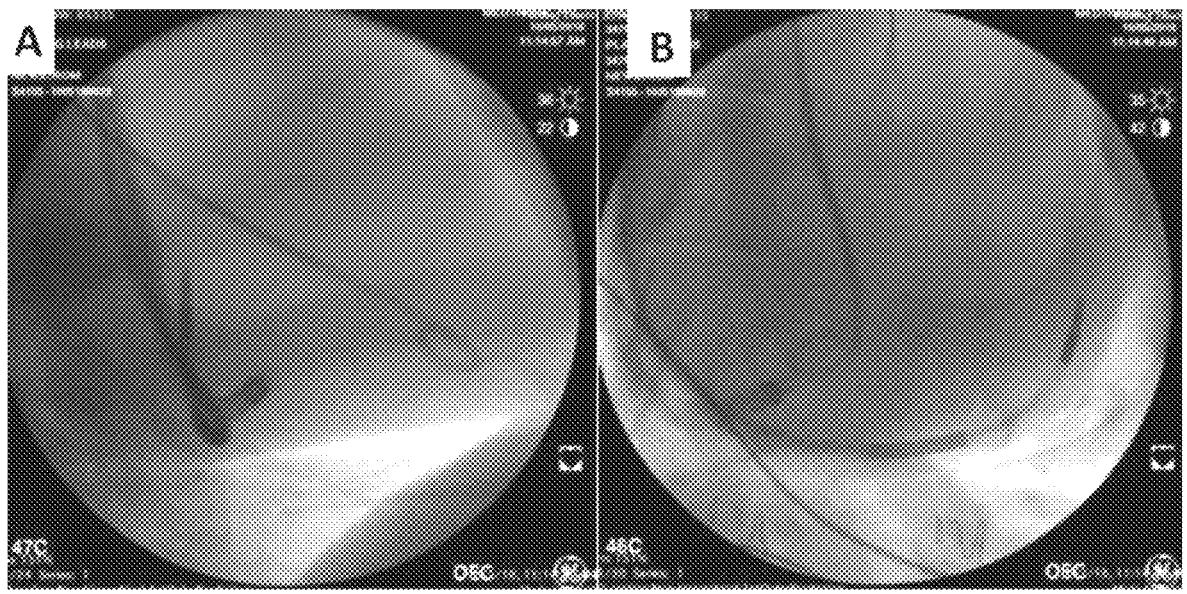
FIGS. 38A-B are X-ray images showing a second implant of the lead showing the position of the flexcath and the helix prior to needle insertion.
Figures 39A, 39B:
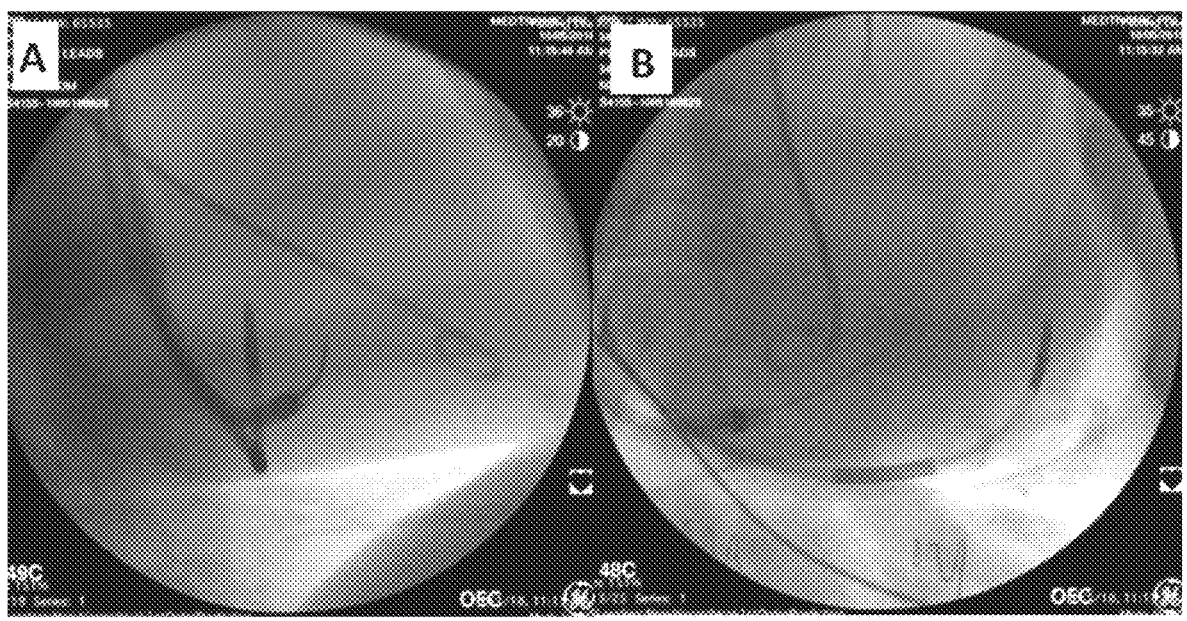
FIGS. 39A-B are X-ray images showing the needle and the dilator extended into the LV.
Figures 40A, 40B:
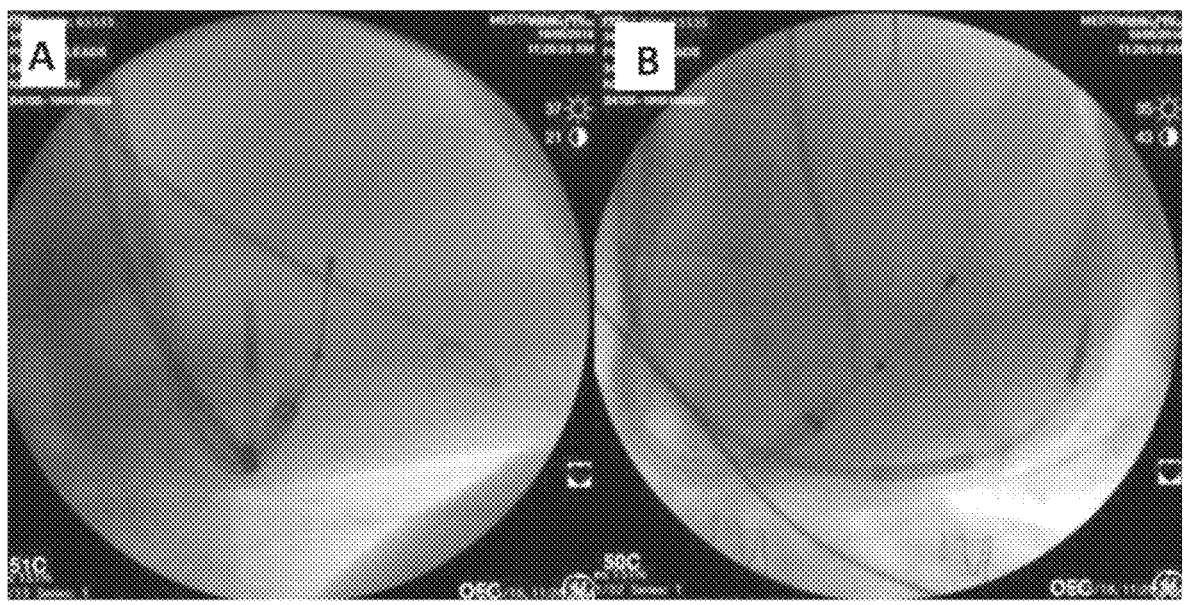
FIGS. 40A-B are X-ray images showing a bipolar lead over the wire extended into the LV.
Figures 41A, 41B:
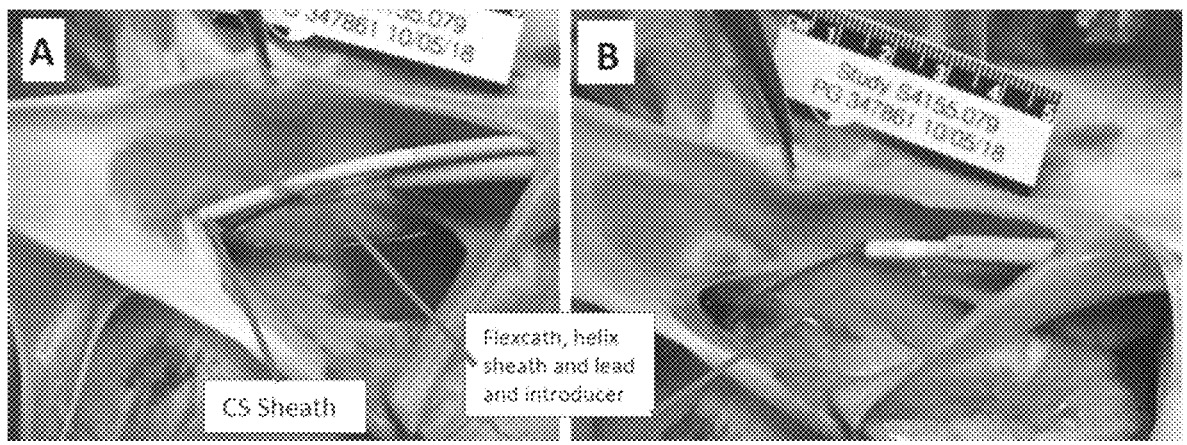
FIGS. 41A-B are images showing a second passage of needle and wire into tissue showing the flexcath and the CS catheter. The entry to the MCV is not shown.
Figure 42A:
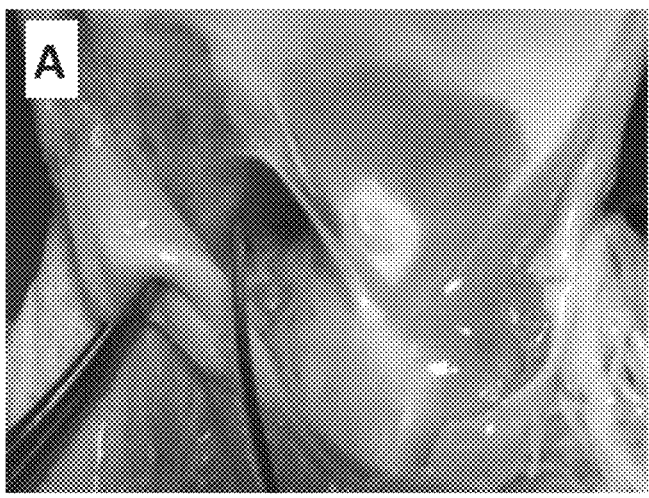
FIGS. 42A-B are images showing the lead entry site in the CS near the ostium. The site is right on the base as can be seen in FIG. 42B. Another site of entry appears about 1 cm "down" in the image from the lead entry site shown. This another site of entry may be the first, or original, penetration site after which the tools were removed before making a second attempt.
Figure 42B:
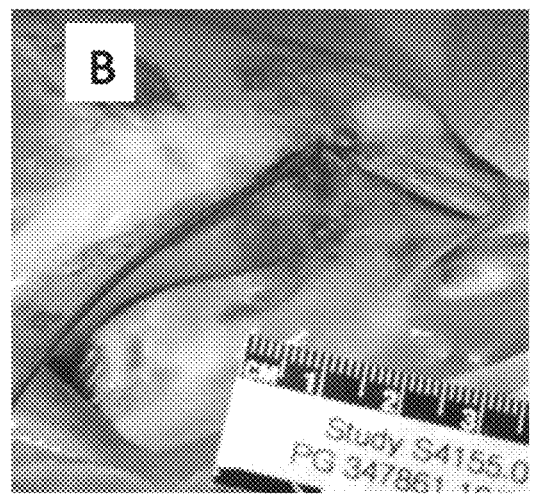
Figures 43A, 43B:
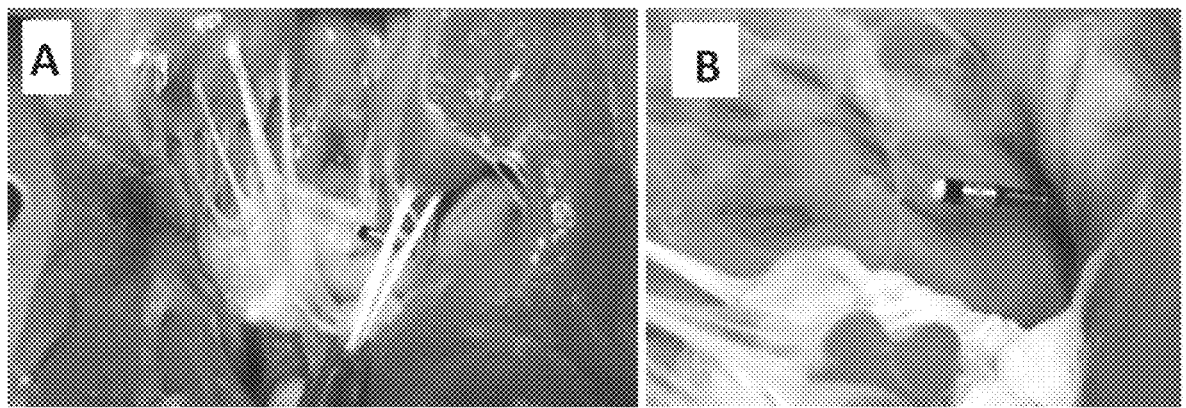
FIGS. 43A-B are images showing the lead tip in the left chamber. The valve is the mitral valve and, in both FIG. 43A and FIG. 43B, the lead tip can be seen protruding from under the posterior papillary muscle. This appears more toward the wall of the LV than in the middle of the chamber.
Figures 44A, 44B:
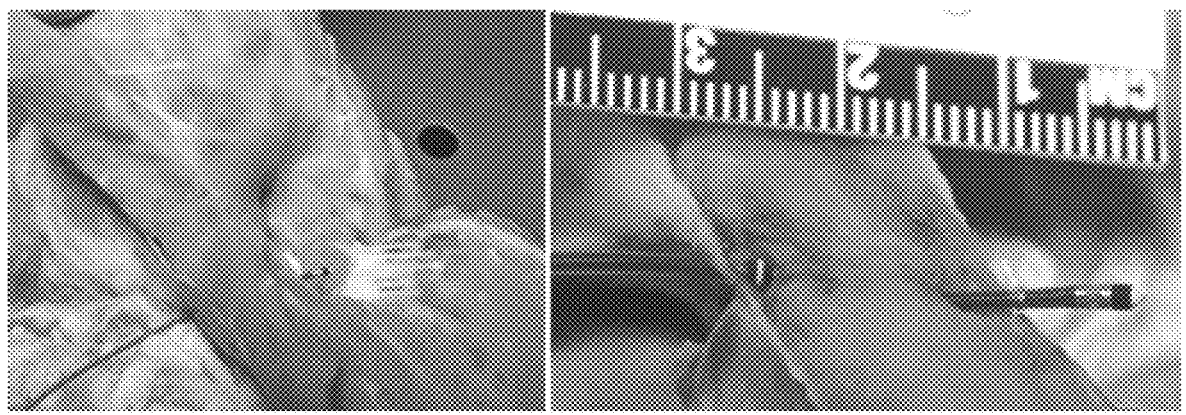
FIGS. 44A-B are images showing the lead crossing the septum. The crossing is relatively perpendicular to the tissue. Although this can be changed, the goal here was to exit into LV chamber with a perpendicular path.

A 0.014" guide wire was run out the needle, the needle and dilator were removed, and the lead was run over the wire into the LV. The lead position is shown in FIGS. 36A-B. As illustrated, the helix is not pointing toward the apex, but the wire course is in the left ventricle. The lead is in a very similar location to the needle and wire from FIGS. 35A-B. It was very difficult to push the lead into the ventricle. The lead stuck right where the helix was bound in the tissue, possibly due to the inability of the tissue to expand within the helix.

The lead was then removed, and the helix was detached from the tissue. A second lead implant was attempted, again without the MCV lead. As before, the flexcath was guided to the CS ostium (using a guess based on previous images) and then curved apically and toward the aorta. The helix was engaged in the tissue, and the needle and dilator were directed out of the helix into the LV chamber. Pacing thresholds and 12-lead ECGs were recorded along the way.

The second implant of the lead appeared to go where it was anticipated. In the lateral view, the lead was slightly apical from the CS, so the final position would be quite basal. In the DV view, the lead appeared to cross directly under the aorta, which should result in a fairly perpendicular crossing of the septum.

A 12-lead ECG was used, and pacing thresholds were taken while advancing the needle across the septum. There were no lead thresholds taken.

The animal was then transferred to necropsy, and the heart was opened to view the course of the catheters and leads. As can be seen in FIGS. 41A-43B, the lead entry site in the CS was close to the ostium and very near the base. The MCV lead fell out before the flexcath leads were tunneled. However, based on the fluoro images saved when the MCV lead was in place, the lead tunnel was able to be started quite close to the CS ostium. It appears the two tunnels started close to each other. However, the outlet of the first tunnel in the LV could not be found, and there was no lead or wire left in place. The flexcath, helix sheath, and lead entered the tissue near the tricuspid annulus, or very near the base of the triangle of Kock (TOK). It appears that the use of the CS and MCV structures provided a location to identify the TOK.

The lead was found in the LV. It had exited the endocardium into the chamber near the posterior papillary muscle, and the tip was behind the posterior papillary muscle. It was quite basal near the mitral valve. It can be seen in FIGS. 43A-B.

Thus, various embodiments of VFA DELIVERY SYSTEMS AND METHODS are disclosed. Various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as performed by a single module or unit for purposes of clarity, the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

All references and publications cited herein are expressly incorporated herein by reference in their entirety for all purposes, except to the extent any aspect incorporated directly contradicts this disclosure.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g., 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out at least some functionality (for example, a first medical device may be operatively coupled to another medical device to transmit information in the form of data or to receive data therefrom).

Terms related to orientation, such as "top," "bottom," "side," and "end," are used to describe relative positions of components and are not meant to limit the orientation of the embodiments contemplated. For example, an embodiment described as having a "top" and "bottom" also encompasses embodiments thereof rotated in various directions unless the content clearly dictates otherwise.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like.

The term "and/or" means one or all the listed elements or a combination of at least two of the listed elements.

The phrases "at least one of," "comprises at least one of," and "one or more of" followed by a list refers to any one of the items in the list and any combination of two or more items in the list.

The invention claimed is:

1. A medical device delivery system comprising:
   a fixation sheath comprising a fixation element attachable to a right-atrial endocardium in the triangle of Koch region in the right atrium of a patient's heart;
   a steerable sheath defining a lumen and configured to steer the fixation sheath, wherein the fixation sheath is at least partially disposed in the lumen of the steerable sheath and the fixation sheath is freely rotatable relative to the steerable sheath;
   a flexible needle at least partially disposable in a lumen of the fixation sheath and configured to flex with the fixation sheath when disposed in the lumen of the fixation sheath and the fixation sheath is steered by the steerable sheath;
   a guide wire at least partially disposable in the lumen of the fixation sheath, and
   an implantable medical device configured to advance over or along the guide wire, wherein the implantable medical device comprises a left ventricular electrode implantable from the triangle of Koch region of the right atrium through the right-atrial endocardium and central fibrous body and configured to deliver cardiac therapy to or sense electrical activity of the left ventricle in the basal and/or septal region of the left ventricular myocardium of a patient's heart, and
   wherein the fixation element of the fixation sheath is configured to anchor the fixation sheath to the right-atrial endocardium at least during delivery of the flexible needle through the triangle of Koch region in the right atrium of a patient's heart.

2. The system of claim 1, wherein the fixation element comprises a helical attachment element.

3. The system of claim 1 or 2, wherein the guide wire is at least partially disposable in a lumen of the flexible needle.

4. The system of claim 1, further comprising a dilator at least partially disposable in the lumen of the fixation sheath, wherein the flexible needle is disposed at least partially in a lumen of the dilator.

5. The system of claim 1, wherein the flexible needle is freely translatable in a longitudinal direction relative to the fixation sheath.

6. The system of claim 1, wherein the implantable medical device further comprises one or more of a leadless device, a leadlet, and a lead.

* * * * *